United States Patent [19]

Brooks et al.

[11] Patent Number: 5,185,363
[45] Date of Patent: Feb. 9, 1993

[54] UREA BASED LIPOXYGENASE INHIBITING COMPOUNDS

[75] Inventors: Dee W. Brooks, Libertyville; Daniel J. Kerkman, Lake Villa; Jonathan G. Martin, Waukegan; Andrew O. Stewart, Wildwood; James B. Summers, Libertyville, all of Ill.

[73] Assignee: Abbott Laboratories, Abbott Park, Ill.

[21] Appl. No.: 768,621

[22] PCT Filed: Mar. 20, 1991

[86] PCT No.: PCT/US90/01488
§ 371 Date: Sep. 30, 1991
§ 102(e) Date: Sep. 30, 1991

[87] PCT Pub. No.: WO90/12008
PCT Pub. Date: Oct. 18, 1990

Related U.S. Application Data

[63] Continuation-in-part of Ser. No. 331,566, Mar. 30, 1989, abandoned, which is a continuation-in-part of Ser. No. 42,491, Apr. 24, 1987, abandoned, which is a continuation-in-part of Ser. No. 856,725, Apr. 25, 1986, abandoned.

[51] Int. Cl.$^5$ ............... A61K 31/38; A61K 333/32; A61K 333/22
[52] U.S. Cl. ............... 514/438; 514/445; 514/447; 549/65; 549/68; 549/76; 549/77
[58] Field of Search ............ 549/65, 68, 76, 77; 514/438, 445, 447

[56] References Cited

FOREIGN PATENT DOCUMENTS 0196184 10/1986 European Pat. Off. .

Primary Examiner—Alan Siegel
Attorney, Agent, or Firm—Jerry F. Janssen

[57] ABSTRACT

Substituted phenyl, naphthyl, and thienyl N-hydroxy urea compounds form a class of potent inhibitors of 5- and 12-lipoxygenase and are thus useful compounds in the treatment of inflammatory disease states where leukotrienes and other products of lipoxygenase enzyme activity are implicated.

5 Claims, No Drawings

UREA BASED LIPOXYGENASE INHIBITING COMPOUNDS

CROSS-REFERENCE TO RELATED APPLICATIONS

This application is a continuation-in-part of copending application Ser. No. 331,566 filed Mar. 30, 1989 now abandoned which, in turn, is a continuation-in-part of application Ser. No. 042,491, filed Apr. 24, 1987, (now abandoned) which is a continuation-in-part of application Ser. No. 856,725, filed Apr. 25, 1986 (now abandoned).

TECHNICAL FIELD

This invention relates to compounds having pharmacological utility, to pharmaceutical compositions comprising the compounds, and to medical methods of treatment. More particularly, this invention concerns compounds which inhibit lipoxygenase enzymes, to methods and compositions for inhibiting lipoxygenase enzymes in human and other mammalian hosts in need of such treatment.

BACKGROUND OF THE INVENTION

5-Lipoxygenase is the first dedicated enzyme in the pathway leading to the biosynthesis of leukotrienes (Samuelsson, B., Science, 120: 568 (1983); Hammarstrom, S., Annual Review of Biochemistry, 52: 355 (1983)). This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-hydroperoxyeicosatetraenoic acid (5-HPETE) which can be reduced to 5-hydroxyeicosatetraenoic acid (5-HETE) or converted to leukotriene A4 ($LTA_4$). This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$.

Other products resulting from further oxygenation steps have also been described (Serhan, C. N., Hamberg, M., and Samuelsson, B., Proceedings of the National Academy of Sciences, USA, 81: 5335 (1985); Hansson, G., Lindgren, J. A., Dahlen, S. E., Hedqvist, P., and Samuelsson, B. FEBS Letters, 130: 107 (1984)).

Products of the 5-lipoxygenase cascade are extremely potent substances which produce a wide variety of biological effects, often in the nanomolar to picomolar concentration range. (Sirois, P., Advances in Lipid Research, R. Paoletti, D. Kritchevesky, editors, Academic Press, 21: 79 (1985).

The remarkable potencies and diversity of actions of products of the 5-lipoxygenase pathway have led to the suggestion that they play important roles in a variety of diseases. Alterations in leukotriene metabolism have been demonstrated in a number of disease states. Examples of some of these are briefly discussed as follows:

1. Asthma

Slow reacting substance of anaphylaxis (SRS-A) has long been recognized as a potentially important mediator of asthma and other allergic diseases (Orange, R. P. and Austen, K. F., Advances in Immunology, 10: 105, 1969). Upon specific antigen challenge, tissues from allergic animals and humans generate and release SRS-A (Kellaway, C. H. and Trethewie, E. R., Quarterly Journal of Experimental Physiology, 30: 121, 1940; Orange, R. P., Stechschulte, D. J., and Austen, K. F., Journal of Immunology, 105: 1087, 1979; Lewis, R. A., Wasserman, S. I., Goetzl, E. J., and Austen, K. F., Journal of Experimental Medicine, 140: 1133, 1974). It produces a slow and sustained contraction of airway smooth muscle preparations from a variety of species in vitro, including man (Drazen, J. M., Lewis, R. A., Wasserman, S. I., Orange, R. P., and Austen, K. F., Journal of Clinical Investigation, 63: 1, 1979; Piper, P. J., Tippins, J. R., Morris, H. R., and Taylor, G. W., Advances in Prostaglandin and Thromboxane Research, 6: 121, 1980; Brocklehurst, W. E. Progress in Allergy, 6: 539, 1962; Berry, P. A. and Collier, H. O. J., British Journal of Pharmacology, 23: 201, 1964). Intravenous administration of SRS-A to guinea pigs results in compromised respiration, primarily due to constriction of small peripheral airways (Drazen, J. M. and Austen, K. F., Journal of Clinical Investigation, 53: 1679, 1974). SRS-A also induces vascular permeability when injected intracutaneously in some species, including man (Orange, R. P., Stechschulte, D. J., and Austen, K. F., Federation Proceedings, 28: 1710, 1969). The chemical identity of SRS-A remained unknown until 1979 when it was found to be a mixture of three leukotrienes ($LTC_4$, $LTD_4$, and $LTE_4$) (Murphy, R. C., Hammarstrom, S., and Samuelsson, B. Proceedings of the National Academy of Sciences, USA, 76: 4275, 1979; Morris, H. R., Taylor, G. W., Piper, P. J., and Tippins, J. R., Nature, 285: 104, 1980). Since this discovery, leukotrienes have been shown to possess all the biological properties described for SRS-A (Lewis, R. A., Drazen, J. M., Austen, K. F., Clark, D. A., and Corey, E. J., Biochemical and Biophysical Research Communications, 96: 271, 1980). Moreover, human lung fragments from patients with extrinsic asthma generate large amounts of leukotrienes when challenged in vitro (Lewis, R. A., Austen, K. F., Drazen, J. M., Clark, D. A., Marfat, A., and Corey, E. J., Proceedings of the National Academy of Sciences, USA, 77: 3710, 1980.) and synthetic leukotrienes are potent constrictors of human airway smooth muscle in vitro (Dahlen, S. E., Hansson, G., Hedqvist, P., Bjorck, T., Granstrom, E., and Dahlen, B., Proceedings of the National Academy of Sciences, USA, 80: 1712, 1983; Dahlen, S., Hedqvist, P., Hammarstrom, S., and Samuelsson, B., Nature, 288: 484, 1980). Aerosolized leukotrienes administered to normal human volunteers cause vigorous airway constriction (Hanna, C. J., Bach, M. K., Pare, P. D., and Schellenberg, R. R., Nature, 290: 343, 1981; Holroyde, M. C., Altounyan, R. E. C., Cole, M., Dixon, M., and Elliott, E. Y., The Lancet, 4: 17, 1981) and $LTC_4$ produces a preferential effect on the peripheral airways which is slow in onset and long in duration (Weiss, J. W., Drazen, J. M., Coles, N., McFadden, E. R., Jr., Weller, P. F., Corey, E. J., Lewis, R. A., and Austen, K.

F., Science, 216: 186, 1982). LTC4 levels were found to be elevated in the blood of children undergoing an acute asthmatic attack (Schwartsburg, S. B., Shelov, S. P., and Van Praag, D. Prostaglandins Leukotrienes and Medicine, 26: 143, 1987). Leukotrienes were also detected in sputum of patients with chronic bronchitis (Zakrezewski, J. T., Barnes, N. C., Piper, P. C., Costello, J. F. Prostaglandins, 33: 663, 1987). These pulmonary effects of LTC4 are characteristic of those observed in asthmatic patients following antigen inhalation and are consistent with a major role for leukotrienes in allergic asthma (Lewis, R. A., Chest, 87: 5S, 1985).

2. Allergic Rhinitis

Nasal challenge with specific antigen of patients with allergic rhinitis results in dose- and time-dependent elevations of leukotrienes in nasal washings (Shaw, R. J., Fitzharris, P., Cromwell, O., Wardlaw, A. J., and Kay, A. B., Allergy, 40: 1, 1985). Leukotrienes are proposed mediators of allergic rhinitis as they are stimulators of mucus secretion and vascular permeability (Schelhamer, J. H., Marom, Z., Sun, F., Bach, M. K., and Kaliner, M., Chest, 81 (Suppl): 36, 1982; Coles, S. J., Neill, K. H., Reid, L. M., Austen, K. F., Nii, Y., Corey, E. J., and Lewis, R. A., Prostaglandins, 25: 155, 1983; Soter, N. A., Lewis, R. A., Corey, E. J., and Austen, K. F., The Journal of Investigative Dermatology, 80: 115, 1983), characteristic events in the pathophysiology of this disorder.

3. Rheumatoid Arthritis And Gout

Both LTB$_4$ and 5-HETE stimulate polymorphonuclear leukocyte (PMNL) chemotaxis. LTB4 is one of the most potent chemotactic substances known (Smith, M. J. H., General Pharmacology, 12: 211, 1981). By virtue of their abilities to attract PMNL, these products may contribute to the observed accumulation of PMNL in synovial fluid of individuals with rheumatoid arthritis and gout. 5-HETE and LTB$_4$ have been identified in joint fluids from patients with rheumatoid arthritis (Klickstein, L. B., Shapleigh, C., and Goetzl, E. J., Journal of Clinical Investigation, 66: 1166, 1980; Davidson, E. M., Rae, S. E., and Smith, M. J. H., Journal of Pharmacy and Pharmacology, 34: 410, 1982) and particularly high concentrations of LTB$_4$ have been found in synovial fluids from patients with gout (Rae, S. A., Davidson, E. M., and Smith, M. J. H., The Lancet, 2: 1122, 1982).

4. Psoriasis

LTB$_4$ is present in higher than normal levels in psoriatic lesions (Brian, S. D., Camp, R., Dowd, P., Black, A., and Greaves, M., The Journal of Investigative Dermatology, 83: 70, 1984) which have significantly elevated 5-lipoxygenase activity compared to uninvolved or normal skin (Ziboh, V. A., Casebolt, T. L., Marcelo, C. L., and Voorhees, J. J., The Journal of Investigative Dermatology, 83: 425, 1984). The neutrophil infiltrate that characterizes the early stages of this disease may be due to the chemoattractant properties of LTB4 which can induce micropustule formation when applied topically (VandeKerkhof, P. C. M., Bauer, F. W., and deGroud, R. M., The Journal of Investigative Dermatology, 84: 450, 1985). LTC$_4$ and LTD$_4$ have also been detected in psoriatic skin lesions (Brian, S. D., Camp, R. D. R., Black, A. K., Dowd, P. M., Greaves, M. W., Ford-Hutchinson, A. W., and Charleson, S., Prostaglandins, 29: 611, 1985). These mediators act as vasodilators in human skin and may account for the vasodilation and increased blood flow in psoriatic lesions.

5. Adult Respiratory Distress Syndrome

The presence of elevated LTD$_4$ concentrations in pulmonary edema fluids has led to the suggestion that LTD$_4$ contributes to the permeability defect in the alveolar-capillary barrier in patients with adult respiratory distress syndrome (Matthay, M. A., Eschenbacher, W. L., and Goetzl, E. J., Journal of Clinical Immunology, 4: 479, 1984).

6. Inflammatory Bowel Disease

The colonic mucosa of patients with Crohn's disease has an increased capacity to synthesize sulfidopeptide leukotrienes compared to normal mucosa when exposed to the calcium ionophore A-23187 (Peskar, B. M., Dreyling, K. W., Hoppe, V., Schaarschmidt, K., Goebell, H., and Peskar, B. A., Gastroenterology, 88: 537, 1985). Elevated levels of 5-lipoxygenase products are found in colonic tissue from patients with inflammatory bowel disease; sulfasalazine, a drug used in the treatment of this disease, has been shown to be a weak 5-lipoxygenase inhibitor (Sharon, P. and Stenson, W. F., Gastroenterology, 86: 453, 1984). These observations suggest that increased leukotriene formation may contribute to the characteristic mucosal inflammation of this disorder.

7. Endotoxin Shock.

Leukotrienes elicit many of the pathophysiologic symptoms observed in endotoxin shock, such as cardiac depression, increased vascular permeability leading to tissue edema, and increased leukocyte adhesion to endothelial surfaces (Hagmann, W., Denzlinger, C., and Keppler, D. Production of peptide leukotrienes in endotoxin-shock. FEBS Letters, 180: 309, 1985). Furthermore, endotoxins have been shown to trigger the formation of leukotrienes. It has therefore been proposed that leukotrienes play a key role in the lethal action of endotoxin (Konig, W., Scheffer, J. Bremm, K. D., Hacker, J., and Goebel, W., International Archives of Allergy and Applied Immunology, 77: 118, 1985).

8. Ischemia-induced Myocardial Injury.

The leukotrienes are potent constrictors of coronary arteries and may play a role in regulating blood flow to the heart. LTC$_4$ and LTD$_4$ exacerbate ischemia-induced myocardial injury in rabbits (Lefer, A. M. Eicosanoids as Mediators of Ischemia and Shock. Federation Proceedings, 44: 275, 1985). Furthermore, infarcted hearts, when reperfused, release larger quantities of leukotrienes in response to stimuli than hearts from sham-operated animals (Barst, S. and Mullane, K., Clinical Research, 33: A516, 1985). These results implicate leukotrienes as potential mediators of ischemia.

9. Central Nervous Pathophysiology.

Leukotrienes are synthesized in greater amounts in gerbil forebrains after ischemia and reperfusion (Moskowitz, M. A., Kiwak, K. J., Hekimian, K., et al., Science, 224: 886, 1984), concussive injury, or subarachnoid hemorrhage (subarachnoid injection of blood) (Kiwak, K. J., Moskowitz, M. A., and Levine, L., Journal of Neurosurgery, 62: 865, 1985). The formation of leukotrienes is temporally associated with the cerebral vasospasm and other abnormalities resulting from the insult. Thus a possible role can be suggested for leukotrienes in the pathophysiology resulting from stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Agents capable of abrogating the effects of these potent mediators of pathophysiological processes represent a promising class of therapeutic agents (Brooks, D. W., Bell, R. L., and Carter, G. W. Chapter 8. Pulmonary and Antiallergy Agents, Annual Reports in Medicinal Chemistry, Allen, R. C. ed., Academic Press 1988.

SUMMARY OF THE INVENTION

The compounds of this invention possess activity as inhibitors of 5- and/or 12-lipoxygenase and reduce the biosynthesis of leukotrienes $LTB_4$, $LTC_4$, $LTD_4$ and $LTE_4$. The compounds and compositions containing these compounds are useful for the treatment of disease states in mammals which involve lipoxygenase enzymes or which involve the leukotrienes $LTB_4$, $LTC_4$, $LTD_4$ and $LTE_4$.

The novel compounds of this invention are the compounds of Formula I:

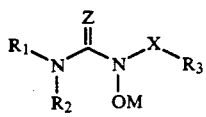

I or a pharmaceutically acceptable salt thereof, where Z is oxygen or sulfur,.

X is selected from alkylene of from one to six carbon atoms; alkenylene of from two to six carbon atoms; and alkylene of from one to six carbon atoms or alkenylene of from two to six carbon atoms substituted by a group selected from hydroxy, halo, cyano, alkoxy, aminocarbonyl, alkylaminocarbonyl, dialkylaminocarbonyl, carboxy and alkoxycarbonyl.

$R^1$ and $R^2$ are independently selected from hydrogen; hydroxy; alkyl of from one to six carbon atoms; alkyl of from one to six carbon atoms substituted with a substituent selected from hydroxy, halo, cyano, alkoxy, alkylthio, aminocarbonyl, alkylaminocarbonyl, dialkylaminocarbonyl, carboxy and alkoxycarbonyl; carbocyclic aryl; and carbocyclic aryl substituted with a substituent selected from hydroxy, halo, cyano, alkoxy, alkylthio, amino, alkylamino, dialkylamino, aminocarbonyl, alkylaminocarbonyl, dialkylaminocarbonyl, carboxy and alkoxycarbonyl; with the proviso that $R^1$ and $R^2$ are not simultaneously hydroxy.

$R^3$ is selected from the group consisting of phenyl; naphthyl; thienyl; and phenyl, naphthyl, or thienyl substituted by alkyl of from one to six carbon atoms, alkenyl of from two to six carbon atoms, cycloalkyl of from three to ten carbon atoms, alkoxy of from one to six carbon atoms, alkylthio of from one to six carbon atoms, halo, nitro, hydroxy; carbocyclic or heterocyclic aryl; carbocyclic or heterocyclic aryloxy; carbocyclic or heterocyclic aroyl; carbocyclic or heterocyclic arylalkyl wherein the alkyl portion contains from one to six carbon atoms, carbocyclic or heterocyclic arylalkenyl wherein the alkenyl portion contains from two to six carbon atoms, carbocyclic or heterocyclic arylalkynyl wherein the alkynyl portion contains from two to six carbon atoms, carbocyclic or heterocyclic arylalkoxy wherein the alkoxy portion contains from one to six carbon atoms, carbocyclic or heterocyclic arylalkylthio wherein the alkylthio portion contains from one to six carbon atoms. In addition, the foregoing carbocyclic or heterocyclic aryl; carbocyclic or heterocyclic aryloxy; carbocyclic or heterocyclic aroyl; carbocyclic or heterocyclic arylalkyl, carbocyclic or heterocyclic arylalkenyl, carbocyclic or heterocyclic arylalkynyl, carbocyclic or heterocyclic arylalkoxy, and carbocyclic or heterocyclic arylalkylthio groups may be optionally substituted by one, two, or three groups independently selected from the group consisting of halo, nitro, cyano, alkyl, alkoxy, and halosubstituted alkyl.

M is selected from the group consisting of hydrogen; a pharmaceutically acceptable cation; a metabolically cleavable group, carbocyclic aroyl; $—Si(R^5)_3$ wherein $R^5$ is independently selected at each occurrence from alkyl of from one to six carbon atoms; $—C(O)R_4$; $—CH_2OR_4$; $—C(O)N(R^4)_2$ or $—C(O)OR^4$ wherein $R^4$ is alkyl of one to six carbon atoms.

DETAILED DESCRIPTION

While, in the compounds of this invention, the group M can be hydrogen, a suitable cation, or a group capable of being metabolically cleaved in vivo, in preferred compounds of the present invention M is hydrogen.

Similarly, while $R^3$ may be substituted or unsubstituted phenyl, naphthyl or thienyl, preferred compounds of the present invention are those in which $R^3$ is substituted or unsubstituted thienyl.

Examples of compounds which are within the scope of the present invention and/or can be used according to the methods of the present invention include, but are not limited to, the following:

N-hydroxy-N-(1-(4-butoxyphenyl)ethyl) urea
N-hydroxy-N-(1-(3-butoxyphenyl)ethyl) urea
N-hydroxy-N-(1-(4-(methylpropyl)phenyl)ethyl) urea
N-hydroxy-N-(1-(4-cyclohexyl)phenyl)ethyl) urea
N-hydroxy-N-(2-(4-butoxyphenyl)ethyl) urea
N-hydroxy-N-(1-methyl-2-(4-butoxyphenyl)ethyl) urea
N-hydroxy-N-(3-(4-butoxyphenyl)propyl) urea
N-hydroxy-N-(1-methyl-3-(4-butoxyphenyl)propyl) urea
N-hydroxy-N-(1-methyl-1-(4-butoxyphenyl)ethyl) urea
N-hydroxy-N-(1-(4-butoxyphenyl)-2-methylpropyl) urea
N-hydroxy-N-(3-nitro-4-butoxyphenylmethyl) urea
N-hydroxy-N-(1-(4-(2,4,6-trimethylphenyl)phenyl) ethyl urea
N-hydroxy-N-(1-(3-benzoylphenyl)ethyl) urea
N-hydroxy-N-(1-(4-(2-phenylethenyl)phenyl)ethyl) urea
N-hydroxy-N-(1-(4-(2-phenylethyl)phenyl)ethyl) urea
N-hydroxy-N-1-(4-bromophenyl)ethylurea
N-hydroxy-N-1-(4-bromophenyl)ethyl-N'-methyl-urea.
N-hydroxy-N-1-(4-bromophenyl)ethyl-N'-(2-hydroxyethyl)-urea.
N-hydroxy-N-4-bromobenzylurea.
N-hydroxy-N-4-bromobenzyl-N'-methyl urea
N-hydroxy-N-(1-(4-bromophenyl)propyl) urea
N-hydroxy-N-(1-(4-bromophenyl)propyl)-N'-methylurea
N-hydroxy-N-(1-(2,4-difluorophenyl)ethyl)-N'-methylurea
N-hydroxy-N-(1-(4-(2-phenylethynyl)phenyl)ethyl) urea
N-hydroxy-N-(1-(4-(2-phenylethynyl)phenyl)ethyl)-N'-methyl urea
N-hydroxy-N-(1-(4-chlorophenyl)ethyl) urea
N-hydroxy-N-(1-(4-chlorophenyl)ethyl)-N'-methyl urea
N-hydroxy-N-(1-(4-fluorophenyl)ethyl) urea
N-hydroxy-N-(1-(4-fluorophenyl)ethyl)-N'-methyl urea
N-hydroxy-N-(1-(4-trifluoromethylphenyl)ethyl) urea N-hydroxy-N-(1-(4-trifluoromethylphenyl)ethyl)-N'-methyl urea
N-hydroxy-N-(1-(4-methylphenyl)ethyl) urea
N-hydroxy-N-(1-(3-bromo-4-fluorophenyl)ethyl)-N'-methyl urea
N-hydroxy-N-(1-(3-bromo-4-methylphenyl)ethyl)-N'-methyl urea
N-hydroxy-N-(1-(4-methoxyphenyl)ethyl) urea
N-hydroxy-N-(1-(4-methoxyphenyl)ethyl)-N'-methyl urea
N-hydroxy-N-(1-(4-phenoxyphenyl)ethyl) urea
N-hydroxy-N-(1-(4-butoxyphenyl)ethyl) urea
N-hydroxy-N-(1-(4-biphenyl)ethyl) urea
N-hydroxy-N-(1-(4-bis-allylaminophenyl) ethyl) urea
N-hydroxy-N-(1-(3-bromo-4-fluorophenyl) ethyl) urea
N-hydroxy-N-(1-(4-chloro-3-methylphenyl) ethyl) urea
N-hydroxy-N-(1-(4-chloro-3-methylphenyl) ethyl)-N'-methyl urea
N-hydroxy-N-(1-(4-chloro-3-methylphenyl) ethyl) urea
N-hydroxy-N-(4-methoxyphenyl)-N'-methyl urea
N-hydroxy-N-(1-(4-phenylmethoxyphenyl) ethyl) urea
N-hydroxy-N-1-(4-phenylmethoxyphenyl) ethyl N'-methyl urea
N-hydroxy-N-1-(4-phenylmethoxyphenyl) ethyl N'N'-dimethyl urea
N,N'-dihydroxy-N-(1-(4-phenylmethoxyphenyl) ethyl urea
N-hydroxy-N-(4-phenylmethoxyphenylmethyl) urea
N-hydroxy-N-(4-phenylmethoxyphenylmethyl)-N'-methyl-urea
N-hydroxy-N-(1-(4-phenylmethoxy-3,5-dimethoxyphenyl)-ethyl) urea
N-hydroxy-N-(1-(4-(2-phenyl)ethoxyphenyl)ethyl) urea
N-hydroxy-N-(1-(4-phenoxyphenyl)ethyl) urea
N-hydroxy-N-(1-(4-(4-fluorophenylmethoxy) phenyl)ethyl) urea
N-hydroxy-N-(1-(4-(4-methoxyphenylmethoxy)phenyl) ethyl) urea
N-hydroxy-N-(1-(4-(4-trifluoromethylphenyl methoxy)-phenyl)ethyl) urea
N-hydroxy-N-(1-(4-phenylmethoxy-3,5-dichlorophenyl)ethyl) urea
N-hydroxy-N-(2-hydroxy-4-phenylmethoxyphenylmethyl) urea
N-hydroxy-N-(1-(4-phenylthiomethoxyphenyl)ethyl urea
N-hydroxy-(1-(4-phenylmethoxyphenyl)ethyl) urea sodium salt
N-hydroxy-(1-(4-phenylmethoxyphenyl)ethyl) urea potassium salt
N-hydroxy-(1-(4-phenylmethoxyphenyl)ethyl) urea ammonium salt
N-hydroxy-(1-(4-phenylmethoxyphenyl)ethyl) urea triethylammonium salt
N-hydroxy-(1-(4-phenylmethoxyphenyl)ethyl) urea tetraethyl ammonium salt
N-butyryloxy-(1-(4-phenylmethoxyphenyl)ethyl) urea
N-benzoyloxy-(1-(4-phenylmethoxyphenyl)ethyl) urea
N-hydroxy-N-(1-(2-naphthyl)ethyl) urea
N-hydroxy-N-(1-(6-butoxy-2-naphthyl)ethyl) urea
N-hydroxy-N-(1-(6-phenylmethoxy-2-naphthyl)ethyl) urea
N-hydroxy-N-(1-(6-methoxynaphthalen-2-yl)ethyl) urea
N-hydroxy-N-((6-methoxynaphthalen-2-yl)methyl) urea
N-hydroxy-N-(3-(6-methoxynaphthalen-2-yl)propen-1-yl) urea
N,N'-dihydroxy-N-(1-(2-naphthyl)ethyl) urea
N-hydroxy-N-1-(5-methylthien-2-yl)ethyl urea.
N-hydroxy-N-(thien-2-yl)methyl urea
N-hydroxy-N-1-(3-methylthien-2-yl)ethyl urea
N-hydroxy-N-(1-(5-pyrid-2-yl)thien-2-yl)ethyl urea
N-hydroxy-N-(1-thien-2-yl)ethyl urea
N-hydroxy-N-(3-methylthien-2-yl)methyl urea
N-hydroxy-N-(thien-2-yl)methyl-N'-methyl urea
N-hydroxy-N-(5-methylthien-2-yl)methyl urea
N-hydroxy-N-1-(5-methylthien-2-yl)methyl-N'-methyl urea
N-hydroxy-N-(1-(5-phenylthien-2-yl)methyl) urea
N-hydroxy-N-(1-(5-phenylthien-2-yl)methyl)-N'-methyl urea
N-hydroxy-N-(1-(5-(pyrid-2-yl)thien-2-yl)methyl) urea
N-hydroxy-N-(1-(5-phenylthien-2-yl)ethyl) urea
N-hydroxy-N-(1-(5-benzylthien-2-yl)ethyl) urea
N-hydroxy-N-(1-(5-(2-phenylethenyl)thien-2-yl)ethyl) urea
N-hydroxy-N-(1-(1-(5-methylthien-2-yl)-2-hydroxy)ethyl) urea
N-hydroxy-N-(1-(5-methylthien-2-yl)-5-carboethoxypentyl) urea
N-hydroxy-N-(1-(5-methylthien-2-yl)-6-carboxyamidohexyl) urea
N-hydroxy-N-(1-(1-(2-hydroxy))-5-methylthien-2-yl)propyl) urea
N'-methyl-N-hydroxy-N-(1-(1-(2-hydroxy))-5-(methylthien-2-yl)ethyl) urea
N-hydroxy-N-1-(2,5-dimethylthien-3-yl)ethyl urea
N-hydroxy-N-1-(thien-3-yl)ethyl urea
N-hydroxy-N-(thien-3-yl)methyl urea
N-hydroxy-N-(1-(2,5-dimethylthien-3-yl)ethyl)-N'-methylethoxycarbonyl urea
N-hydroxy-N-(1-(2,5-dimethylthien-3-yl)ethyl)-N'-(2-hydroxyethyl) urea
N-hydroxy-N-(1-thien-3-ylethyl)-N'-1-(4-carbomethoxybutyl) urea
N-hydroxy-N-(1-thien-3-ylethyl-N'-(methylethoxycarbonyl) urea
N-hydroxy-N-(3-(1-thien-3-yl)propenyl) urea
N-hydroxy-N-(3-(1-thien-3-yl)propyl)urea
N-hydroxy-N-(1-thien-3-ylethyl)thiourea
N-hydroxy-N-[1-(5-methylthien-2-yl)ethyl]thiourea
N-hydroxy-N-(2-(1-(5-methylthien-2-yl))propyl)urea
N-hydroxy-N-4-(4,5,6,7-tetrahydrothianaphthalene)urea
N-hydroxy-N-[(4-bromothien-3-yl)methyl]urea
N-hydroxy-N-[1-(thien-3-yl)propen-2-yl]urea
N-hydroxy-N-(1-(5-(2-thien-2-ylethenyl)thien-2-yl)ethyl)-urea
N-hydroxy-N-(1-(5-(2-pyrid-2-ylethenyl)thien-2-yl)ethyl)-urea
N-hydroxy-N-(1-(5-(2-thien-3-ylethenyl)thien-2-yl)ethyl)-urea
N-hydroxy-N-(1-(5-(4-chlorophenylethen-2-yl)thien-2-yl)-ethyl)urea
N-hydroxy-N-(2-(1-thien-3-yl)propyl)urea
N-hydroxy-N-(2-(1-thien-2-yl)propyl)urea
N-hydroxy-N-(2-(1-(5-pyrid-2-yl)thien-2-yl)propyl)urea
N-hydroxy-N-(2-(1-(5-phenylethen-2-yl)propyl)-urea
N-hydroxy-N-(2-(1-(5-benzylthien-2-yl)propyl)urea
N-hydroxy-N-(thien-3-yl)methyl urea potassium salt
N-hydroxy-N-(3-(1-thien-3-yl)propenyl)urea potassium salt
N-ethoxycarbonyloxy-N-(thien-3-yl)methy urea
N-ethoxycarbonyloxy-N-(3-(1-thien-3-yl)propenyl)urea N-trimethylsilyloxy-N-(thien-3-yl)methyl urea
N-hydroxy-N-(thien-3-yl)methyl-N'-phenyl urea
N,N'-dihydroxy-N-(thien-3-yl)methyl-N'-methyl urea
N,N'-dihydroxy-N-1-(thien-3-yl)ethyl-N'-methyl urea
N,N'-dihydroxy-N-1-(5-phenylthien-2-yl)ethyl urea
N-hydroxy-N-(3-bromothien-2-yl)methyl urea
N-hydroxy-N-(4-bromothien-2-yl)methyl urea
N-hydroxy-N-(5-chlorothien-2-yl)methyl urea
N-hydroxy-N-(5-bromothien-2-yl)methyl urea
N-hydroxy-N-(5-bromothien-2-yl)methyl acetamide
N-hydroxy-N-[1-(4-bromothien-2-yl)ethyl]urea
N-hydroxy-N-[1-(5-bromothien-2-yl)ethyl]urea
N-hydroxy-N-[3-(phenylthio)thien-2-yl]methyl urea
N-hydroxy-N-[5-(phenylthio)thien-2-yl]methyl urea
N-hydroxy-N-[4-(phenylthio)thien-2-yl]methyl urea
N-hydroxy-N-[5-(phenylthio)thien-3-yl]methyl urea
N-hydroxy-N-[2-(phenylthio)thien-3-yl]methyl urea
N-hydroxy-N-{1-[5-(phenylthio)-thien-2-yl]ethyl}urea
N-hydroxy-N-[3-(4-hydroxyphenylthio)thien-2-yl]methyl urea
N-hydroxy-N-[3-(4-bromophenylthio)thien-2-yl]methyl urea
N-hydroxy-N-[3-(4-chlorophenylthio)thien-2-yl]methyl urea
N-hydroxy-N-[3-(4-fluorophenylthio)thien-2-yl]methyl urea
N-hydroxy-N-[3-(4-tertbutylphenylthio)thien-2-yl]methyl urea
N-hydroxy-N-[3-(2-pyridylthio)thien-2-yl]methyl urea
N-hydroxy-N-[3-(2-furfurylmethylthio)thien-2-yl]methyl urea
N-hydroxy-N-[3-tert-butylthio)thien-2-yl]methyl urea
N-hydroxy-N-[5-(tert-butylthio)thien-2-yl]methyl urea
N-hydroxy-N-[1-(5-{tert-butylthio}thien-2-yl)ethyl]urea
N-hydroxy-N-[5-(iso-propylthio)thien-2-yl]methyl urea
N-hydroxy-N-[1-(5-{methylthio}thien-2-yl)ethyl]urea
N-hydroxy-N-3-[5-(phenylthio)thien-2-yl]propenyl urea
N-hydroxy-N-(3-[5-(phenylthio)thien-2-yl]butenyl urea
N-hydroxy-N-3-[5(tert-butylthio)thien-2-yl]propenyl urea
N-hydroxy-N-[5-(phenoxy)thien-2-yl]methyl urea
N-hydroxy-N-[3-(phenoxy)thien-2-yl]methyl urea
N-hydroxy-N-[4-(phenoxy)thien-2-yl]methyl urea
N-hydroxy-N-[4-(4-chlorophenoxy)thien-2-yl]methyl urea Preferred compounds of the invention include, but are not limited to, the following:
N-hydroxy-N-1-(4-bromophenyl)ethylurea
N-hydroxy-N-(1-(4-chlorophenyl)ethyl)urea
N-hydroxy-N-(5-bromothien-2-yl)methyl urea
N-hydroxy-N-[1-(5-bromothien-2-yl)ethyl]urea
N-hydroxy-N-[3-(phenylthio)thien-2-yl]methyl urea
N-hydroxy-N-[5-(phenylthio)thien-2-yl]methyl urea
N-hydroxy-N-[4-(phenylthio)thien-2-yl]methyl urea
N-hydroxy-N-[5-(phenylthio)thien-3-yl]methyl urea
N-hydroxy-N-[2-(phenylthio)thien-3-yl]methyl urea The term "alkylene" as used herein refers to a divalent straight or branched chain group of from one to six carbon atoms including, but not limited to, —CH$_2$—, —(CH$_2$)$_2$—, —(CH$_2$)$_3$—, —CH(CH$_3$)—, —CH(C$_2$H$_5$)—, —CH(CH$_3$)CH$_2$—, and the like.

The term "alkenyl" as used herein refers to a monovalent straight or branched chain radical of from two to six carbon atoms containing a carbon-carbon-double bond including, but not limited to, 1-propenyl, 2-propenyl, 2-methyl-1-propenyl, 1-butenyl, 2-butenyl and the like.

The term "alkenylene" as used herein refers to a divalent straight or branched chain group of from two to six carbon atoms containing a carbon-carbon double bond, including, but not limited to —CH=CH—, —C(CH3)=CH—, —CH=CH—CH$_2$—, —CH=C(CH$_3$)—CH$_2$—, —CH2CH(CH=CH$_2$)CH$_2$—and the like.

The term "cycloalkyl" as used herein refers to monovalent saturated cyclic radicals, preferably of three to eight carbon atoms, including, but not limited to cyclopropyl, cyclobutyl, cyclopentyl, cyclohexyl, and the like.

The terms "alkoxy" and "alkylthio" as used herein refer to alkyl groups as defined above, linked to the parent molecular moiety through an oxygen atom or a sulfur atom, respectively. Alkoxy and alkylthio groups include, for example, methoxy, ethoxy, isopropoxy, n-butoxy, sec-butoxy, isobutoxy, tert-butoxy, and the like, or the corresponding sulfur analogues.

The term "alkylamino" as used herein refers to a monovalent group of the formula —NH-alkyl where alkyl is as defined above.

The term "dialkylamino" as used herein refers to a group of the formula —N(alkyl)(alkyl) where the two alkyl groups are as defined above and may be the same or different.

The term "aminocarbonyl" as used herein refers to a group of the formula —C(O)NH$_2$.

The term "alkylaminocarbonyl" as used herein refers to a group of the formula —C(O)NH(alkyl) where alkyl is as defined above.

The term "dialkylaminocarbonyl" as used herein refers to a group of the formula —C(O)N(alkyl)(alkyl) where the two alkyl groups are as defined above and may be the same or different.

The term "carboxyl" refers to—COOH.

The term "alkoxycarbonyl" as used herein refers to an ester group of the formula —C(O)O(alkyl) where alkyl is as defined above.

N-hydroxy-N-[1-(5-(phenylthio)-thien-2-yl)ethyl]urea
N-hydroxy-N-[3-(4-chlorophenylthio)thien-2-yl]methyl urea
N-hydroxy-N-[3-(2-pyridylthio)thien-2-yl]methyl urea
N-hydroxy-N-3-[5-(phenylthio)thien-2-yl]propenyl urea
N-hydroxy-N-(3-[5-(phenylthio)thien-2-yl]butenyl urea
N-hydroxy-N-[4-(phenoxy)thien-2-yl]methyl urea
N-hydroxy-N-[4-(4-chlorophenoxy)thien-2-yl]methyl urea
N-hydroxy-N-1-(5-methylthien-2-yl)ethyl urea;
N-hydroxy-N-(1-thien-2-yl)ethyl urea;
N-hydroxy-N-(1-(5-pyrid-2-yl)thien-2-yl)ethyl urea;
N-hydroxy-N-(3-methylthien-2-yl)methyl urea;
N-hydroxy-N-(1-(5-phenylthien-2-yl)methyl) urea;
N-hydroxy-N-(1-(5-phenyl-thien-2-yl)methyl-N'-methyl urea;
N-hydroxy-N-(1-(5-(pyrid-2-yl)thien-2-yl)methyl) urea;
N-hydroxy-N-(1-(5-phenylthien-2-yl)ethyl) urea;
N-hydroxy-N-(3-(1-thien-3-yl)propyl) urea;
N-hydroxy-N-(1-thien-3-ylethyl) thiourea;
N-hydroxy-N-(2-(1-(5-methylthien-2-yl)propyl) urea;
N-hydroxy-N-1-(thien-3-yl)ethyl urea;
N-hydroxy-N-(thien-3-yl)methyl urea;
N-hydroxy-N-(thien-2-yl)methyl urea; and
N-hydroxy-N-(3-(1-thien-3-yl)propenyl) urea.
N-hydroxy-N-1-(thien-3-yl)ethyl urea;

N-hydroxy-N-(thien-3-yl)methyl urea;
N-hydroxy-N-(thien-2-yl)methyl urea; and
N-hydroxy-N-(3-(1-thien-3-yl)propenyl) urea.

The term "alkyl" as used herein refers to a monovalent straight or branched chain radical of from one to six carbon atoms, including, but not limited to methyl, ethyl, n-propyl, isopropyl, n-butyl, sec-butyl, isobutyl, tert-butyl, n-hexyl and the like.

The term "halosubstituted alkyl" as used herein refers to an alkyl group as just defined, substituted by one, two, or three halogen atoms selected from fluorine, chlorine and bromine. Examples of such groups include chloromethyl, bromoethyl, trifluoromethyl, and the like.

The term "alkanoyl" as used herein refers to—C(O)H or—C(O)alkyl where alkyl is as defined above. Examples of alkanoyl groups include, but are not limited to formyl, acetyl, propionyl, butyryl, isobutyryl, pivaloyl, and the like.

The term "carbocyclic aryl" as used herein refers to a monovalent substituted or unsubstituted aromatic radical comprising a single ring of carbon atoms or two or three fused rings of carbon atoms including, but not limited to, phenyl, 1- or 2-naphthyl, 1-, 2-, or 9-anthracyl, and the like. Substituted carbocyclic aryl groups are groups as just defined, substituted with one or two substituents independently selected from hydroxy, halo, alkoxy, alkylthio, alkyl, nitro, amino, alkylamino, dialkylamino, haloalkyl, cyano, carboxy, alkoxycarbonyl, aminocarbonyl, alkylaminocarbonyl and dialkylaminocarbonyl.

The term "heterocyclic aryl" refers to a monovalent 5- or 6-membered substituted or unsubstituted aromatic radical containing one nitrogen, oxygen, or sulfur atom, one nitrogen and one oxygen atom, one nitrogen and one sulfur atom, or one, two, or three nitrogen atoms. "Heterocyclic aryl" is also meant to include 5- or 6-membered ring systems as just defined, fused to a benzene ring. Specifically, as used herein, the term heterocyclic aryl refers to substituted or unsubstituted furyl, benzofuranyl, thienyl, benzo[b]thienyl, pyridyl, indolyl, quinolyl, thiazolyl, benzothiazolyl, and pyrimidyl. Substituted heterocyclic aryl groups are heterocyclic aryl groups as just defined, substituted with one or two substitutents independently selected from hydroxy, halo, alkoxy, alkylthio, alkyl of from one to six carbon atoms, nitro, amino, alkylamino, dialkylamino, haloalkyl, cyano, carboxy, alkoxycarbonyl, aminocarbonyl, alkylaminocarbonyl and dialkylaminocarbonyl.

The term "carbocyclic arylalkyl" as used herein refers to a carbocyclic aryl group as defined above, attached to the parent molecular moiety through an alkylene group of from one to six carbon atoms including, but not limited to, substituted or unsubstituted phenylmethyl (benzyl), 1-phenylethyl, 2-phenylethyl, 1-naphthylmethyl, 2-naphthylmethyl groups and the like.

The term "heterocyclic arylalkyl" as used herein refers to a heterocyclic aryl group as defined above, attached to the parent molecular moiety through an alkylene group of from one to six carbon atoms including, but not limited to, as used herein refers to a heterocyclic aryl group as defined above, attached to the parent molecular moiety through an alkylene group of from one to six carbon atoms including, but not limited to substituted or unsubstituted 2-, 3-, or 4-pyridylmethyl, 2- or 3-thienylmethyl, 2- or 3-furanylmethyl, 2-, 3-, or 4-quinolylmethyl groups and the like.

The term "carbocyclic arylalkenyl" as used herein refers to a carbocyclic aryl group, as defined above, attached to the parent molecular moiety through a straight or branched alkenylene group of from two to six carbon atoms. Such groups include, for example, phenylethenyl, 3-phenylpropen-1-yl, 3-phenylpropen-2-yl, 1-naphthylethenyl, and the like.

The term "heterocyclic arylalkenyl similarly refers to a heterocyclic aryl group as defined above attached to the parent molecular moiety through a straight or branched alkenylene group of from two to six carbon atoms. Such groups are exemplified by 3-(pyrid-3-yl)propen-1-yl, 2-(thien-2-yl)ethenyl and the like.

The term "carbocyclic arylalkynyl" as used herein refers to a carbocyclic aryl group as defined above, attached to the parent molecular moiety through a divalent straight or branched chain hydrocarbon group of from two to six carbon atoms containing one carbon-carbon triple bond. Such groups include, for example substituted and unsubstituted phenylethynyl, 3-phenylpropyn-1-yl, 1or 2-naphthylethynyl, and the like.

The terms "carbocyclic aryloxy" and "carbocyclic arylthio" as used herein refer to a carbocyclic aryl group as defined above, attached to the parent molecular moiety through an oxygen or sulfur atom, respectively. Such groups include, for example, substituted or unsubstituted phenoxy, 1-naphthoxy, 2-naphthoxy groups, the sulfur analogues, and the like.

The terms "heterocyclic aryloxy" and "heterocyclic arylthio" as used herein refer to a heterocyclic aryl group as defined above, attached to the parent molecular moiety through an oxygen or sulfur atom, respectively. Such groups include 2-, 3-, or 4-pyridyloxy, 2- or 3-thienyloxy, 2-, 3-, or 4-pyridylthio, and the like.

The terms "carbocyclic arylalkoxy" and "carbocyclic arylalkylthio" as used herein refer to monovalent radicals in which a carbocyclic arylalkyl group, as defined above, is attached to the parent molecular moiety through an oxygen or sulfur atom, respectively. Such groups include, for example, phenylmethoxy (i.e., benzyloxy), 1-phenylethoxy, 2-phenylethoxy, 1-naphthylmethyloxy, 2-napthylmethyloxy and the like.

The terms "heterocyclic arylalkoxy" and "heterocyclic arylalkylthio" as used herein refer to a heterocyclic arylalkyl group as defined above, attached to the parent molecular moiety through an oxygen or sulfur atom, respectively. Such groups include, for example 2-, 3-, or 4-pyridylmethoxy, 2-, 3-, or 4-pyridylmethylthio, 2- or 3-thienylmethoxy, 2- or 3-thienylmethylthio, and the like.

The term "carbocyclic aroyl" as used herein refers to —C(O)—(carbocyclic aryl) where carbocyclic aryl is as defined above. Carbocyclic aroyl groups include, for example, substituted and unsubstituted benzoyl, 1- or 2-naphthoyl and the like.

The terms "halo" and "halogen" as used herein refer to radicals derived from the elements fluorine, chlorine, bromine, and iodine.

The term "halosubstituted alkyl" and "haloalkyl" as used herein refer to an alkyl group, as defined above, in which one to three hydrogen atoms are substituted by a halogen, including, but not limited to, chloromethyl, trifluoromethyl, 2,2,2-trichloroethyl, and the like.

As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups reactive with the N-hydroxy group of the compounds of this invention (where Z is hydrogen) well known to practitioners of the art. They include, but are not limited to such groups as alkanoyl (such as acetyl, propionyl, butyryl and the like), unsubstituted and substituted aroyl (such as benzoyl and substituted benzoyl), alkoxycarbonyl (such as ethoxycarbonyl), trialkylsilyl (such as trimethyl- and triethylsilyl), monoesters formed with dicarboxylic acids (such as succinyl), and the like. Because of the ease with which the metabolically cleavable groups of the compounds of this invention are cleaved in vivo, the compounds bearing such groups act as pro-drugs of other lipoxygenase inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

In those instances where the compounds of the present invention possess an acidic functional substituent such as carboxyl, the compounds are capable of forming base addition salts. In such instances, the term "pharmaceutically acceptable salts" refers to the relatively nontoxic, inorganic and organic base addition salts of compounds of the present invention. These salts can be prepared in situ during the final isolation and purification of the compounds or by separately reacting the purified N-hydroxy urea compound with a suitable base such as the hydroxide, carbonate or bicarbonate of a pharmaceutically acceptable metal cation or with ammonia, or an organic primary, secondary, or tertiary amine of sufficient basicity to form a salt with the N-hydroxy functional group of the compounds of this invention.

Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine, and the like. (See, for example S. M. Berge, et al., "Pharmaceutical Salts," *J. Pharm. Sci.*, 66: 1–19 (1977) which is incorporated herein by reference.)

Similarly, in those instances where the compounds of the present invention comprise a basic substituent such as an amino, alkylamino, or dialkylamino group, the compounds are capable of forming acid addition salts. In such cases, the term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts," *J. Pharm. Sci.*, 66: 1–19 (1977) which is incorporated herein by reference.)

The term "pharmaceutically acceptable cation" refers to non-toxic cations including but not limited to those based on the alkali and alkaline earth metals, such as sodium, lithium, potassium, magnesium, aluminum and the like, as well as nontoxic ammonium, quaternary ammonium, and amine cations, derived from nitrogenous bases of sufficient basicity to form salts with the N-hydroxy group of the compounds of this invention.

Certain compounds possess one or more chiral centers and may thus exist in optically active forms. Likewise, when the compounds contain an alkenyl or alkenylene group, there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

METHOD OF TREATMENT

This invention provides a method of treatment of inhibiting 5- and/or 12-lipoxygenase activity in a human or lower mammal host in need of such treatment, which method comprises administration to the human or lower mammal host of a compound previously described in an amount effective to inhibit lipoxygenase activity in the host. The compounds of the present invention may be administered orally, parenterally or topically in dosage unit formulations containing conventional nontoxic pharmaceutically acceptable carriers, adjuvants and vehicles are desired.

The term parenteral as used herein includes subcutaneous, intravenous, intraarterial injection or infusion techniques, without limitation. The term "topically" encompasses administration rectally and by inhalation spray, as well as by the more common routes of the skin and the mucous membranes of the mouth and nose.

Actual dosage levels of active ingredients in the pharmaceutical compositions of this invention may be varied so as to administer an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved. If desired, the effective daily dose may be divided into multiple doses for purposes of administration, e.g. two to four separate doses per day.

Total daily dose of the compounds of this invention administered to a host in single or divided doses may be in amounts, for example, of from about 0.001 to about 100 mg/kg body weight daily and more usually 0.01 to 10 mg/kg/day. Dosage unit compositions may contain such amounts of such submultiples thereof as may be used to make up the daily dose.

It will be understood, however, that the specific dose level for any particular patient will depend upon a variety of factors including the body weight, general health, sex, diet, time and route of administration, rates of absorption and excretion, combination with other drugs and the severity of the particular disease being treated.

FORMULATION OF PHARMACEUTICAL COMPOSITIONS

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

SYNTHESIS OF THE COMPOUNDS

Compounds of this invention can be prepared according to the reaction sequence described in Scheme 1. Although the sequence illustrates the compound of formula I where $R^1$, $R^2$, $Y^1$ and $Y^2$ are hydrogen, X is $CHCH_3$, and $R^3$ is phenyl, it will be seen from the examples that other compounds of this invention can be prepared in the same manner using the appropriate starting materials.

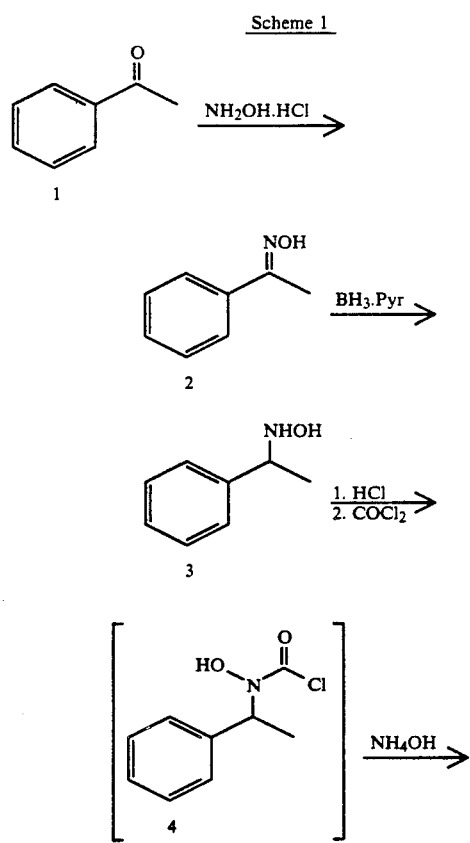

Scheme 1

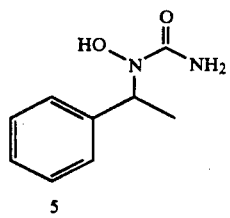

-continued
Scheme 1

Referring to reaction Scheme 1, acetophenone, 1, is treated with hydroxylamine in ethanol/pyridine to produce the oxime, 2. This is reduced to the hydroxylamine, 3, with borane pyridine complex and then converted to the hydrochloride salt with HCl gas. Treatment with phosgene yields carbamoyl chloride, 4, which is reacted without isolation to yield the urea, 5. Other reagents may also be used to carry out the same transformations. For example the oxime, 2, may be converted to the corresponding hydroxylamine, 3, using borane dimethylamine or other borane amine complexes or with sodium cyanoborohydride.

Compounds of formula I can also be prepared according to Scheme 2, below. The sequence illustrates the case where $R^1$, $R^2$, $Y^1$ and $Y^2$ are hydrogen and where $R^2$ is phenyl and X is $CH(CH_3)$, however it will be seen from the following examples that other compounds of this invention can also be prepared in this manner.

Scheme 2

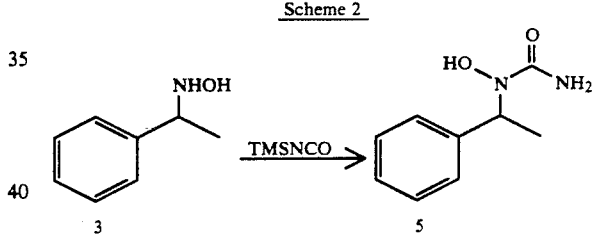

The hydroxylamine, 3, is treated with trimethylsilyl isocyanate, followed by ammonium chloride workup to give the urea, 5.

In addition to the methods described above the compounds of this invention may also be prepared according to the method of Scheme 3.

Scheme 3

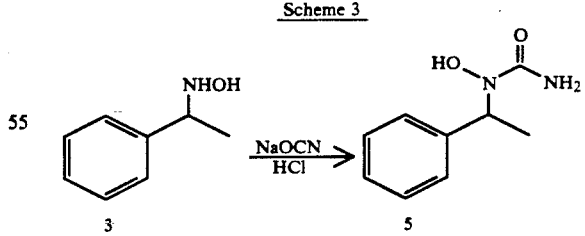

The hydroxylamine, 3, is dissolved in dilute hydrochloric acid and aqueous sodium cyanate is added. The resulting urea, 5, precipitates from the reaction and is collected.

In addition to the method described in Scheme 1, above hydroxylamine, 3, can also be prepared according to the method of Scheme 4, below. The sequence illustrates the case where $R^1$, $R^2$, $Y^1$ and $Y^2$ are hydrogen and where $R^2$ is phenyl and X is $CH(CH_3)$, however it will be seen from the following examples that other compounds of this invention can also be prepared in this manner.

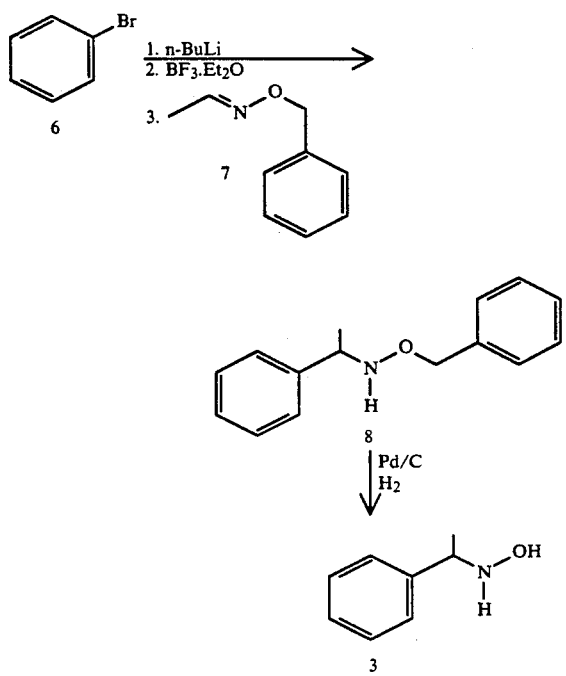

Scheme 4

Bromobenzene (6) is converted to phenyl lithium by treatment with n-butyl lithium at $-78°$ C. Boron trifluoride etherate is then added and this is reacted with acetaldehyde O-benzyl oxime (7) to yield (8). The O-benzyl protecting group is removed by catalytic hydrogenation. Other reagents may be substituted for those described above. For example, phenyl lithium may be prepared by treatment with t-butyl lithium, sec-butyl lithium, or lithium metal instead of n-butyl lithium. Other protecting groups may be used for acetaldehyde oxime. For example, benzyloxymethoxy, methyloxymethoxy, methoxybenzyl may be used instead of benzyl.

In an alternative method to this detailed above, compounds of this invention can be prepared according to the reaction sequence described in Scheme 5.

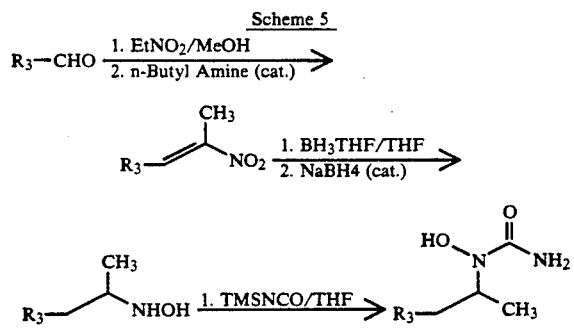

Scheme 5

Scheme 5 outlines the reaction of an aldehyde with nitroethane in methanol with an amine such as n-butylamine as a catalyst. The vinyl nitro compound obtained is then reduced with borane: THF and a catalytic amount of $NaBH_4$. This procedure is a modified method from a published procedure (J. Org. Chem. 1985, 50, 133). The hydroxylamine obtained is then reacted with an isocyanate to provide the corresponding hydroxyurea.

The following examples are provided to enable one skilled in the art to practice the present invention. These examples, however, are not to be read as limiting the scope of the invention as it is defined by the appended claims.

EXAMPLE 1

Preparation of N-hydroxy-N-(1(4-phenylmethoxyphenyl)ethyl)urea a. 4-Phenylmethoxyacetophenone 4-Hydroxyacetophenone (5.0 g, 36.7 mmole) was dissolved in dimethyl-sulfoxide (50 mL) and potassium t-butoxide (4.73 g, 42.2 mmole) was added. Twenty minutes later benzyl bromide (7.85 g, 45.8 mmole) was added. After an additional hour, the reaction mixture was poured into water and extracted with ether. The ether layer was dried with magnesium sulfate and evaporated to give an off white solid which was carried on without further purification.

b. 4-Phenylmethoxyacetophenone oxime

Using the method described in scheme 1, the material prepared as in part a, above and hydroxylamine hydrochloride (4.8 g, 0.70 mole) were dissolved in a mixture of ethanol (25 mL) and pyridine (25 mL) and heated at 50° for 2 hours. Most of the solvent was removed in vacuo and the residue dissolved in ether. After washing with 2N HCl (50 mL), the solution was dried over $MgSO_4$ and evaporated. A white crystalline solid was obtained and was carried on without further purification. An alternative work-up may also be used. The reaction mixture is diluted with water (300 mL) and the product precipitates. It is filtered off and dried in vacuo.

c. 1-(4-Phenylmethoxyphenyl) ethyl hydroxyl amine

4-Phenylmethoxy acetophenone oxime (3.7 g, 15.3 mmole), prepared as described in part b above, was dissolved in ethanol (30 mL) and cooled to 0° C. Borane-pyridine complex (4.6 mL, 46 mmole) was added via syringe under nitrogen followed ten minutes later by 6N HCl (15 mL). Within thirty minutes the reaction was complete and was brought to pH 9 with the addition of solid sodium carbonate of 2N NaOH. The mixture was extracted into ether and dried over $MgSO_4$. After evaporation a white solid resulted which was carried on without further purification.

d. N-hydroxy-N-(1-(4-phenylmethoxyphenyl)ethyl)urea

Method a

Using the method of scheme 2, the material prepared as in part a above (2 g, 8.2 mmole) was refluxed for thirty minutes with trimethylsilyl isocyanate (0.95 g, 8.2 mmole) in 30 mL dioxane. The reaction mixture was then washed with saturated $NH_4Cl$ solution, dried with $MgSO_4$, and evaporated. The residue was washed with ether to give 1.33 g of a white solid.

Method b

Using the method of scheme 1, the material prepared as in part a above (4 g, 16.4 mmole) was dissolved in toluene (100 mL) and HCl gas was bubbled through the mixture at a moderate rate for about four minutes. The solution was then heated to reflux and phosgene was bubbled through for another four minutes. After an additional one hour reflux, the mixture was allowed to cool to room temperature and then added to excess cold ammonium hydroxide solution. The precipitate was collected and recrystallized from aqueous ethanol. mp: 132°–134° C.; NMR (300 MHz, DMSO-$d_6$): 1.37 (d, 3H); 5.08 (s, 2H); 5.24 (q, 1H); 6.25 (s, 2H); 6.92 (d, 2H); 7.25 (d, 2H); 7.30–7.50 (m, 5H); 8.90 (s, 1H); Mass spectrum (EI): 286 M+, 269, 255, 243, 226, 211, 91.

EXAMPLE 2

Preparation of N-hydroxy-N-1-(4-phenylmethoxyphenyl) ethyl N'-methyl urea

The title compound was prepared according to the method of example 1, Method a, except using methyl isocyanate instead of trimethylsilyl isocyanate. mp 125°–128° C.; NMR (300 MHz, DMSO-$d_6$): 1.37 (d, 3H); 2.57 (dd, 3H); 5.08 (s, 2H); 5.20 (q, 1H); 6.78 (q, 1H); 6.92 (d, 2H); 7.20–7.50 (m, 7H); 8.90 (s, 1H); IR (KBr): 3450, 1630, 1610, 1520, 1250; Mass spectrum (EI): 300 M+, 283, 226, 211, 91.

EXAMPLE 3

Preparation of N-hydroxy-N-(1-(4-phenylmethoxyphenyl) ethyl N'N'-dimethyl urea a. N-hydroxy-N-(1-(4-phenylmethoxyphenyl)ethyl) urea, prepared as in example 1, (5.0 g, 21 mmole) was treated with dihydropyran (2.1 mL, 23 mmole) and a few crystals of p-toluene sulfonic acid in methylene chloride (200 mL) for 6 hours. The mixture was evaporated in vacuo and chromatographed on silica gel eluting with ether to give 3.5 g of a colorless oil.

b. N-(2-tetrahydropyranoxy)-N-(1-(4-phenylmethoxyphenyl) ethyl) N'N'-dimethyl urea.

The material prepared in part a, above (3.5 g, 10.8 mmole) was dissolved in THF (50 mL) and sodium hydride (60%, 432 mg, 10.8 mmole) was added. After hydrogen evolution ceased, methyliodide (0.67 mL) was added and the mixture stirred overnight. The solvent was evaporated in vacuo and the residue chromatographed on silica gel eluting with ether to obtain 1.8 g of the desired product.

c. N-hydroxy-N-(1-(4-phenylmethoxyphenyl)ethyl) N'N'-dimethyl urea. The material prepared as in part b above (1.8 g) was dissolved in methanol (20 mL) and a few crystals of p-toluene sulfonic acid were added. The solvent was evaporated and the mixture was partitioned between saturated sodium bicarbonate solution and methylene chloride. After drying over MgSO$_4$, concentration in vacuo gave a white solid (870 mg). mp: 125°–126° C.; NMR (DMSO-$d_6$, 300 MHz): 1.38 (d, 3H); 2.82 (s, 6H); 4.84 (q, 1H), 5.09 (s, 2H); 6.90–7.00 (m, 2H); 7.20–7.48 (m, 7H); 8.51 (brs, 1H); Mass spectrum (CI—NH$_3$): 315 (M+1)+, 299, 297, 211.

EXAMPLE 4

Preparation of N,N'-dihydroxy-N-(1-(4-phenylmethoxyphenyl) ethyl urea

The desired compound was prepared according to the method of example 1, method a, except using hydroxylamine instead of ammonium hydroxide. mp: 157°–159° C.; NMR (DMSO-$d_6$, 300 MHz): 1.46 (d, 3H); 5.03 (s, 2H); 5.14 (q, 1H); 6.92 (m, 2H); 7.24 (m, 2H); 7.30–7.50 (m, 5H); 8.31 (brs, 1H); 8.88 (brs, 1H); 9.34 (brs, 1H); Mass spectrum (EI): 302, 286, 241, 211, 91, 65.

EXAMPLE 5

Preparation of N-hydroxy-N-(4-phenylmethoxyphenylmethyl) urea

The desired material was prepared according the method of example 1, except using 4-hydroxybenzaldehyde instead of 4-hydroxyacetophenone. mp: 147°–149° C.; NMR (DMSO-$d_6$, 300 MHz): 4.42 (s, 2H); 5.08 (s, 2H); 6.31 (brs, 2H); 6.95 (m, 2H); 7.19 (m, 2H); 7.30–7.50 (m, 5H); 9.27 (s, 1H); Mass spectrum (CI—NH$_3$): 290 (M+NH$_4$)+, 273 (M+1)+, 257, 230, 212.

EXAMPLE 6

Preparation of N-hydroxy-N-(4-phenylmethoxyphenylmethyl)-N'-methyl-urea

The title compound was prepared according the method of example 1, method a, except using 4-hydroxybenzaldehyde instead of 4-hydroxy-acetophenone and using methylisocyanate instead of trimethylsilylisocyanate. mp: 150°–153° C.; NMR (DMSO-$d_6$, 300 MHz): 2.60 (3H, d); 4.42 (2H, s); 5.08 (2H, s); 6.86 (1H, q); 6.94 (2H, d); 7.19 (2H, d); 7.28–7.47 (5H, m); 9.19 (1H, s); Mass Spectrum (EI): 286 M+, 269, 197, 91.

EXAMPLE 7

Preparation of N-hydroxy-N-(1-(4-phenylmethoxy-3,5-dimethoxyphenyl)ethyl) urea

The desired material was prepared according to the methods of example 1, except using 3,5-dimethoxy-4-hydroxyacetophenone instead of 4-hydroxyacetophenone. mp: 108°–110° C.; NMR (300 MHz, DMSO-$d_6$): 1.40 (d, 3H); 3.76 (s, 6H); 4.85 (s, 2H); 5.23 (q, 1H); 6.36 (s, 2H); 6.65 (s, 2H); 7.29–7.50 (m, 5H); 9.06 (s, 1H); Mass spectrum (EI): 346 M+, 336, 279, 91.

EXAMPLE 8

Preparation of N-hydroxy-N-(1-(4-(2-phenyl)ethoxyphenyl)ethyl) urea

The desired material was prepared according to the method of example 1 except using 2-phenethylbromide instead of benzyl bromide mp: 126°–128° C.; NMR (300 MHz, DMSO-$d_6$): 1.36 (d, 3H); 3.02 (d, 2H); 4.16 (d, 2H); 5.23 (q, 1H); 6.25 (brs, 2H); 6.84 (m, 2H); 7.23 (m, 2H); 7.32 (m, 5H); 8.98 (brs, 1H); Mass spectrum (EI): No M+, 283 (M-OH)+, 225, 121, 105.

EXAMPLE 9

Preparation of N-hydroxy-N-(1-(2-naphthyl)ethyl) urea

The desired material was prepared according to the method of example 1, except using 2-acetonaphthone instead of acetophenone. mp: 140°–142° C., NMR (300 MHz, DMSO-$d_6$): 1.51 (d, 3H); 5.46 (q, 1H); 6.34 (brs, 2H); 7.45–7.54 (m, 3H); 7.81–7.90 (m, 4H); 9.11 (s, 1H); Mass spectrum (EI): 230 M+, 213, 155, 127, 115, 77.

EXAMPLE 10

Preparation of N,N'-dihydroxy-N-(1-(2-naphthyl)ethyl) urea a. O-benzyl 2-acetonaphthone oxime was prepared according to the method of example 1 part b, except using 2-acetonaphthone instead of 4-phenylmethoxyacetophenone and using O-benzylhydroxylamine instead of hydroxylamine.

b. N-benzyloxy-N'-hydroxy-N-(1-2-naphthyl)ethyl) urea.

The material prepared as described in part a, (3.2 g, 11.5 mmole) was dissolved in toluene and HCl gas was bubbled through at a moderate rate for about 3 minutes. The solution was heated to reflux and phosgene was added over about 5 minutes. The insoluble hydrochloride salt dissolved. After refluxing for one hour the mixture was cooled and added to a solution of hydroxylamine hydrochloride (960 mg, 13.8 mmole) and triethylamine (3.5 g, 35 mmole) in THF (30 mL) and water (5 mL). The mixture was poured into 2N HCl solution and ether was added. The organic phase was dried over $MgSO_4$ and evaporated. The residue was chromatographed on silica gel, eluting with 75% ether in hexanes to yield a white solid.

c. N,N'-dihydroxy-N-(1-(2-naphthyl)ethyl) urea was prepared by catalytic hydrogenation of the material prepared in part b, above, using 5% palladium on carbon in ethanol. mp: 148°–150° C.; NMR (300 MHz, DMSO-$d_6$): 1.51 (d, 3H); 5.37 (q, 1H); 7.45–7.54 (m, 4H); 7.81–7.90 (m, 4H); 8.34 (s, 1H); 9.10 (s, 1H); 9.43 (s, 1H); IR (KBr): 3220, 1620, 1470; Mass spectrum (EI): 246 M+, 230, 155.

EXAMPLE 11

Preparation of N-hydroxy-N-(1-(4-butoxyphenyl)ethyl) urea

The desired material was prepared according to the method of Example 1, except using 1-bromobutane instead of benzyl bromide. NMR (300 MHz, CDCl$_3$): 0.97 (t, 3H); 1.46 (m, 2H); 1.53 (d, 3H); 1.76 (m, 2H); 3.94 (t, 2H); 5.23 (brs, 2H); 5.42 (q, 1H); 6.71 (s, 1H); 6.85 (d, 2H); Mass spectrum (EI): 252 M+, 235, 192, 177, 121.

EXAMPLE 12

Preparation of N-Hydroxy-N-1-(5-methylthien-2-yl)ethyl urea a) To a stirred solution of 2-acetyl-5-methylthiophene (5.0 g, 35.7 mmol) in ethanol/pyridine (1:1) (30 mL) was added hydroxylamine hydrochloride (5.0 g, 71.9 mmol). The reaction was stirred for 1 h before evaporating the ethanol and diluting the residue with water. The aqueous solution was extracted with ethyl acetate (3×50 mL), dried over $MgSO_4$ and evaporated. A quantitative yield of a yellow solid was obtained.

b) To a stirred solution of the product obtained in part a (5.5 g, 35.7 mmol) in ethanol was added $BH_3$.Pyridine (11.9 mL, 117.8 mmol). After 20 minutes, 10% HCl/EtOH (35 mL) was added slowly via dropping funnel. Two hours later the reaction was complete and the ethanol was removed. The aqueous residue was diluted with water, neutralized with 2N NaOH, extracted with ethyl acetate (3×50 mL), dried over MgSO4 and evaporated. The resulting oil was purified by chromatography (silica gel, ether-hexane, 2:3) to yield 2.2 g of a clear oil.

c) To a stirred solution of the product obtained in part b (2.2 g, 14.0 mmol) in THF was added trimethylsilylisocyanate (3.35 mL, 21.0 mmol). After 1 h, the reaction was complete and saturated NH$_4$Cl was added. The THF was evaporated and the residue was extracted with ethyl acetate (3×50 mL), dried over MgSO$_4$, and evaporated. The resulting residue was purified by chromatography (silica gel, 7% methanol-methylene chloride) to yield 1.7 g of a waxy solid.

NMR (300 MHz, DMSO-$d_6$) 1.38 (3H, t, J=7.5 Hz), 2.38 (3H, s), 5.39 (1H, q, J=7.5 Hz), 6.36 (2H, br s), 6.59 (1H, m), 6.70 (1H, m), 9.08 (1H, s); MS: (M+H)+ =201; (M+NH4)+ =218;

EXAMPLE 13

Preparation of N-hydroxy-N-(1-(3-butoxyphenyl)ethyl) urea

The desired material is prepared according to the method of Example 1, except using 1-bromobutane instead of benzyl bromide and using 3-hydroxyacetophenone instead of 4-hydroxyacetophenone.

EXAMPLE 14

Preparation of N-hydroxy-N-(1-(4-(2-methylpropyl)phenyl)ethyl) urea

The desired material is prepared according to the method of Example 1, except using 4-isobutylacetophenone instead of 4-phenylmethoxyacetophenone in part b.

EXAMPLE 15

Preparation of N-hydroxy-N-(1-(4-cyclohexyl)phenyl)ethyl) urea

The desired material is prepared according to the method of Example 1, except using 4-cyclohexylacetophenone instead of 4-phenylmethoxy-acetophenone in part b.

EXAMPLE 16

Preparation of N-hydroxy-N-(2-(4-butoxyphenyl)ethyl) urea a. 4-Butoxybenzaldehyde was prepared according to the method of Example 1, part a, except using 1-bromobutane instead of benzylbromide and using 4-hydroxybenzaldehyde instead of 4-hydroxyacetophenone.

b. 1-nitro-2(-4-butoxyphenyl)ethene The material prepared as in part a above (1.8 g, 10 mmole), prepared as in Example 1, part a, and nitromethane (0.6 g, 10 mmole) were dissolved in ethanol (30 mL). Potassium hydroxide (1.3 g, 20 mmole) in ethanol (10 mL) was added and a white solid mass formed. The mixture was poured into 6N HCl (50 mL) and the white mass turned to a yellow solid. This material was collected by filtration and dissolved in ether (100 mL). The solution was dried with MgSO4 and evaporated. A yellow solid (1.0 g, 45%) was obtained which was carried on without further purification.

c. N-hydroxy-2-(4-butoxyphenyl)ethyl amine.

The material prepared as described above (6.0 g, 27.1 mmole) in THF (80 mL) was added to borane-THF (28.4 mmole) at 0° C. Sodium borohydride (10 mg) was added. After stirring for 8 hours most of the yellow color of the starting material was gone. Water (75 mL) and 2N HCl were added and the mixture was heated to 60° for 45 minutes. The reaction mixture was washed with ether and then neutralized with 2N NaOH. The product was extracted into ether which was dried over MgSO$_4$ and evaporated. A white solid (2.2 g) was obtained and carried on without further purification.

d. N-hydroxy-N-(2-(4-butoxyphenyl)ethyl) urea.

The material described above is converted to the desired compound using the method described in Example 1 part d.

EXAMPLE 17

Preparation of
N-hydroxy-N-(1-methyl-2-(4-butoxyphenyl)ethyl) urea

The desired material is prepared according to the method of Example 16, except using nitroethane instead of nitromethane.

EXAMPLE 18

Preparation of
N-hydroxy-N-(3-(4-butoxyphenyl)propyl) urea a. Methyl 4-butoxycinnamate was prepared according to the method of Example 1, part a, except using methyl 4-hydroxycinnamate instead of 4-hydroxyacetophenone and using 1-bromobutane instead of benzylbromide.

b. Methyl 3-(4-butoxyphenyl)propionate by catalytic hydrogenation of the material prepared as in part a using 20% palladium on carbon.

c. 3-(4-Butoxyphenyl)-1-propanol.

The material prepared as in part b (10 g, 42 mmole) was dissolved in THF (50 mL) and lithium aluminum hydride (1M in THF, 42 mL) was added rapidly. Fifteen minutes later, 2N HCl was added to quench the reaction. The organic layer was separated and dried with MgSO$_4$ and evaporated to give a colorless oil.

d. 3-(4-Butoxyphenyl)propanal

The alcohol prepared as in part c (9 g) was dissolved in methylene chloride (100 mL) and pyridinium chlorochromate (18 g, 84 mmole) was added. Three hours later ether was added filtered through silica gel. The filtrate was evaporated and the residue chromatographed on silica gel.

e. N-hydroxy-N-(3-(4-butoxyphenyl)propyl)urea is prepared according to the method of Example 1, except using the material prepared as in part d above instead of phenylmethoxyacetophenone.

EXAMPLE 19

Preparation of
N-hydroxy-N-(1-methyl-3-(4-butoxyphenyl)propyl)urea a. 4-(4-Butoxyphenyl)-2-propanol. 3-(4-butoxyphenyl)propanal (5.0 g, 24 mmole) prepared as described in Example 18, part d, was dissolved in THF and cooled to −78° C. Methyl lithium in hexanes (27 mmole) was added. The reaction was allowed to warm to room temperature and then was quenched with 2N HCl. The organic layer was separated, dried over MgSO$_4$ and evaporated to give a colorless oil.

b. 4-(4-Butoxyphenyl)-2-propanone was prepared according to the method of Example 18, part d, except using the material prepared in part a above instead of 3-(4-butoxyphenyl)-1-propanol.

c. N-hydroxy-N-(1-methyl-3-(4-butoxyphenyl)propyl) urea is prepared according to the method of Example 1, except using the material prepared as in part b above instead of acetophenone.

EXAMPLE 20

Preparation of
N-hydroxy-N-(1-methyl-1-(4-butoxyphenyl)ethyl) urea a. 4-Butoxyacetophenone was prepared as in Example 1, part a except using 1-bromobutane instead of benzylbromide.

b. 1-Methyl-1-(4-butoxyphenyl)ethanol

The material prepared as described above (8.0 g, 41.7 mmole) was dissolved in ether (100 mL) and cooled to 0° C. Methyl lithium (1.2M in hexanes, 62.5 mmole) was added and the mixture stirred for 30 minutes. HCl (2N) was added and the ether layer was separated, dried over MgSO$_4$ and concentrated in vacuo.

c. N-hydroxy-N-(1-Methyl-1-(4-butoxyphenyl)) ethylamine.

O-benzyl hydroxylamine hydrochloride (7.35 g, 46.1 mmole) was suspended in THF (200 mL). Triethyl amine (6.5 mL, 46.1 mmole) was added and the mixture stirred for 1 hour. The suspension was then filtered to remove triethyl amine hydrochloride and the filtrate was concentrated in vacuo. The residue was redissolved in benzene (20 mL) and added to a stirred solution of the material prepared in part a (3.55 g, 17.1 mmole) in benzene (50 mL). Trifluoroacetic acid (1.3 mL, 16.9 mmole) was added neat and the mixture stirred for 48 hours. At that time the mixture was concentrated to dryness and then redissolved in ether (150 mL). This solution was dried over MgSO$_4$ and evaporated to produce an oil which was carried on immediately without purification.

d. N-hydroxy-N-(1-methyl-1-(4-butoxyphenyl)ethyl urea is prepared according to the procedure of Example 1, except using the material prepared as in part c above instead of 4-phenylmethoxyacetophenone.

EXAMPLE 21

Preparation of
N-hydroxy-N-(1-(4-butoxyphenyl)-2-methylpropyl) urea a. 1-(4-Butoxyphenyl)-2-methyl-1-propanol.

4-Butoxy-benzaldehyde (1.0 g, 5.6 mmole), prepared as described in Example 15, part a, was dissolved in ether (50 mL) and cooled to −78° C. Isopropyl magnesium bromide in THF (6.5 mmole) was added. The reaction mixture was allowed to warm to room temperature and then quenched with water (20 mL). The ether layer was separated, dried with MgSO$_4$ and evaporated to give a liquid (1.16 g).

b. 4-Butoxyphenyl isopropyl ketone.

The material prepared in part a (1.16 g, 5.2 mmole) was dissolved in methylene chloride (25 mL) and pyridinium chlorochromate (2.82 g, 13.1 mmole) was added. Three hours later ether (25 mL) was added and the resulting mixture filtered through celite. The filtrate was dried over MgSO$_4$ and evaporated to afford 1.07 g of an oil.

c. N-hydroxy-N-(1-4-butoxyphenyl)-2-methylpropyl) urea is prepared according the method of Example 1, except using the material prepared in part b above instead of 4-phenylmethoxyacetophenone.

EXAMPLE 22

Preparation of
N-hydroxy-N-(1-(6-butoxy-2-naphthyl)ethyl) urea a. 2-Bromo-6-butoxynaphthalene was prepared according to the method of Example 1, part a, except using 6-bromo-2-naphthol instead of 4-hydroxyacetophenone and using 1-bromobutane instead of benzylbromide.

b. 1-(6-butoxy-2-naphthyl)-ethanol.

The material prepared as above (11 g, 39.3 mmole) was dissolved in THF and cooled to −78° C. Tert-butyl lithium (1.7M in hexanes, 86.4 mmole) was added and the mixture stirred for thirty minutes. Acetaldehyde (2.23 mL, 40 mmole) was added and the mixture was stirred an additional thirty minutes. The reaction was quenched by the addition of NH$_4$Cl and the product extracted into ether. After drying over MgSO$_4$ and concentrated in vacuo, the resulting residue was carried on without purification.

c. 6-butoxy-2-acetonaphthone.

The desired material was prepared according to the method of Example 21, part b, except using the material prepared according to part b above instead of 1-(4-Butoxyphenyl)-2-methyl-1-propanol.

d. N-hydroxy-N-(1-(6-butoxy-2-naphthyl)ethyl urea is prepared according to the method of Example 1, except using the material prepared according to the method of part c above instead of 4-phenylmethoxyacetophenone (R$_1$, R$_2$=H, R$_3$=6-C$_4$H$_9$-2-naphthyl, X=CH(CH$_3$)). mp: 135°-137° C.; NMR (300 MHz, DMSO-d$_6$): 0.92 (t, 3H); 1.50 (m, 4H); 1.75 (m, 2H); 2.03 (s, 3H); 4.08 (t, 3H); 5.75 (br m, 1H); 7.10-7.85 (m, 7H); 9.55 (s, 1H); Mass Spectrum (EI): 301, 284, 242, 227, 171.

EXAMPLE 23

Preparation of N-hydroxy-N-(1-(6-phenylmethoxy-2-naphthyl)ethyl) urea

The desired material is prepared according to the method of Example 22 except using benzylbromide instead of 1-bromobutane.

EXAMPLE 24

Preparation of N-hydroxy-N-(1-(4-(4-fluorophenylmethoxy)phenyl)ethyl) urea

The desired material is prepared according the method of Example 1, except using 4-fluorobenzylbromide instead of benzylbromide.

EXAMPLE 25

Preparation of N-hydroxy-N-(1-(4-(4-methoxyphenylmethoxy)phenyl)ethyl) urea

The desired material is prepared according the method of Example 1, except using 4-methoxybenzylbromide instead of benzylbromide.

EXAMPLE 26

Preparation of N-hydroxy-N-(1-(4-(4-trifluoromethylphenyl methoxy)-phenyl)ethyl) urea The desired material is prepared according the method of Example 1, except using 4-trifluoromethylbenzylbromide instead of benzylbromide.

EXAMPLE 27

Preparation of N-hydroxy-N-(3-nitro-4-butoxyphenylmethyl) urea

The desired material is prepared according to the method of Example 1, except using 3-nitro-4-hydroxybenzaldehyde instead of 4-hydroxyaceto-phenone.

EXAMPLE 28

Preparation of N-hydroxy-N-(1-(4-phenylmethoxy-3.5-dichlorophenyl)ethyl) urea a. 4-Phenylmethoxy-3,5-dichlorobenzonitrile was prepared according to the method of Example 1, part a, except using 3,5-dichloro-4-hydroxy benzonitrile instead of 4-hydroxy-acetophenone.

b. 4-Phenylmethoxy-3,5-dichloroacetophenone.

The material prepared as in part a above (6.8 g, 26 mmole) was dissolved in benzene (200 mL) and methyl magnesium bromide (10 mL, 3.0M in ether) was added. The mixture was refluxed for three hours, cooled and 6N HCl was added. The mixture was refluxed again for 2 hours and then poured into a saturated sodium bicarbonate solution. The organic layer was dried over MgSO$_4$ and evaporated. The residue was chromatographed on silica gel eluting with 50% ether in hexanes to give a 36% yield of the desired product.

c. N-hydroxy-N-(1-(4-phenylmethoxy-3,5-dichlorophenyl)ethyl) urea is prepared according to the method of Example 1, except using the material prepared as in part b above instead of 4-phenylmethoxyacetophenone.

EXAMPLE 29

Preparation of N-hydroxy-N-(2-hydroxy-4-phenylmethoxyphenylmethyl) urea

The desired material is prepared according to the method of Example 1, except using 2-hydroxy-4-phenylmethoxy acetophenone instead of 4-phenylmethoxyacetophenone.

EXAMPLE 30

Preparation of N-hydroxy-N-(1-(4-phenylthiomethoxyphenyl)ethyl urea a. 4-Phenylthiomethoxyacetophenone. Benzyl phenyl sulfide (10.0 g, 50 mmole) was added at 0° C. to a solution of acetyl chloride (4.3 g, 55 mmole) and aluminum chloride (28 g, 204 mmole) in nitroethane (75 mL). The mixture was stirred for 3 hours at 0° C. and then slowly poured over ice and 3N HCl. The resulting mixture was extracted with ether, which was then dried over MgSO$_4$ and concentrated in vacuo. The residue was chromatographed on silca gel eluting with 10% ethyl acetate in hexanes to give a white solid (3.41 g).

b. N-hydroxy-N-(1-(4-phenylthiomethoxyphenyl)ethyl urea is prepared according to the method of Example 1, except using the material prepared as in part a, above, instead of 4-phenylmethoxyacetophenone.

EXAMPLE 31

Preparation of N-hydroxy-N-(1-(4-(2,4,6-trimethylphenyl)phenyl)ethyl urea a. 4-(2,4,6-trimethylphenyl)acetophenone. Mesityl bromide (6 g, 30 mmole) was dissolved in THF (60 mL) and cooled to −78° C. Tert butyl lithium (1.7M in hexanes, 63.3 mmole) was added and the mixture stirred for 20 minutes. In a separate flask, zinc chloride (4.1 g, 30.1 mmole) was suspended in THF (30 mL) and cooled to −78° C. The lithium reagent prepared above was added via cannula to the zinc suspension and the resulting mixture stirred for 60 minutes. In another flask palladium bis(triphenylphosphino)dichloride was dissolved in THF (40 mL), di-isobutylaluminum hydride (1.0M in THF, 3.02 mmole) was added, followed by 4-bromoacetophenone (5.39 g, 27.1 mmole) in THF (30 mL). The zinc reagent prepared above was transferred via cannula to this solution and the mixture was stirred for two hours. The reaction mixture was evaporated in vacuo and the residue dissolved in ether. This was then washed with 2N HCl and dried over MgSO4 and evaporated. The residue was chromatographed on 150 g silica gel, eluting with 12% ether in hexanes. A white solid (3.8 g) was obtained.

b. N-hydroxy-N-(1-(4-(2,4,6-trimethylphenyl)phenyl)ethyl) urea is prepared according to the method of Example 1, but using the material prepared as in part a above instead of phenylmethoxyacetophenone.

EXAMPLE 32

Preparation of
N-hydroxy-N-(1-(3-benzoylphenyl)ethyl) urea a. 3-Bromobenzophenone. 3-Bromobenzoyl chloride (33 g) was dissolved in benzene (125 mL) and aluminum chloride (30 g) was added over 25 minutes. The mixture was refluxed for one hour, cooled to room temperature and then added to ice (50 g) and concentrated HCl (50 mL). The organic layer was dried over MgSO4 and evaporated in vacuo to give a brown solid. This was then Kugelrohr distilled to give an off-white solid (39 g).

b. 3-Bromobenzophenone ethylene glycol ketal

The material prepared as in part a above (39 g, 150 mmole), ethylene glycol (42 mL, 750 mmole), trimethyl orthoformate (33 mL, 300 mmole) and a few crystals of p-toluene sulfonic acid were heated to 60° C. for 24 hours. The mixture was then poured into saturated NaHCO3 solution and extracted into ether. The ether was dried over MgSO4 and evaporated. The residue was chromatogaphed on silica gel eluting with 40% ether in hexanes to give a colorless oil (30 g).

c. 3-Benzoylacetophenone ethylene glycol ketal

The material prepared as in part b above (23.6 g, 77.3 mmole) was dissolved in THF (200 mL) and cooled to −78° C. Tertbutyl lithium n100 mL, 1.7M in hexanes) was added and then the mixture was stirred for 20 minutes. N,O-dimethyl acetohydroxamic acid (15.9 g, 154 mmole) in THF (50 mL) was added and the mixture was stirred for an additional thirty minutes. The reaction was quenched with pH 7 phosphate buffer and extracted into ether. The solvent was evaporated, and the resulting residue chromatographed on silica gel, eluting with 40% ether in hexanes.

d. N-hydroxy-N-(1-(3-benzoylphenyl)ethyl) urea is prepared according to the method of Example 1, but using the material prepared as in part c above instead of phenylmethoxyacetophenone.

EXAMPLE 33

Preparation of
N-hydroxy-N-(1-(4-(2-phenylethenyl)phenyl)ethyl) urea a. 4-(2-Phenylethenyl)acetophenone is prepared according to the method of Example 21, parts a and b, except using 4-formylstilbene instead of 4-butoxybenzaldehyde and using methyl magnesium bromide instead of isopropyl magnesium bromide.

b. N-hydroxy-N-(1-(4-(2-phenylethenyl)phenyl)ethyl acetamide is prepared according to the method of Example 1, except using the material prepared as described in part a above instead of phenylmethoxyacetophenone.

EXAMPLE 34

Preparation of
N-hydroxy-N-(1-(4-(2-phenylethyl)phenyl)ethyl) urea a. 4-(2-Phenylethyl)benzaldehyde is prepared by catalytic hydrogenation of 4-formylstilbene over 20% palladium on carbon in methanol.

b. N-hydroxy-N-(1-(4-(2-phenylethyl)phenyl)ethyl) acetamide is prepared according to the method of Example 33, except using the material prepared as in part a above instead of 4-formylstilbene.

EXAMPLE 35

Preparation of
N-hydroxy-(1-(4-phenylmethoxyphenyl)ethyl) urea sodium salt

The material prepared as in Example 1 is dissolved in tetrahydrofuran and one equivalent of sodium hydride is added. After hydrogen evolution ceases, the solvent is removed in vacuo to yield the desired product.

EXAMPLE 36

Preparation of
N-hydroxy-(1-(4-phenylmethoxyphenyl)ethyl) urea potassium salt

The material prepared as in Example 1 is dissolved in tetrahydrofuran and one equivalent of potassium hydride is added. After hydrogen evolution ceases, the solvent is removed in vacuo to yield the desired product.

EXAMPLE 37

Preparation of
N-hydroxy-(1-(4-phenylmethoxyphenyl)ethyl)urea ammonium salt

The material prepared as in Example 1 is dissolved in tetrahydrofuran and ammonia is bubbled through. The solvent is removed in vacuo to yield the desired product.

EXAMPLE 38

Preparation of
N-hydroxy-(1-(4-phenylmethoxyphenyl)ethyl) urea triethylammonium salt The material prepared as in Example 1 is dissolved in tetrahydrofuran and one equivalent of triethylamine is added. The solvent is removed in vacuo to yield the desired product.

EXAMPLE 39

Preparation of
N-hydroxy-(1-(4-phenylmethoxyphenyl)ethyl) urea tetraethyl ammonium salt The material prepared as in Example 1 is dissolved in tetrahydrofuran and one equivalent of tetraethylammonium hydroxide is added. The solvent is removed in vacuo to yield the desired product.

EXAMPLE 40

Preparation of
N-butyryloxy-(1-(4-phenylmethoxyphenyl)ethyl) urea

The material prepared as in Example 1 and 1.1 equivalent of triethylamine are dissolved in tetrahydrofuran and 1 equivalent of butyryl chloride is added. Ether is added and the material is washed with 2N HCl, dried with MgSO$_4$ and then evaporated in vacuo to yield the desired product.

EXAMPLE 41

Preparation of N-benzoyloxy-(1-(4-phenylmethoxyphenyl)ethyl) urea

The material prepared as in Example 2 and 1.1 equivalent of triethylamine are dissolved in tetrahydrofuran and 1 equivalent of benzoyl chloride is added. Ether is added and the material is washed with 2N HCl, dried with MgSO$_4$ and then evaporated in vacuo to yield the desired product.

EXAMPLE 42

Preparation of N-Hydroxy-N-1-(2,5-dimethylthien-3-yl)ethyl urea

The desired compound was prepared by the same method as described for Example 12 except using 3-acetyl-2,5-dimethylthiophene instead of 2-acetyl-5-methylthiophene. mp = 146°–147° C.; NMR (300 MHz, DMSO-d6) 1.29 (3H, d, J=7.5 Hz), 2.29 (3H, s), 2.32 (3H, s), 5.23 (1H, q, J=7.5 Hz), 6.21 (2H, br s), 6.74 (1H, s), 9.02 (1H, s); MS: (M+H)$^+$=215, (M+NH$_4$)$^+$=232.

Analysis Cal'd for C$_9$H$_{14}$N$_2$O$_2$S: C, 50.45; H, 6.56; N, 13.93. Found: C, 50.44; H, 6.56; 13.91.

EXAMPLE 43

Preparation of N-Hydroxy-N-1-(thien-3-yl)ethyl urea

The desired compound was prepared by the same method as described for Example 12 except using 3-acetylthiophene instead of 2-acetyl-5-methylthiophene. mp.=138.5°–140° C., NMR (300 MHz, DMSO-d6) 1.39 (3H, d, J=7.5 Hz), 5.32 (1H, q, J=7.5 Hz), 6.33 (2H, br s), 7.05 (1H, m), 7.27 (1H, m), 7.42 (1H, m) 9.03 (1H, s); MS: (M+H)$^+$=187, (M+NH$_4$)$^+$=204.

EXAMPLE 44

Preparation of N-Hydroxy-N-(thien-3-yl)methyl urea

The desired compound was prepared by the same method as described for Example 12 except using 3-thiophene-carboxaldehye instead of 2-acetyl-5-methylthiophene. mp.=129°–131° C., NMR (300 MHz, DMSO-d6) 4.48 (2H, s), 6.36 (2H, br s), 7.04 (1H, m), 7.30 (1H, m), 7.45 (1H, m) 9.35 (1H, s); MS: (M+H)$^+$=173, (M+NH$_4$)$^+$=190.

Analysis Cal'd for C$_6$H$_8$N$_2$O$_2$S: C,41.85; H, 4.68; N, 16.27. Found: C, 41.61; H, 4.68, N, 16.27.

EXAMPLE 45

Preparation of N-hydroxy-N-(thien-2-yl)methyl urea a) 2-Thiophenecarboxaldoxime To a solution of 2-thiophene-carboxaldehyde (3.0 g, 26.8 mmole) in 10 mL ethanol at room temperature was added pyridine (4.3 mL, 53.5 mmole) and hydroxylamine hydrochloride (2.8 g, 40.1 mmole) with stirring. After one hour at room temperature the solution was diluted with water and extracted with ethyl acetate (3×50 mL). The combined organic extracts were washed with 2M HCl (60 mL), and brine (60 mL), dried over MgSO$_4$, filtered and concentrated to yield 1.09 g of a white solid (m.p.=123° C.).

b) Thien-2-ylmethyl hydroxylamine

The oxime from part a (3.4 g, 26.8 mmol) was dissolved in 50 mL ethanol at room temperature and borane pyridine complex (8.1 mL, 80.3 mmol) was added. The solution was stirred one hour at room temperature and was then cooled to 0° C. at which time 6N HCl (80 mL) was slowly added. When the heat of the reaction subsided, the flask was warmed to room temperature and allowed to stir approximately one hour. Then the solution was diluted with water and neutralized with solid sodium carbonate. The aqueous layer was extracted with ethyl acetate (3×50 mL) and the combined organic layers were washed with brine and dried (MgSO$_4$), filtered and evaporated from toluene to remove the excess pyridine to give 3.4 g of product as a white solid.

c) N-Hydroxy-N-(1-thien-2-ylmethyl) urea

To a solution of trimethylsilylisocyanate (3.1 mL, 23.2 mmole) in 10 mL THF at room temperature was added the above hydroxylamine (1.5 g, 11.6 mmole) in 10 mL of THF with stirring. After thirty minutes the reaction was quenched with saturated ammonium chloride solution (10 mL). The aqueous layer was saturated with sodium chloride and extracted with ethyl acetate (3×, 25 mL). The combined organic extract was dried over MgSO$_4$, filtered and concentrated. The resultant solid was washed with ether and the crystals were collected to yield 0.82 g (41%) of the desired product as a white solid. m.p.=112° C.; $^1$H NMR (300 MHz, DMSO-d6) 9.41 (br s, 1H), 7.40 (dd, J=2.4, 5.6 Hz, 1H), 6.95 (m, 2H), 6.40 (br s, 2H), 4.63 (br s, 2H); MS (M+H)$^+$=173; (M+NH4)$^+$=190.

Analysis calc'd for C$_6$H$_8$N$_2$O$_2$S: C, 41.85; H, 4.68; N, 16.27. Found: C, 41.55; H, 4.58; N, 16.15.

EXAMPLE 46

Preparation of N-hydroxy-N-1-(3-methylthien-2-yl)ethyl urea

The same method as described for Example 45 was used substituting 2-acetyl-3-methylthiophene instead of 2-thiophenecarboxaldehyde to provide the desired product. m.p.=131° C.; $^1$H NMR (300 MHz, DMSO-d6) 9.16 (bs, 1H), 7.25 (d, J=5.97 Hz, 1H), 6.78 (d, J=5.90 Hz, 1H), 6.30 (bs, 2H), 5.09 (q, J=6.00 Hz, 13.21 Hz, 1H), 2.16 (s, 3H), 1.35 (d, J=6.91 Hz, 3H); MS (M+H)$^+$=201; (M+NH$_4$)$^+$=218.

Analysis calc'd for C$_8$H$_{12}$N$_2$O$_2$S: C, 47.98; H, 6.04; N, 13.99. Found: C, 47.79; H, 5.96; N, 13.94.

EXAMPLE 47

Preparation of N-hydroxy-N-(1-thien-2-yl)ethyl urea

The same method as described for Example 45 was used substituting 2-acetylthiophene instead of 2-thiophenecarboxaldehyde to provide the desired product. m.p.=129.5° C.; $^1$H NMR (300 MHz, DMSO-d6) 9.13 (br s, 1H), 7.36 (dd, J=6.3, 13.8 Hz, 1H), 6.94 (m, 2H), 6.38 (br s, 2H), 5.49 (q, J=6.3, 13.8 Hz, 1H), 1.42 (d, J=7.00 Hz, 3H). MS (M+H)$^+$=187.

Analysis calc'd for C$_7$H$_{10}$N$_2$O$_2$S: C, 45.15; H, 5.41; N, 15.04. Found: C, 45.00; H, 5.35; N, 15.04.

EXAMPLE 48

Preparation of N-hydroxy-N-(1-(5-pyrid-2-yl)thien-2-yl)ethyl urea a) 2-Pyrid-2-ylthiophene. To a solution of thiophene (4.7 mL, 59.4 mmole) at 0° C. was added 2.5M n-butyllithium (24 mL, 59.4 mmole) dropwise via syringe. The solution was stirred 3 h and was then transferred via cannula into a stirred solution of zinc chloride (8.6 g, 63.4 mmole) in 60 mL THF at room temperature. This solution was stirred for 1 h and was then transferred via cannula into a stirred solution of 2-bromopyridine (3.8 mL, 39.6 mmole) and tetrakistriphenylphosphine palladium (0.22 g, 0.20 mmole) in 100 mL of THF. After stirring overnight at room temperature the mixture was quenched with saturated ammonium chloride solution (100 mL) and extracted with ether (3×100 mL). The combined ether extract was washed with brine (1×100 mL), dried over MgSO$_4$, filtered and concentrated in vacuo to yield 8.4 g of crude residue. The material was chromatographed (silica gel, 10% ether/hexanes) to yield 5.0 g (78%) of a pale yellow solid.

b) 2-Acetyl-5-(pyrid-2-yl)thiophene.

To a solution of 2-pyrid-2-ylthiophene from part a (1.0 g, 6.2 mmole) in 20 mL of THF at −78° C. was added n-butyllithium (2.6 mL, 6.5 mmole, 2.5M solution in hexanes). The solution was stirred for 30 min and then N-methoxy-N-methylacetamide (0.7 g, 6.8 mmole) was added via syringe. After approximately 2 h at −78° C. the material was quenched with saturated ammonium chloride solution (15 mL) and extracted with ethyl acetate (3×20 mL). The combined organic extract was washed with brine, dried with MgSO$_4$, filtered and concentrated. Chromatography (silica gel, 40% ether/hexanes) afforded 0.72 g (55%) of product.

c) N-hydroxy-N-(1-(5-pyrid-2-yl)ethyl urea.

The same method as described for Example 45 was used substituting 2-acetyl-5-(2-pyridyl)thiophene from part b instead of 2-thiophenecarboxaldehyde to provide the desired product. $^1$H NMR (300 MHz, DMSO-d$_6$) 9.20 (br s, 1H), 8.49 (m, 1H), 7.81 (m, 2H), 7.60 (d, 3.2 Hz, 1H), 7.23 (m, 1H), 6.96 (d, J=7.5, 14.4 Hz, 1H), 1.46 (d, J=7.2 Hz, 3H); MS (M+H)+ =264.

Analysis calc'd for C$_{12}$H$_{12}$N$_3$O$_2$S: C, 54.74; H, 4.98; N, 15.96. Found: C, 52.93; H, 4.87; N, 14.81.

EXAMPLE 49

Preparation of N-hydroxy-N-(3-methylthien-2-yl)methyl urea

The same method as described for Example 45 was used substituting 3-methylthien-2-ylcarboxaldehyde instead of 2-thiophenecarboxaldehyde to provide the desired product. m.p.=110° C.; $^1$H NMR (300 MHz, DMSO-d$_6$) 9.38 (br s, 1H), 7.28 (d, J=8.2 MHz, 1H), 6.81 (d, J=5.76 Hz, 1H), 6.35 (bs, 2H), 4.56 (br s, 2H), 2.17 (s, 3H); MS (M+H)+ =187; (M+NH$_4$)+ =204.

Analysis calc'd for C$_7$H$_{10}$N$_2$O$_2$S: C, 45.15; H, 5.41; N, 15.04. Found: C, 45.30; H, 5.46, N, 14.76.

EXAMPLE 50

Preparation of N-hydroxy-N-(thien-2-yl)methyl-N'-methyl urea

The same method as described for Example 45 was used substituting methylisocyanate for trimethylsilylisocyanate to provide the desired product. m.p.=108° C.; $^1$H NMR (300 MHz, DMSO-d$_6$): 9.35 (br s, 1H), 7.39 (dd, J=2.2, 5.4 Hz, 1H), 6.99–6.87 (m, 3H), 4.62 (br s, 2H), 2.58 (d, J=4.5 Hz); MS (M+H)+ =187, (M+NH$_4$)+ =204.

Analysis calc'd for C$_7$H$_{10}$N$_2$O$_2$S: C, 45.15; H, 5.41; N, 15.04. Found: C, 45.08; H, 5.38; N, 15.00.

EXAMPLE 51

Preparation of N-hydroxy-N-(5-methylthien-2-yl)methyl urea

The same method as described for Example 45 was used substituting 5-methylthien-2-yl carboxaldehyde instead of 2-thiophenecarboxaldehyde to provide the desired product. m.p.=134° C.; $^1$H NMR (300 MHz, DMSO-d$_6$): 9.36 (bs, 1H), 6.74 (d, J=3.3 Hz, 1H), 6.61 (m, 1H), 6.35 (bs, 2H), 4.52 (bs, 2H), 2.38 (s, 3H); MS (M+H)+ =187, (M+NH$_4$)+ =204.

Analysis calc'd for C$_7$H$_{10}$N$_2$O$_2$S: C, 45.15; H, 5.41; N, 15.04. Found: C, 45.37; H, 5.33; N, 14.94.

EXAMPLE 52

Preparation of N-hydroxy-N-1-(5-methylthien-2-yl)methyl-N'-methyl urea Formula I, R$_1$=H, R$_2$=CH$_3$, R$_3$=5 methylthien-2-yl, X=CH$_2$.

The same method as described for Example 45 was used substituting 5-methyl-2-thien-2-yl carboxaldehyde for 2-thiophenecarboxaldehyde and methylisocyanate for trimethylsilylisocyanate to provide the desired product. m.p.=120° C.; $^1$H NMR (300 MHz, DMSO-d$_6$): 9.30 (br s, 1H), 6.89 (m, 1H), 6.73 (d, J=3.1 Hz, 1H), 6.61 (m, 1H), 4.52 (br s, 2H), 2.58 (d, J=4.5 Hz, 3H), 2.38 (s, 3H); MS (M+H)+ =201, (M+NH$_4$)+ =218.

Analysis calc'd for C$_8$H$_{12}$N$_2$O$_2$S: C, 47.98; H, 6.04; N, 13.99. Found: C, 47.91; H, 5.96; N, 13.92.

EXAMPLE 53

Preparation of N-hydroxy-N-(1-(5-phenylthien-2-yl)methyl) urea a. 2-Phenylthiophene To a solution of thiophene (9.5 mL, 0.12 mole) in 100 mL tetrahydrofuran at 0° C. was added 2M n-butyllithium (48 mL, 0.12 mole) dropwise. The solution was stirred 2.5 h and was then added via cannula to a stirred solution of anhydrous zinc chloride (26 g, 0.19 mole) in 100 mL of THF at room temperature. After 1 h this solution was transferred via cannula into a solution of bromobenzene (8.4 mL, 0.08 mole) and tetrakis-triphenylphosphine palladium (0.2 g) in 100 mL of THF. The solution was warmed to reflux overnight. The solution was cooled to room temperature and quenched with saturated ammonium chloride solution. The mixture was extracted with ether (3×50 mL). The ether extracts were washed with brine, dried (MgSO$_4$), filtered and concentrated. The material was distilled (20 mm Hg) to yield 7.5 g (60%) of desired product, b.p.=150° C.

b. 5-Phenylthien-2-ylcarboxaldehyde

To a solution of dimethylformamide (13 mL, 0.17 mole) at 0° C. was added POCl$_3$ (4.4 mL, 0.05 mole) dropwise. To this was added 2-phenylthiophene (7.5 g, 0.05 mole) neat. The solution was warmed to 80° C. and allowed to stir overnight. The solution was cooled to room temperature and neutralized with saturated sodium acetate solution (100 mL). The mixture was washed with ether (3×50 mL). The ether extracts were washed with brine, dried (MgSO$_4$), filtered and concentrated. The resultant solid was recrystallized from hexanes to yield 5.03 g (57%) of the aldehyde.

c. N-hydroxy-N-1-(5-phenylthien-2-yl)methyl urea.

The same method as described for Example 45 was used substituting 5-phenyl-2-thien-2-ylcarboxaldehyde for 2-thiophenecarboxaldehyde to give the desired product. m.p.=174° C.; $^1$H NMR (300 MHz, DMSO-$d_6$) 9.50 (br s, 1H), 7.61 (m, 2H), 7.43-7.27 (m, 4H), 6.98 (d, J=3.3 Hz, 1H), 6.45 (br s, 2H), 4.63 (br s, 2H); MS: (M+H)$^+$=249, (M+NH4)$^+$=266.

Analysis calc'd for $C_{12}H_{12}N_2O_2S$: C, 58.05; H, 4.87; N, 11.28. Found: C, 57.55; H, 4.88; N, 11.14.

EXAMPLE 54

Preparation of
N-hydroxy-N-(1-(5-phenylthien-2-yl)methyl)-N'-methyl urea

The same method as described for Example 45 was used substituting 5-phenylthien-2-ylcarboxaldehyde for 2-thiophenecarboxaldehyde and methylisocyanate for trimethylsilylisocyanate to provide the desired product. m.p.=169° C.; $^1$H NMR (300 MHz, DMSO-$d_6$) 9.43 (br s, 1H), 7.60 (m, 2H), 7.43-7.26 (m, 4H), 6.98 (m, 2H), 4.63 (br s, 2H), 2.58 (d, J=5.5 Hz, 3H); MS (M+H)$^+$=263, (M+NH4)$^+$=280.

Analysis calc'd for $C_{13}H_{14}N_2O_2S$: C, 59.52; H, 5.38; N, 10.68. Found: C, 58.35; H, 5.30; N, 10.46.

EXAMPLE 55

Preparation of
N-hydroxy-N-(1-(5-(pyrid-2-yl)thien-2-yl)methyl) urea a) 2-Pyrid-2-ylthiophene To a solution of thiophene (4.7 mL, 59.4 mmole) at 0° C. was added 2.5M n-butyllithium (24 mL, 59.4 mmole) dropwise via syringe. The solution was stirred 3 h and was transferred via cannula into a stirred solution of zinc chloride (8.6 g, 63.4 mmole) in 60 mL THF at room temperature. This solution was stirred for 1 h and was transferred via cannula into a stirred solution of 2-bromopyridine (3.8 mL, 39.6 mmole) and tetrakis-triphenylphosphine palladium (0.22 g, 0.2 mmole) in 100 mL of THF. The solution was stirred overnight at room temperature and was then quenched with saturate ammonium chloride solution (100 mL) and extracted with ether (3×100 mL). The ether extracts were washed with brine (1×100 mL), dried over MgSO$_4$, filtered and concentrated to yield 8.4 g of crude residue. The material was chromatographed (silica gel, 10% ether/hexanes) to yield 5.0 g (78%) of a pale yellow solid.

b) 5-(2-Pyridyl)thien-2-ylcarboxaldehyde

To a solution of 2-(2-pyridyl)thiophene (2.0 g, 12.4 mmole) in 20 mL THF at −20° C. was added 2.5M n-butyllithium (6.0 mL, 15.0 mmole) and the bright red solution was stirred 1 h. To this solution was added dimethylformamide (4.8 mL, 62 mmole) and the solution was stirred 1 h. The reaction was quenched with saturated ammonium chloride solution (25 mL) and extracted with ethyl acetate (3×20 mL). The ethyl acetate extracts were washed with brine (1×30 mL), dried (MgSO$_4$), filtered and concentrated. The resultant red solid was chromatographed over silica gel (5% ether in dichloromethane) to give 1.4 g of the desired aldehyde.

c) N-hydroxy-N-(1-(5-pyrid-2-ylthien-2-yl)methyl) urea.

The same method as described for Example 45 was used substituting 5-(pyrid-2-yl)thien-2-ylcarboxaldehyde for 2-thiophenecarboxaldehyde to provide the desired product. m.p.=168° C.; $^1$H NMR (300 MHz, DMSO-$d_6$) 9.49 (br s, 1H), 8.49 (m, 1H), 7.82 (m, 2H), 7.61 (d, J=3.45 Hz, 1H), 7.23 (m, 1H), 6.99 (d, J=3.5 Hz, 1H), 6.42 (br s, 2H), 4.62 (br s, 2H); MS (M+H)$^+$=250. Analysis calc'd for $C_{11}H_{11}N_3O_2S$: C, 53.00; H, 4.45; N, 16.86. Found: C, 52.29; H, 4.45; N, 16.58.

EXAMPLE 56

Preparation of
N-hydroxy-N-(1-(5-phenylthien-2-yl)ethyl)urea a) 2-Acetyl-5-phenylthiophene, To a solution of 2-phenylthiophene (1.85 g, 11.5 mmol) and acetyl chloride (0.9 g, 11.5 mmol) in benzene (20 mL) at 0° C. was added SnCl$_4$ (3.0 g, 11.5 mmol) dropwise. The mixture was stirred for 1 h and allowed to warm to room temperature after which it was poured into cold 10% aqueous HCl. The mixture was extracted with ether. The organic extract was washed with brine, dried over MgSO$_4$, filtered, and concentrated to provide a solid which was purified by chromatography (silica gel, 1:3, ether, hexane) to give 1.8 g of a white powder.

b) The desired product was prepared by the same method described for Example 12, except using 2-acetyl-5-phenylthiophene instead of 2-acetyl-5-methylthiophene. m.p. 150°-151.5° C.; $^1$H NMR (300 MHz, DMSO-$d_6$) 1.46 (d, 3H, J=7.5 Hz), 5.49 (dd, 1H, J=15, 7.5 Hz), 6.43 (br s 2H), 6.95 (m, 1H), 7.30 (m, 2H), 7.40 (m, 2H), 7.60 (m, 2H), 9.21 (s, 1H); MS (M+H)$^+$=263, (M+NH4)$^+$=280.

EXAMPLE 57

Preparation of
N-hydoxy-N-(1-(5-benzylthien-2-yl)ethyl) urea a) 2-Benzylthiophene.

Thiophene (10 g, 120 mmol) was dissolved in THF (100 mL) and cooled to 0° C. n-BuLi (2.5 M in hexane, 48 mL, 120 mmol) was added dropwise and the mixture was stirred fo 1 h at 0° C. This solution was added via cannula to a solution of benzyl bromide (14 g, 79 mmol) and [(C$_6$H$_5$)$_3$P]$_4$Pd (0.46 g, 0.4 mmol) in THF (100 mL) at 0° C. The mixture was stirred at room temperature overnight, then pured into 10% aqueous HCl and extracted with ether. The organic extract was washed with brine, dried over MgSO$_4$, filtered, and concentrated. The residue was filtered through silica gel (100 g) with hexane as eluent and concentration gave a residue which was distilled to give 8 g of liquid, bp 88°-92° C. at 0.1 mm Hg.

b) The desired product was prepared according to the method described for Example 12 except using 2-acetyl-5-benzylthiophene which was in turn prepared according to the method described for 2-acetyl-5-phenylthiophene. m.p. 117°-120° C.; $^1$H NMR (300 MHz, DMSO-$d_6$) 1.37 (d, 3H, J=7.5 Hz), 4.06 (s, 2H), 5.39 (dd, 1H, J=15, 7.5 Hz), 6.43 (br s 2H), 6.71 (m, 2H), 7.27 (m, 5H), 9.10 (s, 1H); MS (M+H)$^+$=277, (M+NH4)$^+$=294.

Analysis calc'd for $C_{14}H_{16}N_2O_2S$: C, 60.85; H, 5.84; N, 10.14. Found: C, 60.58; H, 5.90; N, 9.78.

EXAMPLE 58

Preparation of
N-hydroxy-N-(1-(5-(2-phenylethenyl)thien-2-yl)ethyl) urea a) Trans 2-phenyl-1-(thien-2-yl)ethene Benzyldiethylphosphonate (5.7 g, 25 mmol) was dissolved in THF (50 mL) and cooled to −78° C. and nBuLi (2.5 M in hexane, 25 mmol) was added dropwise and the mixture was stirred for 30 min. Then a solution of thiophene-2-carboxaldehyde (2.8 g, 25 mmol) in THF (10 mL) was added dropwise at −78° C. The cold bath was removed and the reaction was warmed to room temperature, heated for 2 h at reflux and the reaction was then cooled and saturated aqueous NH₄Cl was added. The mixture was diluted with water and extracted with ether. The organic extract was washed with brine, dried over MgSO₄, filtered, and concentrated to provide a solid which was purified by recrystallization from hexane to give 2.6 g of intermediate.

b) Acetylation was accomplished according to the method used in Example 56. This intermediate was then converted to the desired compound according to the method described for Example 12. m.p. 160.5°–163° C.; $^1$H NMR (300 MHz, DMSO-d$_6$) 1.44 (d, 3H, J=7.5 Hz), 5.46 (dd, 1H, J=15, 7.5 Hz), 6.42 (br s 2H), 6.84 (d, 1H, J=12 Hz), 6.87 (m, 1H), 7.01 (m, 1H), 7.24 (m, 3H), 7.55 (m, 2H), 9.20 (s, 1H); MS (M+H)$^+$=289, (M+NH$_4$)$^+$=306.

Analysis calc'd for C$_{15}$H$_{16}$N$_2$O$_2$S: C, 62.48; H, 5.59; N, 9.71. Found: C, 62.73; H, 5.60; N, 9.43.

EXAMPLE 59

Preparation of N-hydroxy-N-(1-(2,5-dimethylthien-3-yl)ethyl)-N'-methylethoxycarbonyl urea To a stirred solution of 1-(2,5-dimethylthien-3-yl)ethylhydroxylamine (5.5 g, 32 mmol) in THF (25 mL) was added ethyl isocyanatoacetate (4.0 g, 31 mmol) dropwise under dry nitrogen. After stirring for one hour, the reaction was concentrated, the residue was dissolved in ethyl acetate (200 mL) and washed with 5% aqueous citric acid (100 mL). The organic layer was dried over MgSO₄ and concentrated. The resulting residue was purified by chromatography (silica gel, ethyl acetate-hexanes, 25:75, 40:60) followed by crystallization from ethyl acetate-hexanes to provide the desired product (5.03 g, 16.75 mmol) as white needles. m.p=111°–112.5° C.; NMR (300 MHz, DMSO-d$_6$) 1.17 (3H, t, J=7.0 Hz), 1.31 (3H, d, J=7.0 Hz), 2.27 (3H, s), 2.32 (3H, s), 3.73 (2H, m), 4.06 (2H, q, J=7.0 Hz), 5.23 (1H, q, J=7.0 Hz), 6.74 (1H, m), 7.13 (1H, t, J=6.1 Hz), 9.16 (1H, s); MS: (M+H)$^+$=301

Analysis Calc'd for C$_{13}$H$_{20}$N$_2$O$_4$S: C, 51.98; H, 6.71; N, 9.33. Found: C, 51.89; H, 6.65; N, 9.22.

EXAMPLE 60

Preparation of N-hydroxy-N-(1-(2,5-dimethylthien-3-yl)ethyl)-N'-(2-hydroxyethyl) urea To a stirred solution of ester from Example 59 (1.84 g, 6.13 mmol) in dry THF (15 mL) was added 2M lithium borohydride in THF (5.0 mL, 10.0 mmol) dropwise under nitrogen. The solution was stirred overnight, then quenched by the dropwise addition of methanol (25 mL) and stirred 4 h. The reaction was concentrated, poured into 10% aqueous citric acid (100 mL), and extracted with ethyl acetate (3×100 mL). The combined organic extract was dried over MgSO₄ and concentrated. The resulting residue was purified by chromatography (silica gel, ethyl acetate-hexanes, 50:50, 75:25), followed by crystallization from ethyl acetate-hexanes to provide the desired product. (510 mg). m.p=122°–123.5° C.; NMR (300 MHz, DMSO-d$_6$) 1.29 (3H, d, J=7.0 Hz), 2.28 (3H, s), 2.32 (3H, s), 3.08 (2H, m), 3.35 (2H, m), 4.65 (1H, t, J=5.3 Hz), 5.23 (1H, q, J=7.0 Hz), 6.70 (1H, t, J=5.9 Hz), 6.73 (1H, m), 9.03 (1H, s); MS: (M+H)$^+$=259

Analysis Calc'd for C$_{11}$H$_{18}$N$_2$O$_3$S: C, 51.14; H, 7.02; N, 10.84. Found: C, 51.07; H, 6.88; N, 10.63

EXAMPLE 61

Preparation of N-hydroxy-N-(1-thien-3-ylethyl)-N'-1-(4-carbomethoxybutyl) urea

To stirred solution of the mono-methyl ester of glutaric acid (2.0 mL, 15.2 mmol) in benzene(100 mL), triethylamine (2.23 mL, 16.0 mmol) and diphenylphosphoryl azide (3.37 mL, 15.2 mmol) were added. After refluxing 1 h, N-(1-thien-3-ylethyl) hydroxylamine (2.20 g, 15.4 mmol) was added. After 30 min the reaction was cooled to room temperature and poured into 10% HCl and extracted with EtOAc (2x). The combined organic extract was washed with H₂O and brine, dried (MgSO₄), and concentrated in vacuo. Purification by chromatography (silica gel, EtOAc/hexanes) followed by recrystallization from EtOAc/hexanes, gave 400 mg of desired product as a white solid. m.p. 84.5°–85.5° C.; NMR (300 MHz, DMSO-d$_6$) 1.38 (3H, d, 7.0 Hz), 1.65 (2H, quintet, J=7.5 Hz), 2.25 (2H, t, J=7.5 Hz), 3.05 (2H, q, J=7.5 Hz), 3.58 (3H, s), 5.28 (1H, q, J=7.0 Hz), 7.03 (2H, m), 7.26 (1H, m), 7.40 (1H, m), 8.98 (1H, s); MS (M+H)$^+$=287.

Analysis Calc'd for C$_{12}$H$_{18}$N$_2$O$_4$S: C, 50.33; H, 6.34; N, 9.78. Found: C, 50.16; H, 6.22; N, 9.78.

EXAMPLE 62

Preparation of N-hydroxy-N-(1-thien-3-ylethyl-N'-(methylethoxycarbonyl)urea

To a stirred solution of the 1-thien-3-ylethylhydroxylamine (1.43 g, 10 mmol) in THF (12 mL) was added ethyl isocyanatoacetate (1.44 g, 11.1 mmol) dropwise under dry nitrogen. Workup as described above for Example 59, purification by chromatography (silica gel, ethyl acetate-hexanes, 25:75, 40:60) followed by crystallization from ethyl acetate-hexanes provided the desired product (2.68 g, 9.84 mmol) as white crystals. m.p.=86.5°–88° C.; NMR (300 MHz, DMSO-d$_6$) 1.19 (3H, t, J=7.0 Hz), 1.41 (3H, d, J=7.0 Hz), 3.73 (2H, d, J=6.3 Hz), 4.09 (2H, q, J=7.0 Hz), 5.30 (1H, q, J=7.0 Hz), 7.06 (1H, dd, J=5.1, 1.3 Hz), 7.29 (2H, m), 7.42 (1H, dd, J=5.1, 2.9 Hz), 9.17 (1H, s); MS: (M+H)$^+$=273.

Analysis Calc'd for C$_{11}$H$_{16}$N$_2$O$_4$S: C, 48.52; H, 5.92; N, 10.29. Found: C, 48.4; H, 6.01; N, 10.19.

EXAMPLE 63

Preparation of N-hydroxy-N-(1-(1-(5-methylthien-2-yl)-2-hydroxy)ethyl) urea a) 1-(5-Methylthien-2-yl)-2-hydroxyethanone To a stirred solution of diisopropylamine (3.18 g, 31.4 mmol) at −78° C. in 150 mL THF, was added dropwise n-butyllithium (12.56 mL of a 2.5M solution in hexanes, 31.4 mmol). After complete addition, the solution was stirred for 30 mins at that temperature. A sample of 2-acetyl-5-methylthiophen (4.00 g, 28.6 mmol) in 10 mL THF was then added and the reaction was stirred for an additional 30 mins at −78° C. Chlorotrimethylsilane (3.41 g, 31.4 mmol) was then added, the mixture was stirred 30 mins at −78° C. and then diluted with aqueous sat'd NaHCO₃ (150 mL) and extracted with ethylacetate (3×150 mL). The combined organic extracts were dried with MgSO₄ and concentrated.

The resulting residue from above was taken up in 100 mL CH₂Cl₂ containing 50 mL aqueous sat'd NaHCO₃, and cooled to 0° C. and m-chloroperoxybenzoic acid (6.17 g, 80% purity, 28.6 mmol) was added and the mixture was stirred for 45 mins at 0° C. It was then diluted with aqueous. sat'd NaHCO₃ (50 mL) and extracted with CH₂Cl₂ (3×150 mL). The combined organic extract was dried with MgSO₄ and concentrated to a volume of 150 mL. To this was added 4 spatulas of Amberlyst-15 ion exchange resin and the heterogeneous mixture was stirred for 1 hr. It was then filtered and concentrated. The resulting residue was purified by chromatography (silica gel, ether-hexanes, 3:7) to provide 2.91 g of the desired product.

b) N-hydroxy-N-(1-(1-(5-methylthien-2-yl)-2-hydroxy)ethyl) urea.

The same method as described for Example 45 was used substituting 1-(5-methylthien-2-yl)-2-hydroxyethanone instead of 2-thiophene-carboxaldehyde to provide the desired product. mp.=140.0°-141.5° C.; NMR (300 MHz, DMSO-d₆) 2.38 (s, 3H), 3.59 (m, 1H), 3.75 (m, 1H), 4.64 (dd, 1H, J=6 Hz), 5.26 (dd, 1H, J=6 Hz), 6.32 (s, 2H), 6.61 (dd, 1H, J=2 Hz), 6.71 (d, 1H, J=3.5 Hz), 9.08 (s, 1H); MS: M+=217.

Analysis Calc'd for C₈H₁₂N₂O₃S: C, 44.43; H, 5.60; N, 12.96. Found: C, 44.33; H, 5.50; N, 12.85

EXAMPLE 64

Preparation of
N-hydroxy-N-(1-(5-methylthien-2-yl)-5-carboethoxypentyl) urea a) Adipoyl chloride monoethyl ester To a stirred solution of adipic acid monoethyl ester (3.14 g, 18.0 mmol), was added dropwise oxalyl chloride (2.51 g, 19.8 mmol) and the resulting mixture was stirred for 18 h and then concentrated and used as follows.

b) Ethyl 6-keto-(5-methylthien-2-yl)hexanoate

To a stirred solution of 2-methylthiophene (1.767 g, 18.0 mmol) in 90 mL THF at −78° C., was added n-butyllithium (7.20 mL of a 2.5M solution in hexanes, 18.0 mmol) dropwise. The resulting mixture was stirred for 30 min. then MnI₂ (5.78 g, 18.72 mmol) was added (preparation according to G. Friour, G. Cahiez, J. F. Normant, Synthesis, 1984, 37). The cooling bath was withdrawn and the reaction allowed to warm to room temperature and stirred for 30 mins. It was then cooled to 0° C. and adipoyl chloride monoethyl ester from above (18.0 mmol) was added as a solution in 10 mL THF. The cooling bath was withdrawn and the reaction allowed to warm to room temperature and stirred for 3 h. The mixture was diluted with aqueous sat'd NaHCO₃ (90 mL) and extracted with ethyl acetate (3×90 mL). The combined organic extract was dried with MgSO₄ and concentrated. The resulting residue was purified by chromatography (silica gel, ether-hexanes, 15:85) to afford 2.84 g of the desired product as an oil.

c) N-hydroxy-N-(1-(5-methylthien-2-yl)-5-carboethoxypentyl) urea

The same method as described for Example 45 was used substituting ethyl 6-(5-methylthien-2-yl)-6-ketohexanoate instead of 2-thiophene-carboxaldehyde to provide the desired product. mp.=106°-107° C.; NMR (300 MHz, DMSO-d₆) 1.14-1.42 (m, 2H), 1.48-1.59 (m, 2H), 1.62-1.76 (m, 1H), 1.77-1.90 (m, 1H), 2.28 (t, 2H, J=7.5 Hz), 2.37 (s, 3H), 3.57 (s, 3H), 5.19 (t, 1H, J=7.5 Hz), 6.30 (br s, 2H), 6.59 (m, 1H), 6.69 (d, 1H, J=3.5 Hz), 9.07 (s, 1H); MS: M+=301.

EXAMPLE 65

Preparation of
N-hydroxy-N-(1-(5-methylthien-2-yl)-6-carboxyamidohexyl) urea a) A solution of ethyl 6-oxo-6-(5-methylthien-2-yl)hexanoate (1.45 g, 5.5 mmol) in 30 mL 1:1 aqueous 1N LiOH: THF was stirred for 5 h. The mixture was diluted with water (10 mL) and washed with ethyl acetate (2×25 mL). The aqueous layer was acidified to pH2 with aqueous 6N HCl and extracted with ethylacetate (3×25 mL). These last organic extracts were combined, dried with MgSO₄, and concentrated to afford 1.08 g (87%) of the desired intermediate.

b) To a stirred solution of the intermediate from part a) (1.07 g, 4.7 mmol) in 23 mL CH₂Cl₂, was added oxalyl chloride (721 mg, 5.7 mmol). After stirring for 72 h, the reaction was concentrated in vacuo. The resulting residue was taken up in a minimum amount of THF and was added dropwise to a solution of 10% aqueous NH₄OH (20 mL) The reaction was stirred for 1 h., diluted with brine (10 mL) and extracted with ethylacetate (3×30 mL). The combined organic extract was dried with MgSO₄ and concentrated to afford 1.02 g of intermediate amide.

c) The same method as described for Example 45 was used substituting 6-oxo-6-(5-methylthien-2-yl)hexamide instead of 2-thiophene-carboxaldehyde to provide the desired product. mp.=172° C. (dec); NMR (300 MHz, DMSO-d₆) 1.11-1.25 (m, 1H), 1.25-1.39 (m, 1H), 1.49 (m, 2H), 1.62-1.75 (m, 1H), 1.75-1.90 (m, 1H), 2.01 (t, 2H, J=8 Hz), 2.38 (s, 3H), 5.19 (t, 1H, J=7.5 Hz), 6.59 (m, 1H), 6.69 (d, 1H, J=3.5 Hz); MS: M+=286.

Analysis Calc'd for C₁₂H₁₉N₃O₃S: C, 50.51; H, 6.71; N, 14.73. Found: C, 50.41; H, 6.68; N, 14.59.

EXAMPLE 66

Preparation of
N-hydroxy-N-(1-(1-(2-hydroxy))-5-methylthien-2-yl)propyl) urea a) 1-(5-Methylthien-2-yl)-1-propanol To a solution of 5-methylthien-2-ylcarboxaldehyde (2.52 g, 20 mmol) in 100 mL ether at 0° C., was added ethylmagnesium bromide (8.00 mL of a 3.0M solution in ether, 24 mmol) dropwise. The cooling bath was withdrawn and the reaction was allowed to warm to room temperatureafter which it was quenched with aqueous sat'd NH₄Cl (100 mL) and extracted with ethylacetate (3×100 mL). The combined organic extreact was dried with MgSO₄ and concentrated to afford the desired product.

b) 1-(5-Methylthien-2-yl)propanone

A solution of 1-(5-methylthien-2-yl)propanol from above (20 mmol) and pyridinium dichromate (9.03 g, 24 mmol) in 100 mL CH₂Cl₂ was stirred for 18 h. The reaction was then filtered through Celite and the filtrate was concentrated. The resulting residue was purified by chromatography (silica gel, etherhexanes, 1:9) to afford 1.86 g (60% over the two steps) of the desired product.

c) N-hydroxy-N-(1-(1-(5-methylthien-2-yl))-2-hydroxypropyl) urea.

The same method as described for Example 12 was used substituting 1-(5-methylthien-2-yl)propanone instead of 2-acetyl-5-methylthiophene to provide the desired product. Upon purification by chromatography (silica gel, ether-methanol, 9:1) separation of the two diastereomers were achieved. mp.=160°-161° C.; NMR (300 MHz, DMSO-$d_6$) 0.92 (d, 3H, J=6.5 Hz), 2.38 (s, 3H), 3.94 (m, 1H), 4.37 (d, 1H, J=5 Hz), 4.92 (d, 1H, J=9 Hz), 6.31 (bs, 2H), 6.61 (dd, 1H, J=2 Hz), 6.71 (d, 1H, J=3.5 Hz), 9.01 (s, 1H); MS: M+ =231.

Analysis Calc'd for $C_9H_{14}N_2O_3S$: C, 46.94; H, 6.13; N, 12.17. Found: C, 47.16; H, 6.23; N, 12.15.

EXAMPLE 67

Preparation of N'-methyl-N-hydroxy-N-(1-(1-(2-hydroxy))-5-(methylthien-2-yl)ethyl) urea The same method as described for Example 66 was used substituting methyl isocyanate for trimethylsilyl isocyanate. mp.=100.5°-102.0° C.; NMR (300 MHz, DMSO-$d_6$) 2.37 (s, 3H), 2.56 (d, 3H, J=4.5 Hz), 3.53-3.63 (m, 1H), 3.71-3.81 (m, 1H), 4.62 (dd, 1H, J=6 Hz, J=7 Hz), 5.74 (t, 1H, J=7.5 Hz), 6.60 (m, 1H), 6.70 (d, 1H, J=4 Hz), 6.84 (q, 1H, J=4 Hz), 9.02 (s, 1H); MS : M+ =231.

Analysis Calc'd for $C_9H_{14}N_2O_3S \cdot \frac{1}{2}H_2O$: C, 45.17; H, 6.32; N, 11.71 Found: C, 45.02; H, 6.37; N, 11.67

EXAMPLE 68

Preparation of N-hydroxy-N-(3-(1-thien-3-yl)propenyl) urea a) 3-(Thien-2-yl)acrolein To a solution of 2N NaOH (99 mL, 11.2 mmole) at room temperature was added dropwise 3-thiophenecarboxaldehyde (3.9 mL, 44.6 mmole). The solution was stirred until homogeneous (10 min), cooled to 0° C. and acetaldehyde (2.7 mL, 49.0 mmole) in 5 mL water was added slowly. After 30 min the solution was extracted with ether (3×50 mL). The ether extracts were washed with brine and dried over MgSO4, filtered and concentrated to yield a crude yellow oil. The material was chromatographed (silica gel, 30% ether/hexanes) to yield 1.65 g (27%) of pure material and 1.91 g of a 3:1 mixture of desired product and diene aldehyde.

b) N-hydroxy-N-(3-(1-thien-3-yl)propenyl) urea.

The same method as described for Example 45 was used substituting 3-thien-2-yl acrolein for 2-thiophenecarboxaldehyde to provide the desired product. m.p.=151° C.; $^1$H NMR (300 MHz, DMSO-$d_6$) 9.30 (br s, 1H), 7.50 (m, 1H), 7.42 (m, 1H), 7.30 (m, 1H), 6.56 (d, J=15.3 Hz, 1H), 6.35 (br s, 2H), 6.09 (m, 1H), 4.03 (m, 2H); MS (M+H)+ =199, (M+NH4)+ =216.

Analysis calc'd for $C_8H_{10}N_2O_2S$: C, 48.47; H, 5.08; N, 14.13. Found: C, 48.29; H, 5.11; N, 13.99.

EXAMPLE 69

Preparation of N-hydroxy-N-(3-(1-thien-3-yl)propyl) urea

To a stirred solution of 10% Pd/C (0.36 g) in 50 mL of ethyl acetate was added N-hydroxy-N-3-(1-(thien-3-yl)propenyl) urea (0.26 g, 1.31 mmole) in 50 mL of methanol. The solution was hydrogenated at room temperature under hydrogen (4 atm) for 2.5 h. The solution was then filtered, concentrated and the crude solid was recrystallized from ethyl acetate/hexanes to yield white crystalline product. m.p. =97.5° C.; $^1$H NMR (300 MHz, DMSO-$d_6$) 9.24 (br s, 1H), 7.44 (m, 1H), 7.13 (m, 1H), 6.99 (m, 1H), 6.23 (br s, 2H), 3.33 (t, J=6.6 Hz, 14.6 Hz, 2H), 2.57 (t, J=7.3 Hz, 15.3 Hz, 2H), 1.78 (m, 2H).

Analysis calc'd for $C_8H_{12}N_2O_2S$: C, 47.98; H, 6.04; N, 13.99. Found: C, 47.50; H, 5.83; N, 13.78.

EXAMPLE 70

Preparation of N-Hydroxy-N-(1-thien-3-ylethyl) thiourea

The same method as described for Example 43 was used except trimethylsilylisothiocyanate was used instead of trimethylsilylisocyanate. mp. =158° C. Dec., NMR (300 MHz, DMSO-d6) 1.46 (3H, d, J=7.5 Hz), 6.55 (1H, q, J=7.5 Hz), 7.10 (1H, m), 7.32 (1H, m), 7.45(1H, m), 7.8 (2H, brs), 9.58 (1H, brs); MS: (M+H)+ =203, (M+NH4)+ =220

EXAMPLE 71

Preparation of N-Hydroxy-N-[1-(5-methylthien-2-yl) ethyl] thiourea

The same method as described for Example 12 except trimethylsilylisothiocyanate was used instead of trimethylsilylisocyanate. mp.=155° C. Dec., NMR (300 MHz, DMSO-d6) 1.46 (3H, d, J=7.5 Hz), 2.38 (3H, s), 6.63 (2H, m), 6.29 (1H, m), 7.32 (1H, m), 7.42 (1H,brs), 7.82 (1H, brs), 9.62 (1H, brs); MS: (M+H)+ =217, (M+NH4)+ =234.

EXAMPLE 72

Preparation of N-Hydroxy-N-(2-(1-(5-methylthien-2-yl)) propyl) urea a) To a stirred solution of 5-methyl-2-thiophenecarboxaldehyde (10 g, 79.4 mmol) in methanol was added nitroethane (6.8 mL, 95.2 mmol, 1.2 eq), followed by a catalytic amount of n-butylamine. The reaction was heated to reflux for four days. The reaction was cooled, the solvent was evaporated, and the residue was partitioned between water and $CH_2Cl_2$. The organic layer was dried over MgSO4 and evaporated. The resulting residue was purified by Chromatography (silica gel, 10% ethyl acetate-hexane) yielding 4.5 g of a yellow solid.

b) To a flamed dried, nitrogen flushed 250 mL flask, equipped with a magnetic stir bar, and a reflux condenser at at 0° C., was added BH3THF (1M, 11.2 mmol, 11.2 mL). The product obtained in a (1.9 g, 11.2 mmol, in 20 mL THF) was added slowly via syringe. The cold bath was removed and a catalytic amount of NaBH4 was added. After 2 hours passed 100 mL of ice-water was added followed by 20 mL of 10% HCl. The reaction was heated to 65° C. for 2 hours before cooling to room temperature. The acidic solution was washed with ether (3×50 mL) and the hydroxylamine was liberated from the aqueous layer with 2N NaOH. Extraction of the neutralized solution with ethyl acetate, drying of the combined organic layers with MgSO4, and evaporation gave a clean, clear oil (558 mg).

c) The formation of the urea was performed as in Example 12. Purification of the product was done using radial chromatography (4 mm plate, 3% methanol-methylene chloride). 300 mg of a solid was obtained. mp. =96°-98° C., $^1$H NMR (300 MHz, DMSO-d6) 0.98 (3H, d), 2.37 (3H, s), 2.80 (2H, m), 4.25 (1H, m), 6.30 (2H, br s) 6.62 (2H, m), 8.98 (1H, s); MS: (M+H)+ =215, (M+NH4)+ =232.

EXAMPLE 73

Preparation of
N-hydroxy-N-4(4,5,6,7-tetrahydro-thianaphthalene) urea

To a stirred solution of 4-keto-4,5,6,7,-tetrahydrothianaphthalene (5.0 g, 32.8 mmole) in ethanol/pyridine (1:1, 50 mL) was added hydroxylamine hydrochloride (4.5 g, 65.7 mmole). The reaction was stirred 24 h at room temperature and diluted with 3N HCl. The resulting solid was collected and washed thoroughly with water and dried to give 3.86 g of the corresponding oxime as a white solid. This material was used without further purification.

To a stirred solution of oxime (3.68 g, 22.7 mmole) in ethanol was added borane.pyridine (5.27 g, 56.7 mmole) followed by 6N HCl (25 mL) via a dropping funnel at a rate to maintain a gentle reflux. After the addition the mixture was stirred 5 h at room temperature and then concentrated in vacuo. The residue was neutralized with 3N NaOH (~pH 10). The resulting solid was collected by filtration, washed thoroughly with water and dried to give 3.22 g of the corresponding hydroxylamine as a white solid.

To a stirred solution of the hydroxylamine from above (3.0 g, 17.7 mmole) in THF (50 mL) was added trimethylsilylisocyanate (2.55 g, 22.16 mmole). The reaction was stirred 2 h at room temperature and poured into saturated ammoninium chloride solution and the mixture was extracted with ethyl acetate (3×20 mL). The combined organic layer was washed with brine, dried (MgSO4), filtered and concentrated. The resulting solid was recrystallised from ethyl acetate to give 2.25 g of desired product as a white solid: mp 165°-167° C.; $^1$H NMR (300 MHz) (DMSO-d$_6$) d 1.65-1.89 (m, 3H), 1.97-2.10 (m, 1H), 2.68 (m, 2H), 5.18 (m, 2H), 6.41 (bs, 2H), 6.74 (d, 1H, J=6 Hz), 7.20 (d, 1H, J=6 Hz), 8.95 (s, 1H); MS m/e 242 (M+NH4)+, 225 (M+H)+.

EXAMPLE 74

Preparation of
N-hydroxy-N-[(4-bromo-thien-3-yl)methyl]urea

To a −78° C. stirred solution of 3,4-dibromothiophene (10 g, 41.33 mmole) in THF (25 mL) was added n-BuLi (45.5 mmole, 2.5M in hexanes). The reaction was stirred 5 min. and cannulated into a cold (−78° C.) stirred solution of DMF (4.35 g, 62 mmole) in THF (20 mL). The reaction was allowed to stir overnight at room temperature, poured into dilute HCl and extracted with ethyl acetate. The combined organic layers were washed with water, dried (MgSO4) and concentrated to give a brown oil. Distillation yielded 2.31 g (29%) of 4-bromothien-3-yl carboxaldehyde as a liquid (bp: 65°, 0.5 mm Hg).

To a stirred solution of the aldehyde from above (2.31 g, 12.15 mmole) in ethanol/pyridine (1:1, 40 mL) was added hydroxylamine hydrochloride (1:67 g, 24.32 mmole). The reaction was stirred 2 h at room temperature, concentrated and diluted with 3N HCl. The mixture was extracted with ethyl acetate (3×75 mL) and dried (MgSO4). Concentration gave an oil that crystallised upon addition of ethyl acetate/hexane. The crystals were collected to give 0.68 g of the corresponding oxime.

To a stirred solution of oxime from above (0.65 g, 3.17 mmole) in ethanol was added borane.pyridine (0.59 g, 6.34 mmole) followed by 6N HCl (7 mL) via a dropping funnel at a rate to maintain a gentle reflux. After the addition the mixture was stirred 0.5 h at room temperature and then concentrated in vacuo. The residue was neutralized with 3N NaOH (~pH 10) and extracted with ethyl acetate. The combined organic layers were washed with water, dried (MgSO4) and concentrated to give 0.68 g of the corresponding hydroxylamine.

To a stirred solution of the hydroxylamine from above (0.54 g, 2.22 mmole) in THF (25 mL) was added trimethylsilylisocyanate (0.45 g, 3.33 mmole). The reaction was stirred 2 h at room temperature and poured into saturated ammonium chloride solution and the mixture was extracted with ethyl acetate (3×20 mL). The organic layer was washed with brine, dried (MgSO4), filtered and concentrated. The resulting solid was purified by chromatography (5% MeOH/CH2Cl2) to give 0.32 g of the desired product as a white solid: mp 134°-135.5° C.; $^1$H NMR (300 MHz) (DMSO-d$_6$) d 4.63 (s, 2H), 6.48 (bs, 2H), 7.02 (d, 1H, J=6 Hz), 7.58 (d, 1H, J=6 Hz), 9.53 (s, 1H); MS m/e 268 (M+NH4)+, 251 (M+H)+.

EXAMPLE 75

Preparation of
N-hydroxy-N-[1-(thien-3-yl)propen-2-yl]urea

In a 100 mL round bottom flask equipped with a dropping funnel under an argon atmosphere were dissolved 1-(thien-3-yl)1-hydroxy-2-propene (1.01 g, 7.20 mmole), triphenylphosphine (1.82 g, 9.0 mmole), and N,O-bis benzyloxycarbonyl hydroxylamine (2.38 g, 7.921 mmole) in THF (50 mL). To this stirred cooled (~15° C.) solution was added slowly over a period of 30 min a THF (15 mL) solution of diisopropylazodicarboxylate (2.36 g, 9.00 mmole) via a dropping funnel. After the addition was complete the reaction was stirred an additional 15 min and then concentrated in vacuo. The residue was dissolved in 50% ethyl acetate/hexane (~10 mL) and loaded onto a short silica gel column and eluted with 33% ethyl acetate/hexane. The fractions containing the product were combined and reconcentrated. The residue was loaded onto another flash column and eluted with 5% ethyl acetate/hexane to give 0.97 g of the diCBZ hydroxylamine derivative.

To a 0° C. stirred solution of the diCbz derivative (3.10 g, 7.3 mmole) in CH2Cl2 (150 mL) was added trimethylsilyl iodide (4.39 g, 22 mmole) via syringe. The ice bath was removed and the reaction allowed to stir for 2 h at room temperature. The reaction was then poured into ice/sodium bicarbonate and the layers separated. The aqueous layer was washed with CH2Cl2 (3×50 mL); the organic layers were combined, washed with water, dried(MgSO4) and concentrated. The residue was purified by flash column chromotography; eluting first with CH2Cl2 (to remove benzyliodide) then 5% MeOH/CH2Cl2 to afford 0.61 g of the corresponding hydroxylamine as a brown solid.

To a stirred solution of hydroxylamine (0.6 g, 3.87 mmole) in THF (10 mL) was added trimethylisocyanate (0.56 g, 4.87 mmole). The reaction was stirred 2 h at room temperature and 5 drops of water were added. The mixture was concentrated to dryness and the residue was triturated with ether to provide a tan solid which was collected by filtration and washed with ether. The resulting solid was recrystallised from ethyl acetate/hexanes to give 0.190 g of the desired product. mp 165°-167° C.; $^1$H NMR (300 MHz) (DMSO-d$_6$) d 5.20–5.35 (m, 2H), 5.74 (d, 1H, J=6 Hz), 6.08–6.22 (m, 1H), 6.40 (bs, 2H), 7.03 (dd, 1H), 7.28 (m, 1H), 7.45 (dd, 1H), 9.20 (s, 1H); MS m/e 216 (M+NH4)+, 199 (M+H)+, 123.

EXAMPLE 76

Preparation of N-hydroxy-N-(1-(5-(2-thien-2-ylethenyl)thien-2-yl)ethyl)-urea

The desired material is prepared in a similar manner as Example 58 substituting benzyldiethylphosphonate with thien-2-ylmethyldiethyl-phosphonate.

EXAMPLE 77

Preparation of N-hydroxy-N-(1-(5-(2-pyrid-2-ylethenyl)thien-2-yl)ethyl)-urea

The desired material is prepared in a similar manner as Example 58 substituting benzyldiethylphosphonate with pyrid-2-ylmethyldiethyl-phosphonate.

EXAMPLE 78

Preparation of N-hydroxy-N-(1-(5-(2-thien-3-ylethenyl)thien-2-yl)ethyl)-urea

The desired material is prepared in a similar manner as Example 58 substituting benzyldiethylphosphonate with thien-3-ylmethyldiethylphos-phonate.

EXAMPLE 79

Preparation of N-hydroxy-N-(1-(5-(4-chlorophenylethen-2-yl)thien-2-yl)-ethyl)urea The desired material is prepared in a similar manner as Example 58 substituting benzyldiethylphosphonate with 4-chlorobenzyldiethylphos-phonate.

EXAMPLE 80

Preparation of N-hydroxy-N-(2-(1-thien-3-yl)propyl)urea

The desired material is prepared in a similar manner as Example 72 substituting 5-methylthien-2-yl carboxaldehyde with thien-3-yl carbox-aldehyde.

EXAMPLE 81

Preparation of N-hydroxy-N-(2-(1-thien-2-yl)propyl)urea

The desired material is prepared in a similar manner as Example 72 substituting 5-methylthien-2-yl carboxaldehyde with thien-2-yl carboxaldehyde.

EXAMPLE 82

Preparation of N-hydroxy-N-(2-(1-(5-pyrid-2-yl)thien-2-yl)propyl)urea

The desired material is prepared in a similar manner as Example 72 substituting 5-methylthien-2-yl carboxaldehyde with (5-pyrid-2-yl)thien-3-yl carboxaldehyde.

EXAMPLE 83

Preparation of N-hydroxy-N-(2-(1-(5-phenylethen-2-yl)thien-2-yl)propyl)-urea

The desired material is prepared in a similar manner as Example 72 substituting 5-methylthien-2-yl carboxaldehyde with (5-phenylethen-2-yl)thien-2-yl carboxaldehyde.

EXAMPLE 84

Preparation of N-hydroxy-N-(2-(1-(5-benzylthien-2-yl)propyl)urea

The desired material is prepared in a similar manner as Example 72 substituting 5-methylthien-2-yl carboxaldehyde with 5-benzylthien-3-yl carboxaldehyde.

EXAMPLE 85

Preparation of N-Hydroxy-N-(thien-3-yl)methyl urea potassium salt

The material prepared as in example 44 is dissolved in tetrahydrofuran and one equivalent of potassium hydride is added. After hydrogen evolution ceases, the solvent is removed in vacuo to yield the desired product.

EXAMPLE 86

Preparation of N-hydroxy-N-(3-(1-thien-3-yl)propenyl) urea potassium salt

The material prepared as in example 68 is dissolved in tetrahydrofuran and one equivalent of potassium hydride is added. After hydrogen evolution ceases, the solvent is removed in vacuo to yield the desired product.

EXAMPLE 87

Preparation of N-ethoxycarbonyloxy-N-(thien-3-yl)methy urea

The material prepared as in Example 44 is dissolved in dichloromethane and treated with triethylamine and ethoxycarbonylchloride. Aqueous workup and evaporation of the organic extract provides the desired product.

EXAMPLE 88

Preparation of N-ethoxycarbonyloxy-N-(3-(1-thien-3-yl)propenyl) urea

The material prepared as in Example 68 is dissolved in dichloromethane and treated with triethylamine and ethoxycarbonylchloride. Aqueous workup and evaporation of the organic extract provides the desired product.

EXAMPLE 89

Preparation of N-trimethylsilyloxy-N-(thien-3-yl)methyl urea

The material prepared as in Example 44 is dissolved in dichloromethane and treated with trimethylsilylimidazole. Evaporation of mixture and addition of ether precipitates imidazole which is filtered. Evaporation of the ether provides the desired product.

EXAMPLE 90

Preparation of N-Hydroxy-N-(thien-3-yl)methyl-N'-phenyl urea

The desired compound is prepared by the same method as described for Example 44 except using phenylisocyanate instead of trimethylsilylisocyanate. 1

EXAMPLE 91

Preparation of
N,N'-dihydroxy-N-(thien-3-yl)methyl-N'-methyl urea

The desired material is prepared in a similar manner as described for Example 10, except using thien-3-yl carboxyaldehyde instead of 2-acetonaphthone in part a. and methylhydroxylamine hydrochloride instead of hydroxylamine hydrochloride in part b.

EXAMPLE 92

Preparation of
N,N'-dihydroxy-N-1-(thien-3-yl)ethyl-N'-methyl urea

The desired material is prepared in a similar manner as described for Example 10, except using 3-acetylthiophene instead of 2-acetonaphthone in part a. and methylhydroxylamine hydrochloride instead of hydroxylamine hydrochloride in part b.

EXAMPLE 93

Preparation of
N,N'-dihydroxy-N-1-(5-phenylthien-2-yl)ethyl urea

The desired material is prepared in a similar manner as described for Example 10, except using 2-acetyl-5-phenylthiophene instead of 2-acetonaphthone in part a.

EXAMPLE 94

Preparation of
N-Hydroxy-N-1-(6-methoxynaphthalen-2-yl)ethyl urea

The desired material is prepared in a similar manner as described for Example 1 except using 6-methoxy-2-acetonaphthone instead of acetophenone.

EXAMPLE 95

Preparation of
N-Hydroxy-N-(6-methoxynaphthalen-2-yl)methyl urea

The desired material is prepared in a similar manner as described for Example 1 except using 6-methoxynaphthalen-2-yl carboxyaldehyde instead of acetophenone.

EXAMPLE 96

Preparation of
N-Hydroxy-N-3-(1-(6-methoxynaphthalen-2-yl)propenyl) urea

The desired material is prepared in a similar manner as described for Example 68 except using 6-methoxynaphthalen-2-yl carboxyaldehyde instead of 3-thiophene carboxyaldehyde.

EXAMPLE 97

Preparation of
N-Hydroxy-N-1-(4-bromophenyl)ethylurea

To a solution of 3.90 g (20 mmol) of p-bromoacetophenone in 40 mL of methanol under nitrogen at room was added a solution of 1.64 g (23.6 mmol) of hydroxylamine hydrochloride and 3.34 g (24.6 mmol) of sodium acetate trihydrate in 20 mL of water. After 2 h, evaporate the methanol, add more water, extract with 3×35 mL of ether, dry over magnesium sulfate, filter and evaporate to give 4.27 g of a mixture of oxime geometric isomers. IR (CDCl$_3$) 3580, 3300, 1590, 1490, 1010, 825 cm$^{-1}$; $^1$H NMR (CDCl$_3$) 2.28 (s, 3), 7.49 (m, 4) ppm; mass spectrum m/e (rel intensity) 231 and 233 (35, M$^+$+NH$_4$), 214 and 216 (100, M$^+$+H).

To a solution of 2.9 g (13.6 mmol) of the crude hydroxylamine from above in 70 mL of ethanol was added 3.0 mL (29.7 mmol) of borane pyridine complex. After stirring under nitrogen at room temperature for 30 min there was added 54 mL (32.7 mmol) of 6N HCl and the resulting solution was allowed to stir overnight. After 18 h the solution was basified with 1N KOH, diluted with brine, extracted with 2×100 mL of methylene chloried, dried over magnesium sulfate, filtered, evaporated, and crystallized. Column chromatography with 4/1 hexane/ether elution gave 1.75 g of the desired hydroxylamine. IR (CDCl$_3$) 3580, 3280, 2980, 1595, 1487 cm$^{-1}$; $^1$H NMR (CDCl$_3$) 1.34 (d, 3, J=7 Hz), 4.08 (q, 1, J=7 Hz), 5.45 (br s, 2), 7.21 (d, 2, J=8 Hz), 7.46 (d, 2, J=8 Hz) ppm; mass spectrum m/e (rel intensity) 233 and 235 (12, M$^+$+NH$_4$), 216 and 218 (100, M$^+$+H), 200 and 202 (40, M$^+$−Me), 183 and 185 (60), 104 (85).

To a solution of 1.7 g (7.9 mmol) of the hydroxylamine from above in 40 mL of dry THF was added under nitrogen at room temperature 1.3 mL (9.6 mmol) of 85% trimethylsilylisocyanate. After 2 h there was added 25 mL of saturated aqueous ammonium chloride and after stirring for 30 min the reaction was diluted with 25 mL of water, extracted with 3×50 mL of ethyl acetate, dried over magnesium sulfate, filtered, evaporated, and recrystallized from ether (using a small amount of THF and acetonitrile as cosolvent) to give 0.30 g of the title compound. mp 138°–40° C.; IR (CDCl$_3$) 3445, 3240, 1660, 1575, 1490, 1430 cm$^{-1}$; $^1$H NMR (d$_6$Me$_2$SO) 1.40 (d, 3J=7 Hz), 5.26 (q, q,1,J=7 Hz), 6.31 (br s, 2), 7.29 (d, 2, J=8 Hz), 7.49 (d, 2, J=8 Hz), 9.10 (s, 1) ppm; mass spectrum m/e (rel intensity) 276 and 278 (70, M$^+$+NH$_4$), 259 and 261 (100, M$^+$+H), 243 and 245 (18), 200 (90).

Analysis calculated for C$_9$H$_{11}$BrN$_2$O$_2$: C, 41.72, H, 4.28, N, 10.81; found: C, 41.67, H, 4.31, N, 10.77.

EXAMPLE 98

Preparation of
N-Hydroxy-N-1-(4-bromophenyl)ethyl-N'-methylurea.

The compound was prepared using the method of Example 97 except for the substitution of methylisocyanate for trimethylsilylisocyanate. mp 129°–30° C.; IR (CDCl$_3$) 3400, 3200, 1650, 1600, 1535 cm$^{-1}$; $^1$H NMR (d$_6$ Me$_2$SO) 1.39 (d, 3, J=7 Hz), 2.57 (d, 3, J=4 Hz), 5.22 (q, 1, J=7 Hz), 6.82 (br s, 1), 7.27 (d, 2, J=8 Hz), 7.48 (d, 2, J=8 Hz), 9.00 (s, 1) ppm; mass spectrum m/e (rel intensity) 2.90 and 2.92 (70, M$^+$+N$_4$), 274 and 276 (100, M$^+$+NH$_4$-O), 273 and 275 (35, M$^+$+H), 257 and 259 (80, M$^+$-Me).

Analysis calculated for C$_{10}$H$_{13}$BrN$_2$O$_2$: C, 43.98, H, 4.80, N, 10.26; found: C, 43.98, H, 7.78, N, 10.26.

EXAMPLE 99

Preparation of
N-Hydroxy-N-1-(4-bromophenyl)ethyl-N'-(2-hydroxyethyl)-urea.

The compound was prepared using the method of Example 97 substituting ethyl isocyanatoacetate for trimethylsilyl isocyanate to provide 1.7 g of the ethyl ester. mp 131°–5° C.; IR (CDCl$_3$) 3690, 3530, 3440, 2980, 1740, 1670, 1520, 1210 cm$^{-1}$; $^1$H NMR (d$_6$ Me$_2$SO) 1.19 (t, 3, J=7 Hz), 1.90 (d, 3, J=7 Hz), 3.70 (dd, 1, J=6, 18 Hz), 3.78 (dd, 1, J=6, 18 Hz), 4.06 (q, 2, J=7 Hz), 5.23 (q, 1, J=7 Hz), 7.25 (t, 1, J=6 Hz), 7.29

(d, 2, J=9 Hz) 7.48 (d, 2, J=9 Hz) 9.27 (s, 1) ppm; mass spectrum m/e (rel intensity) 362 and 364 (10, M+ +NH4), 345 and 347 (100, M+ +H), 200 (25), 183 and 185 (22), 163 (18), 104 (85).

To a solution of 1.7 g (4.9 mmol) of the ester from above in 10 mL of THF at room temperature under nitrogen was added 3.5 mL (7 mmol) of 2M lithium borohydride in THF. After 3 h the reaction was poured into 25 mL of saturated ammonium chloride solution, extracted with 3×50 mL of methylene chloride, dried ofver magnesium sulfate, filtered, evaporated and recrystallized from THF/hexane to give 1.0 g of the desired compound. mp 117°-9° C.; IR (KBr) 3320, 2925, 1625, 1525 cm$^{-1}$; $^1$H NMR (d$_6$ Me$_2$SO) 1.38 (d, 3, J=7 Hz), 3.08 (m, 4), 4.63 (m, 1), 5.23 (q, 1, J=7 Hz), 6.80 (m, 1), 7.28 (d, 2, J=8 Hz), 7.49 (d, 2, J=8 Hz), 9.10 (br s, 1) ppm; mass spectrum m/e (rel intensity) 303 and 305 (50, M+ +NH4), 287 and 289 (7), 216 and 218 (18), 200 (28), 183 and 185 (22), 145 (21), 105 (100).

Analysis calculated for C$_{11}$H$_{15}$BrN$_2$O$_2$: C, 43.58, H, 4.99, N, 9.24; found: C, 44.30, H, 5.13, N, 9.05.

EXAMPLE 100

Preparation of N-Hydroxy-N-4-bromobenzylurea

The compound was prepared using the method of Example 97 substituting p-bromobenzaldehyde for p-bromoacetophenone. mp 157°-9° C.; IR (KBr) 3420, 3140, 2880, 1645, 1545 cm$^{-1}$; $^1$H NMR (d$_6$ Me$_2$SO) 4.48 (s, 2), 6.38 (br s, 2), 7.23 (d, 2, J=8 Hz) 7.50 (d, 2, J=8 Hz) 9.38 (s, 1) ppm; mass spectrum m/e (rel intensity) 262 and 264 (35, M+ +NH4), 245 and 247 (100, M+ +H), 229 (32), 186 (40), 169 and 171 (18), 106 (30).

Analysis calculated for C$_8$H$_9$BrN$_2$O$_2$: C, 39.21, H, 3.70, N, 11.43; found: C, 39.48, H, 3.69, N, 11.34.

EXAMPLE 101

Preparation of N-Hydroxy-N-4-bromobenzyl-N'-methyl urea

The compound was prepared using the method of Example 97 substituting p-bromobenzaldehyde for p-bromoacetophenone, and substituting methyl isocyanate for trimethylsilyl isocyanate. mp 165°-7° C.; IR (CDCl$_3$) 3480, 3180, 2900, 1660, 1620, 1580 cm$^{-1}$; $^1$H NMR (d$_6$ Me$_2$SO) 2.61 (d, 3, J=5 Hz), 4.47 (s, 2), 6.90 (q, 1, J=5 Hz), 7.22 (d, 2, J=8 Hz), 7.50 (d, 2, J=8 Hz), 9.30 (s, 1) ppm; mass spectrum m/e (rel intensity) 276 and 278 (20, M+ +NH4), 259 and 261 (100, M+ +H), 243 (60), 241 (45), 186 (35), 106 (40).

Analysis calculated for C$_9$H$_{11}$BrN$_2$O$_2$: C, 41.72, H, 7.28, N, 10.81; found: C, 41.77, H, 4.21, N, 10.79.

EXAMPLE 102

Preparation of N-Hydroxy-N-(1-(4-bromophenyl)propyl) urea

The compound was prepared using the method of Example 97 substituting 4-bromopropiophenone for 4-bromoacetophenone. mp 139°-41° C.; IR (KBr) 3490, 3325, 3160, 1640, 1560, 1485 cm$^{-1}$; $^1$H NMR (d$_6$ Me$_2$SO) 0.88 (t, 3, J=7 Hz), 1.70-2.00 (m, 2), 4.97 (dd, 1, J=6, 9 Hz), 6.25 (s, 2), 7.27 (d, 2, J=8 Hz), 7.46 (d, 2, J=8 Hz), 9.10 (s, 1) ppm; mass spectrum m/e (rel intensity) 290 and 292 (20, M+ +NH4), 273 and 275 (100, M+ +H), 257 (10), 214 (15), 197 and 199 (15).

Analysis calculated for C$_{10}$H$_{13}$BrN$_2$O$_2$: C, 43.97, H, 4.80, N, 10.26; found: C, 43.96, H, 4.84, N, 10.18.

EXAMPLE 103

Prepration of N-Hydroxy-N-(1-(4-bromophenyl)propyl)-N'-methylurea

The compound was prepared using the method of Example 97 substituting p-bromopropiophenone for p-bromoacetophenone, and substituting methyl isocyanate for trimethylsilyl isocyanate. mp 110°-2° C.; IR (KBr) 3400, 3170, 1640, 1620, 1535 cm$^{-1}$; $^1$H NMR (d$_6$ Me$_2$SO) 0.87 (t, 3, J=7 Hz), 1.70-2.00 (m, 2), 2.55 (d, 3, J=7 Hz), 4.94 (dd, 1, J=6, 9 Hz), 6.79 (q, 1, J=7 Hz), 7.25 (d, 2, J=8 Hz), 7.46 (d, 2, J=8 Hz), 9.00 (s, 1) ppm; mass spectrum m/e (rel intensity) 304 and 306 (10, M+ +NH4), 287 and 289 (100, M+ +H), 271 (14).

Analysis calculated for C$_{11}$H$_{15}$BrN$_2$O$_2$: C, 46.01, H, 5.27, N, 9.76; found: C, 45.92, H, 5.16, N, 9.76.

EXAMPLE 104

Preparation of N-Hydroxy-N-(1-(2,4-difluorophenyl)ethyl)-N'-methylurea

The compound was prepared using the method of Example 97 substituting 2,4-difluoroacetophenone for p-bromoacetophenone, and substituting methyl isocyanate for trimethylsilyl isocyanate. mp 125°-34° C.; IR (KBr), 3460, 3140, 1635, 1535, 1500 cm$^{-1}$; $^1$H NMR (d$_6$ Me$_2$SO) 1.38 (d, 3, J=7 Hz), 2.58 (d, 3, J=4.5 Hz), 5.49 (q, 1, J=7 Hz), 6.90 (q, 1, J=4.5 Hz), 7.03 (ddt, 1, J=1,2,9 Hz), 7.14 (dt, 1, J=2, 9 Hz), 7.54 (dt, 1, J=6, 9 Hz), 9.10 (s, 1) ppm; mass spectrum m/e (rel intensity) 248 (100, M+ +NH4), 231 (50, M+ +H), 215 (20), 213 (18).

Analysis calculated for C$_{10}$H$_{12}$F$_2$N$_2$O$_2$: C, 52.17, H, 5.25, N, 12.17; found: C, 51.81, H, 5.29, 12.21.

EXAMPLE 105

Preparation of N-Hydroxy-N-(1-(4-(2-phenylethynyl)phenyl)ethyl) urea

The compound was prepared using the method of Example 97 substituting 4-(2-phenylethynyl)acetophenone for p-bromoacetophenone. mp 144°-6° C.; IR (KBr) 3450, 1650 cm$^{-1}$; $^1$H NMR (d$_6$ Me$_2$SO) 1.42 (d, 3, J=7 Hz), 5.30 (q, 1, J=7 Hz), 6.33 (s, 2), 7.30-7.60 (m, 9), 9.13 (s, 1) ppm; mass spectrum m/e (rel intensity) 298 (20, M+ +NH4), 281 (100, M+ +H), 263 (12), 205 (75).

Analysis calculated for C$_{17}$H$_{16}$N$_2$O$_2$: C, 72.84, H, 5.75, N, 10.00; found: C, 72.49, H, 5.73, N, 9.99.

EXAMPLE 106

Preparation of N-Hydroxy-N-(1-(4-(2-phenylethynyl)phenyl)ethyl)-N'-methyl urea

The compound was prepared using the method of Example 97 substituting 4-(2-phenylethynyl)acetophenone for p-bromoacetophenone, and substituting methyl isocyanate for trimethylsilyl isocyanate. mp 138°-41° C.; IR (KBr) 3400, 3160, 2880, 1630, 1535 cm$^{-1}$; $^1$H NMR (d$_6$ Me$_2$SO) 1.42 (d, 3, J=7 Hz), 2.60 (d, 3, J=5 Hz), 5.29 (q, 1, J=7 Hz), 6.85 (q, 1, J=5 Hz), 7.30-7.60 (m, 9), 9.02 (s, 1) ppm; mass spectrum m/e (rel intensity) 312 (10, M+ +NH4), 295 (100, M+ +H), 279 (8), 277 (8), 205 (45).

Analysis calculated for C$_{18}$H$_{18}$N$_2$O$_2$: C, 73.44, H, 6.16, N, 9.52; found: C, 73.14, H, 6.18, 9.57.

EXAMPLE 107

Preparation of N-Hydroxy-N-(1-(4-chlorophenyl)ethyl) urea

The compound was prepared using the method of Example 97 substituting p-chloroacetophenone for p-bromoacetophenone. mp 125°-8° C.; IR (KBr) 3480, 3300, 2900, 1660, 1630, 1490 cm$^{-1}$; $^1$H NMR (d$_6$ Me$_2$SO) 1.39 (d, 3, J=7 Hz), 5.27 (q, 1, J=7 Hz), 6.31 (br s, 2), 7.33 (s, 4), 9.10 (s, 1) ppm; mass spectrum m/e (rel intensity) 232 (83, M$^+$+NH$_4$), 215 (100, M$^+$+H), 199 (20), 197 (15), 156 (38), 154 (25).

Analysis calculated for C$_9$H$_{11}$ClN$_2$O$_2$: C, 50.36, H, 5.17, N, 13.05; found: C, 50.39, H, 5.18, N, 13.02.

EXAMPLE 108

Preparation of N-Hydroxy-N-(1-(4-chlorophenyl)ethyl)-N'-methyl urea

The compound was prepared using the method of Example 97 substituting p-chloroacetophenone for p-bromoacetophenone, and substituting methyl isocyanate for trimethylsilyl isocyanate. mp 117°-20° C.; IR (KBr) 3400, 3200, 1630, 1530 cm$^{-1}$; $^1$H NMR (d$_6$ Me$_2$SO) 1.38 (d, 3, J=7 Hz), 2.58 (br s, 3), 5.23 (q, 1, J=7 Hz), 6.32 (br s, 1), 7.32 (s, 4), 9.00 (s, 1) ppm; mass spectrum m/e (rel intensity) 248 (35, M$^+$+NH$_4$), 246 (100, M$^+$+NH$_4$), 229 (8, M$^+$+H).

Analysis calculated for C$_{10}$H$_{13}$ClN$_2$O$_2$: C, 52.52, H, 5.73, N, 12.25; found: C, 51.87, H, 5.40, N, 12.11.

EXAMPLE 109

Preparation of N-Hydroxy-N-(1-(4-fluorophenyl)ethyl) urea

The compound was prepared using the method of Example 97 substituting p-fluoroacetophenone for p-bromoacetophenone. mp 127°-9° C.; IR (KBr) 3480, 3345, 3120, 2880, 1620, 1510, 1225 cm$^{-1}$; $^1$H NMR (d$_6$ Me$_2$SO) 1.40 (d, 3, J=7 Hz), 5.28 (q, 1, J=7 Hz), 6.31 (s, 2), 7.11 (t, 2, J=9 Hz), 7.37 (dd, 2, J=6, 9 Hz), 9.07 (s, 1) ppm; mass spectrum m/e (rel intensity) 216 (90, M$^+$+NH$_4$), 199 (100, M$^+$+H), 183 (14), 181 (11), 156 (8), 140 (18), 138 (19), 123 (7).

Analysis calculated for C$_9$H$_{11}$FN$_2$O$_2$: C, 54.54, H, 5.59, N, 14.13; found: C, 54.40, H, 5.58, N, 14.12.

EXAMPLE 110

Preparation of N-Hydroxy-N-(1-(4-fluorophenyl)ethyl)-N'-methyl urea

The compound was prepared using the method of Example 97 substituting p-fluoroacetophenone for p-bromoacetophenone, and substituting methyl isocyanate for trimethylsilyl isocyanate. mp 130°-3° C.; IR (KBr) 3380, 3250, 1645, 1510 cm$^{-1}$; $^1$H NMR (d$_6$ Me$_2$SO) 1.39 (d, 3, J=7 Hz), 2.55 (br s, 3), 5.25 (q, 1, J=7 Hz), 6.82 (br s, 1), 7.10 (br t, 2, J=8 Hz), 7.35 (br t, 2, J=6 Hz), 8.96 (br s, 1) ppm; mass spectrum m/e (rel intensity) 230 (100, M$^+$+NH$_4$) 214 (38), 213 (8, M$^+$+H), 197 (5), 157 (8), 155 (3), 138 (11).

Analysis calculated for C$_{10}$H$_{13}$FN$_2$O$_2$: C, 56.60, H, 6.17, N, 13.20; found: C, 56.04, H, 5.84, N, 12.97.

EXAMPLE 111

Preparation of N-Hydroxy-N-(1-(4-trifluoromethylphenyl)ethyl) urea

The compound was prepared using the method of Example 97 substituting p-trifluoromethylacetophenone for p-bromoacetophenone. mp 133°-5° C.; IR (KBr) 3470, 3280, 2900, 1670, 1635, 1330, 1120 cm$^{-1}$; $^1$H NMR (d$_6$ Me$_2$SO) 1.43 (d, 3, J=7 Hz), 5.36 (q, 1, J=7 Hz), 6.38 (s, 2), 7.55 (d, 2, J=8 Hz), 7.66 (d, 2, J=8 Hz), 9.19 (s, 1) ppm; mass spectrum m/e (rel intensity) 266 (100, M$^+$+NH$_4$), 249 (60, M$^+$+H), 233 (13), 231 (20), 207 (18), 206 (17), 190 (40), 188 (35).

Analysis calculated for C$_{10}$H$_{11}$F$_3$N$_2$O$_2$: C, 48.39, H, 4.47, N, 11.29; found: C, 48.44, H, 4.50, N, 11.31.

EXAMPLE 112

Preparation of N-Hydroxy-N-(1-(4-trifluoromethylphenyl)ethyl)-N'-methyl urea

The compound was prepared using the method of Example 97 substituting p-trifluoromethylacetophenone for p-bromoacetophenone, and substituting methyl isocyanate for trimethylsilyl isocyanate. mp 124°-5° C.; IR (KBr) 3420, 3380, 3240, 2900, 1660, 1605, 1535, 1325, 1334, 1170, 1130, 1120 1070 cm$^{-1}$; $^1$H NMR (d$_6$ Me$_2$SO) 1.42 (d, 3, J=7 Hz), 2.59 (d, 3, J=5 Hz), 5.33 (q, 1, J=7 Hz), 6.90 (q, 1, J=5 Hz), 7.55 (d, 2, J=9 Hz), 7.66 (d, 2, J=9 Hz), 9.10 (s, 1) ppm; mass spectrum m/e (rel intensity) 280 (60, M$^+$+NH$_4$), 263 (100, M$^+$+H), 247 (38), 245 (50), 190 (25), 188 (30).

Analysis calculated for C$_{11}$H$_{13}$F$_3$N$_2$O$_2$: C, 50.39, H, 5.00, 10.68; found: C, 50.21, H, 4.91, N, 10.65.

EXAMPLE 113

Preparation of N-Hydroxy-N-(1-(4-methylphenyl)ethyl) urea

The compound was prepared using the method of Example 97 substituting p-methylacetophenone for p-bromoacetophenone. mp 134°-5° C.; IR (KBr) 3460, 3180, 2880, 1660, 1570, 1480 cm$^{-1}$; $^1$H NMR (d$_6$ Me$_2$SO) 1.38 (d, 3, J=7 Hz), 2.26 (s, 3), 5.25, (q, 1, J=7 Hz), 6.27 (s, 2), 7.09 (d, 2, J=8 Hz), 7.21 (d, 2, J=8 Hz), 9.00 (s, 1) ppm; mass spectrum m/e (rel intensity) 212 (40, M$^+$+NH$_4$), 195 (100, M$^+$+H), 179 (18), 177 (13), 136 (30), 134 (43), 119 (26).

Analysis calculated for C$_{10}$H$_{14}$N$_2$O$_2$: C, 61.84, H, 7.26, N, 14.42.

EXAMPLE 114

Preparation of N-Hydroxy-N-(1-(3-bromo-4-fluorophenyl)ethyl)-N'-methyl urea

The compound was prepared using the method of Example 97 substituting 3-bromo-4-fluoroacetophenone for p-bromoacetophenone, and substituting methyl isocyanate for trimethylsilyl isocyanate. mp 137°-8° C.; IR (KBr) 3370, 3240, 1640, 1530, 1495 cm$^{-1}$; $^1$H NMR (d$_6$Me$_2$SO) 1.38 (d, 3, J=7 Hz), 2.57 (d, 3, J=4.5 Hz), 5.26 (q, 1, J=7 Hz), 6.91 (q, 1, J=4.5 Hz), 7.30 (t, 1, J=8 Hz), 7.33 (ddt, 1, J=2, 5, 9 Hz), 7.61 (dd, 1, J=2, 7 Hz), 9.09 (s, 1) ppm; mass spectrum m/e (rel intensity) 308 and 310 (43, M$^+$+NH$_4$), 294 (85), 292 (100), 275 (60).

Analysis calculated for C$_{10}$H$_{12}$BrFN$_2$O$_2$: C, 41.26, H, 4.15, N, 9.62; found: C, 41.46, H, 4.12, N, 9.68.

EXAMPLE 115

Preparation of
N-Hydroxy-N-(1-(3-bromo-4-methylphenyl)ethyl)-N'-methyl urea

The compound was prepared using the method of Example 97 substituting 3-bromo-4-methylacetophenone for p-bromoacetophenone, and substituting methyl isocyanate for trimethylsilyl isocyanate. mp 107°-8° C.; IR (KBr) 3460, 3180, 1640, 1515 cm$^{-1}$; $^1$H NMR (d$_6$ Me$_2$SO) 1.37 (d, 3, J=7 Hz), 2.31 (s, 3), 2.57 (d, 3, J=4 Hz), 5.22 (q, 1, J=7 Hz), 6.87 (q, 1, J=4 Hz), 7.22 (dd, 1, J=1.5, 8 Hz), 7.27 (d, 1, J=8 Hz), 7.50 (d, 1, J=1.5 Hz), 9.04 (s, 1) ppm; mass spectrum m/e (rel intensity) 304 and 306 (100, M+ +NH$_4$), 288 and 290 (35), 287 and 289 (38, M+ +H), 271 (35).

Analysis calculated for C$_{11}$H$_{15}$BrN$_2$O$_2$: C, 46.01, H, 5.26, N, 9.75; found: C, 45.29, H, 5.19, N, 9.58.

EXAMPLE 116

Preparation of
N-Hydroxy-N-(1-(4-methoxyphenyl)ethyl) urea

The compound was prepared using the method of Example 97 substituting p-methoxyacetophenone for p-bromoacetophenone. mp 132°-4° C.; IR (KBr) 3440, 3200, 1660, 1580, 1520, 1455, 1445, 1245 cm$^{-1}$; $^1$H NMR (d$_6$ Me$_2$SO) 1.37 (d, 3, J=7 Hz), 3.73 (s, 3), 5.24 (q, 1, J=7 Hz), 6.25 (s, 2), 6.85 (d, 2, J=8 Hz), 7.25 (d, 2, J=8 Hz), 8.98 (s, 1) ppm; mass spectrum m/e (rel intensity) 228 (100, M+ +NH$_4$), 212 (36), 211 (35, M+ +H), 135 (12).

Analysis calculated for C$_{10}$H$_{14}$N$_2$O$_3$: C, 57.13, H, 6.71, N, 13.32; found: C, 57.29, H, 6.71, N, 13.41.

EXAMPLE 117

Preparation of
N-Hydroxy-N-(1-(4-methoxyphenyl)ethyl)-N'-methyl urea

The compound was prepared using the method of Example 97 substituting p-methoxyacetophenone for p-bromoacetophenone, and substituting methyl isocyanate for trimethylsilyl isocyanate. mp 102.5°-4° C.; IR (CDCl$_3$) 3540, 3460, 3200, 2940, 1670, 1515, 1250 cm$^{-1}$; $^1$H NMR (d$_6$ Me$_2$SO) 1.36 (d, 3, J=7 Hz), 2.56 (d, 3, J=4 Hz), 5.22 (q, 1, J=7 Hz), 6.78 (q, 1, J=4 Hz), 6.84 (d, 2, J=8 Hz), 7.24 (d, 2, J=8 Hz), 8.88 (s, 1) ppm; mass spectrum m/e (rel intensity) 242 (100), M+ +NH$_4$), 226 (100), 225 (70, M+ +H), 209 (75), 207 (100).

Analysis calculated for C$_{11}$H$_{16}$N$_2$O$_3$: C, 58.91, H, 7.19, N, 12.49; found: C, 58.91, H, 7.18, N, 12.57.

EXAMPLE 118

Preparation of
N-Hydroxy-N-(1-(4-phenoxyphenyl)ethyl) urea

A solution of p-phenoxybromobenzene (4.98 g, 20 mmol) at −78° C. in dry THF (50 mL) was treated under nitrogen with n-BuLi (8 mL, 2.5M in hexanes, 20 mmol) and the mixture was stirred for 30 min. A solution of nitrone (prepared by modification of the method reported in *Acta. Chim. Acad. Sci. Hung.* 1958, 14, 333, by the treatment of 5-hydroxypentanal oxime (3.5 g, 30 mmol) with acetaldehyde (3.4 mL, 60 mmol) in the presence of CaCl$_2$ (17.4 g, 130 mmol) at 0° C. in dichloromethane for 6 h, filtered, and dichloromethane evaporated in vacuo at 0° C.) in THF precooled to 0° C. (50 mL) was added to the cold anion (−78° C.) and stirred for 30 min after removal of the cold bath. Ethanol (50 mL) and 6N HCl (5 mL) was added and the mixture was stirred for 1.5 h at 40° C. and at room temperature overnight. Concentrate, add 150 mL of water, wash with either, basify with sodium carbonate, extract with 2×100 mL of ether, dry over magnesium sulfate, filter, and evaporate to provide the crude hydroxlyamine which was acylated using trimethylsilyl isocyantate as described in Example 98. mp 118°-9° C.; $^1$H NMR (d$_6$ Me$_2$SO) 1.40 (d, 3, J=7 Hz), 5.28 (q, 1, J=7 Hz), 6.31 (s, 1), 6.96 (m, 4), 7.22 (t, 1, J=7 Hz), 7.35 (m, 4), 9.05 (s, 1) ppm; mass spectrum m/e 290 (M+ +NH$_4$), 273 (M+ +H).

Analysis calculated for C$_{15}$H$_{16}$N$_2$O$_3$: C, 66.15, H, 5.92, N, 10.29; found; C, .62.57, H, 6.20, N, 9.96.

EXAMPLE 119

Preparation of
N-Hydroxy-N-(1-(4-butoxyphenyl)ethyl) urea

The compound was prepared using the method of Example 97 substituting p-butoxyacetophenone for p-bromoacetophenone. mp 137°-8.5° C.; $^1$H NMR (CDCl$_3$) 0.97 (t, 3, J=7 Hz), 1.46 (m, 2), 1.53 (d, 3, J=7 Hz), 1.76 (m, 2), 3.94 (t, 2, J=7 Hz), 5.23 (br s, 2), 5.42 (q, 1, J=7 Hz), 6.71 (s, 1), 6.85 (d, 2, J=8 Hz), 7.32 (d, 2, J=8 Hz) ppm; mass spectrum m/e 252, 235, 192, 177, 121.

Preparation of N-Hydroxy-N-(1-(4-biphenyl)ethyl) urea

The compound was prepared using the method of Example 98 substituting p-phenylacetophenone for p-bromoacetophenone. After the hydroxylamine had bee prepared it was acylated in toluene by preparing the hydrochloride salt (HCl gas), heating to reflux, gassing with phsgene for about three minutes, continue to reflux for about one hour, then cool and pour into cold ammonium hydroxide. The crude material thus obtained was presumed to be diacylated, therefore, it was treated with about 2.5 equivalents of lithium hydroxide in isopropanol. After work-up and recrystallization from ethanol/water there was obtained a 32% yield of the desired hydroxy urea. mp 157°-8° C.; $^1$H NMR (d$_6$ Me$_2$SO) 1.44 (d,3,J=7.5 Hz), 5.33 (q,1, J=7.5 Hz), 6.34 (br s, 2), 7.50 (m, 9), 9.12 (br s, 1) ppm; mass spectrum m/e 274 (M+ +NH$_4$), 257 (,M+ +NH$_4$), 257 (,M+ +H).

EXAMPLE 121

Preparation of
N-Hydroxy-N-(1-(4-bis-allylaminophenyl) ethyl) urea

The compound was prepared using the method of Example 98 substituting p-(bisallylamino)acetophenone for p-bromoacetophenone. mp 112°-4° C.; $^1$H NMR (d$_6$ Me$_2$SO) 1.33 (d, 3,J=7 Hz), 3.89 (m, 4), 5.09-5.22 (m, 5), 5.76-5.90 (m, 2), 6.28 (br s, 2), 6.58 (m, 2), 7.10 (m, 2), 8.88 (s, 1) ppm; mass spectrum m/e 276 (M+ +H), 200.

EXAMPLE 122

Preparation of
N-Hydroxy-N-(1-(3-bromo-4-fluorophenyl) ethyl) urea

The compound was prepared using the method of Example 97 substituting 3-bromo-4-fluoroacetophenone for p-bromoacetophenone. mp 125°-7°° C.; IR (KBr) 3460, 3300, 1660, 1630, 1495 cm$^{-1}$; $^1$H NMR (d$_6$ Me$_2$SO) 1.39 (d, 3, J=7 Hz), 5.28 (q, 1, J=7 Hz), 6.39 (bs, 2), 7.30 (t, 1, J=8 Hz), 7.34 (dt, 1, J=2,8 Hz), 7.62

(dd, 1, J=2,7 Hz), 9.18 (s, 1) ppm; mass spectrum m/e 294 and 296 (M++NH4), 278 and 280 (M++H).

Analysis calculated for C9H10BrFN2O2: C, 39.01, H 3.64, N, 10.11; found: C, 39.14, H, 3.68, N, 10.15.

EXAMPLE 123

Preparation of
N-Hydroxy-N-(1-(4-chloro-3-methylphenyl) ethyl) urea

The compound was prepared using the method of Example 97 substituting 4-chloro-3-methylacetophenone for p-bromoacetophenone. mp 129°-31° C.; IR (KBr) 3460, 3300, 1630, 1560, 1480, 1440 cm⁻¹; ¹H NMR (d6 Me2SO) 1.38 (d, 3, J=7 Hz), 2.31 (s, 3), 5.25 (q, 1, J=7 Hz), 6.33 (bs, 2), 7.17 (m, 1), 7.33 (m, 2), 9.08 (s, 1) ppm; mass spectrum m/e (rel intensity) 229 and 231 (100 and 40, M++H), 170 (78), 153 (75).

Analysis calculated for C10H13ClN2O2: C, 52.52, H, 5.73, N, 12.25; found: C, 52.72, H, 5.71, N, 12.27.

EXAMPLE 124

Preparation of
N-Hydroxy-N-(1-(4-chloro-3-methylphenyl)ethyl)-N'-methyl urea

The compound was prepared using the method of Example 97 substituting 4-chloro-3-methylacetophenone for p-bromoacetophenone, and substituting methyl isocyanate for trimethylsilyl isocyanate. mp 99°-102° C.; IR (KBr) 3440, 3200, 1640, 1535 cm⁻¹; ¹H NMR (d6 Me2SO) 1.37 (d,3,J=7 Hz), 2.30 (s, 3), 2.57 (d,3,J=4 Hz), 5.22 (q,1,J=7 Hz), 6.85 (bq, 1,J=4.5 Hz), 7.16 (dd, 1,J=2,8 Hz), 7.30 (d, 1,J=2 Hz), 7.32 (d, 1,J=8 Hz), 8.98 (s, 1) ppm; mass spectrum m/e (rel intensity) 260 and 262 (50 and 18, M++NH4), 243 and 245 (100 and 35, M++H).

Analysis calculated for C11H15ClN2O2: C,54.44, H, 6.23, N, 11.54; found: C, 54.33, H, 6.30, N, 11.54.

EXAMPLE 125

Preparation of
N-Hydroxy-N-(1-(4-chloro-3-methylphenyl) ethyl) urea

The compound was prepared using the method of Example 97 substituting 3-phenoxybenzaldehyde for p-bromoacetophenone. mp 155°-6° C.; IR (KBr) 3480, 3200, 1660, 1620, 1590, 1490, 1450, 1260 cm⁻¹; ¹H NMR (d6Me2SO) 4.51 (s, 2), 6.39 (s, 2), 6.32-7.42 (m, 9), 9.39 (s, 1) ppm; mass spectrum m/e (rel intensity) 276 (25, M++NH4), 259 (100, M++H), 216 (28), 200 (40), 183 (38). Analysis calculated for C14H14N2O3: C, 65.11, H, 5.46, N, 10.85; found: C, 64.53, H, 5.42, N, 10.81.

EXAMPLE 126

Preparation of
N-Hydroxy-N-(1-(4-chloro-3-methylphenyl)ethyl-N'-methyl urea

The compound was prepared using the method of Example 97 substituting 3-phenoxybenzaldehyde for p-bromoacetophenone, and substituting methyl isocyanate for trimethylsilyl isocyanate. mp 124°-6° C.; IR (KBr) 3340, 3180, 1630, 1575, 1545, 1485, 1220 cm⁻¹; ¹H NMR (d6 Me2SO) 2.59 (d, 3, J=5 Hz), 4.50 (s, 2), 6.84-7.41 (m, 10), 9.30 (s, 1) ppm; mass spectrum m/e (rel intensity) 290 (15, M++NH4), 273 (100, M++H), 257 (60), 198 (40), 183 (40).

Analysis calculated for C15H16N2O3: C, 66.16, H, 5.92, N, 10.29; found: C, 66.16, H, 5.94, N, 10.27.

EXAMPLE 127

Preparation of
N-hydroxy-N-(3-bromothien-2-yl)methyl urea

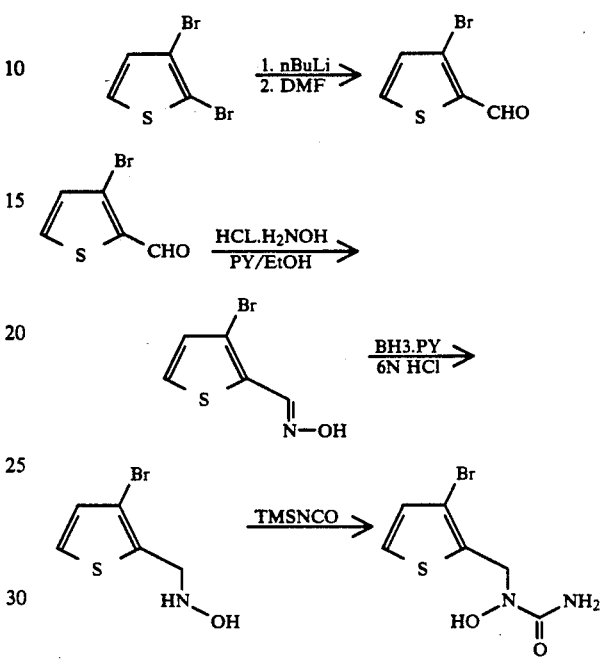

a) Preparation of 3-bromothiophene-2-carboxaldehyde.

To a cold (−78° C., dry ice/acetone) solution of 2,3-dibromothiophene (10 g, 41.3 mMol) in ether (75 mL) was added n-butyllithium (19.35 mL, 48.36 mMol, 2.5M in hexanes). The reaction was stirred for 5 min and cannul ated into a cold stirred solution of N,N-dimethylformamide (4.53 g, 61.99 mMol) in ether (25 mL). The reaction was stirred 1 h at −78° C. and then allowed to warm to room temperature. Water (5 mL) was added cautiously while stirring. The reaction mixture was diluted with ether washed with water (100 mL). The aqueous layer was washed with ether and the organic layers combined, washed with brine, dried (MgSO4), and concentrated. Purification by flash chromatography (SiO2, eluted with 3% ethylacetate/hexanes) afforded 3-bromothiophene-2-carboxaldehyde (5.6 g, 71%) as a slightly yellow liquid that solidified upon refrigeration.

The aldehyde (1.0 g, 4.5 mMol) obtained above was dissolved in 1:1 pyridine, ethanol (15 mL). To this stirred solution was added hydroxylamine hydrochloride (0.63 g, 9.3 mMol). The reaction was allowed to stir overnight at room temperature and then concentrated. The residue was partitioned between ether (100 mL) and cold 10% HCl (50 mL). The organic layer was washed with brine and dried (MgSO4). Concentration afforded the oxime intermediate (1.1 g) as a yellow liquid that was used without further purification.

The oxime (1.1 g, 5.4 mMol) obtained above was dissolved in ethanol (25 mL) and borane pyridine (1.26 g, 13.5 mMol) was added via syringe. The reaction flask was equipped with a dropping funnel and charged with 6N HCl (14 mL). The HCl solution was added at a rate to maintain a gentle reflux. The solution was allowed to stir 1 h at room temperature and concentrated. The resulting reside was neutralized with 3N NaOH, and extracted with ethylacetate (3×50 mL). The combined organics were washed with water (50 mL) and dried (MgSO$_4$). Concentration afforded the hydroxylamine intermediate (1.1 g) as a white solid and it was used without further purification.

To a stirred THF (15 mL) solution of the hydroxylamine (1.1 g, 5.3 mMol) obtained above was added trimethylsilylisocyanate (0.98 g, 8.5 mMol). The solution was stirred 1 h at room temperature and poured into sat'd NH$_4$Cl/ice. The THF was removed and the resulting aqueous residue thoroughly extracted with ethylacetate. The combined organic layer was dried (MgSO$_4$) and concentrated to give a white solid. Recrystalization from ethylacetate/hexanes afforded the title compound (0.8 g, 71% from aldehyde) as a white solid. mp: 138°–139.5° C.; NMR (300 MHz, DMSO-d$_6$) δ 4.65 (2H, s), 6.43 (2H, bs), 7.03 (1H, d, J=1 Hz), 7.57 (1H, d, J=1 Hz), 9.50 (1H, s); MS m/e (DCI/NH$_3$) 268 (M+NH$_4$)$^+$, 251 (M+H)$^+$.

Anal. Calcd for C$_6$H$_7$BrN$_2$O$_2$S: C, 28.70; H, 2.81; N, 11.16. Found: C, 28.62; H, 2.81; N, 11.12.

EXAMPLE 128

Preparation of
N-hydroxy-N-(4-bromothien-2-yl)methyl urea

The title compound was prepared according to the method of Example 127 using 4-bromothiophene-2-carboxaldehyde instead of 3-bromothiophene-2-carboxaldehyde. mp: 162°–163.5° C.; NMR (300 MHz, DMSO-d$_6$) δ 4.61 (2H, s), 6.47 (2H, bs), 6.98 (1H, d, J=1 Hz), 7.54 (1H, d, J=1 Hz), 9.52 (1H, s); MS m/e (fab) 251 (M+H)$^+$.

Anal. Calcd for C$_6$H$_7$BrN$_2$O$_2$S: C, 28.70; H, 2.81; N, 11.16. Found: C, 28.95; H, 2.81; N, 11.20.

EXAMPLE 129

Preparation of
N-hydroxy-N-(5-chlorothien-2-yl)methyl urea

The title compound was prepared according to the method of Example 127 using 5-chlorothiophene-2-carboxaldehyde instead of 3-bromothiophene-2-carboxaldehyde. mp: 138.5°–140° C.; NMR (300 MHz, DMSO-d$_6$) δ 4.55 (2H, s), 6.46 (2H, bs), 6.85 (1H, d, J=3.5 Hz), 6.95 (1H, d, J=3.5 Hz), 9.51 (1H, s); MS m/e (DCI/isobutane) 207 (M+H)$^+$.

Anal. Calcd for C$_6$H$_7$ClN$_2$O$_2$S: C, 34.87; H, 3.41; N, 13.56. Found: C, 34.96; H, 3.46; N, 13.44.

EXAMPLE 130

Preparation of
N-hydroxy-N-(5-bromothien-2-yl)methyl urea

The title compound was prepared according to the method of Example 127 using 5-bromothiophene-2-carboxaldehyde instead of 3-bromothiophene-2-carboxaldehyde. mp: 145°–147° C.; NMR (300 MHz, DMSO-d$_6$) δ 4.57 (2H, s), 6.47 (2H, bs), 6.83 (1H, d, J=4 Hz), 7.05 (1H, d, J=4 Hz), 9.52 (1H, s); MS m/e (DCI/NH$_3$) 268 (M+NH$_4$)$^+$, 251 (M+H)$^+$.

EXAMPLE 131

Preparation of
N-hydroxy-N-(5-bromothien-2-yl)methyl-N'-methylurea

The title compound is prepared from (5-bromothien-2-yl)methyl hydroxylamine from Example 127 by reaction with methyl isocyanate instead of trimethylsilylisocyanate.

EXAMPLE 132

Preparation of
N-hydroxy-N-[1-(4-bromothien-2-yl)ethyl]urea

The title compound was prepared according to the method of Example 127 using 4-bromo-2-acetylthiophene instead of 3-bromothiophene-2-carbox-aldehyde. mp: 154°–157° C. (dec); NMR (300 MHz, DMSO-d$_6$) δ 1.42 (3H, d, J=7 Hz), 5.46 (1H, q, J=7 Hz), 6.47 (2H, bs), 6.94 (1H, m), 7.52 (1H, d, J=1 Hz), 9.25 (1H, s); MS m/e (DCI-NH3) 282 (M+NH$_4$)$^+$, 265 (M+H)$^+$.

Anal. Calcd for C$_7$H$_9$BrN$_2$O$_2$S: C, 31.71; H, 3.42; N, 10.57 Found: C, 31.41; H, 3.35; N, 10.40.

EXAMPLE 133

Preparation of
N-hydroxy-N-[1-(5-bromothien-2-yl)ethyl]urea

The title compound was prepared according to the method of Example 127 using 5-bromo-2-acetylthiophene instead of 3-bromothiophene-2-carboxaldehyde. mp: 147°–149° C. (dec); NMR (300 MHz, DMSO-d$_6$) δ 1.39 (3H, d, J=4 Hz), 5.42 (1H, q, J=7 Hz), 6.46 (2H, bs), 6.78 (1H, m), 7.03 (1H, d, J=3 Hz), 9.26 (1H, s); MS m/e (DCI-NH3) 282 (M+NH$_4$)$^+$.

EXAMPLE 134

Preparation of
N-hydroxy-N-[3-(phenylthio)thien-2-yl]methyl urea

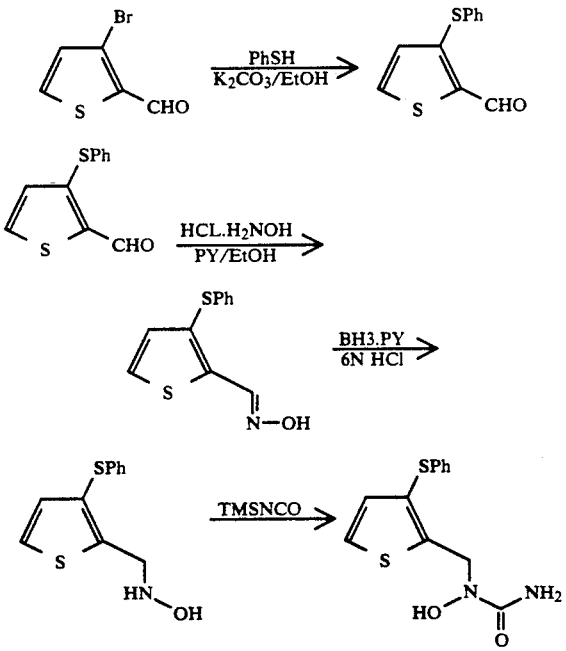

a) Preparation of 3-(phenylthio)thiophene-2-carboxaldehyde

To a stirred solution of 3-bromothiophene-2-carboxaldehyde (1.9 g, 10 mMol) in ethanol (15 mL) is added thiophenol (2.2 g, 20 mMol) and powdered potassium carbonate (3.04 g, 22 mMol). The mixture is stirred overnight and concentrated. The residue is partitioned between water and ether. The aqueous layer is washed with ether and the organics combined, dried(MgSO$_4$)

and concentrated. Purification by flash column (SiO$_2$, eluted with 3% ethylacetate/hexanes) afforded the desired aldehyde (2.02 g, 92%) as a yellow liquid.

The title compound was prepared according to the method of Example 127 using 3-(phenylthio)thiophene-2-carboxaldehyde (prepared above) instead of 3-bromothiophene-2-carboxaldehyde. mp: 99°–100.5° C. NMR (300 MHz, DMSO-d$_6$) δ 4.77 (2H, s), 6.47 (2H, bs), 6.95 (1H, d, J=6 Hz), 7.10–7.21 (3H, m), 7.24–7.33 (2H, m), 7.59 (1H, d, J=6 Hz), 9.51 (1H, s); MS m/e (DCI/NH$_3$) 298 (M+NH$_4$)$^+$, 281 (M+H)$^+$.

EXAMPLE 135

Preparation of N-hydroxy-N-[5-(phenylthio)thien-2-yl]methyl urea 5-(Phenylthio)thiophene-2-carboxaldehyde was prepared as described in Example 134 using 5-bromothiophene-2-carboxaldehyde instead of 3-bromothiophene-2-carboxaldehyde.

The title compound was prepared according to the method of Example 127 using 5-(phenylthio)thiophene-2-carboxaldehyde instead of 3-bromothio-phene-2-carboxaldehyde. mp: 126°–128° C. (dec); NMR (300 MHz, DMSO-d$_6$) δ 4.63 (2H, s), 6.47 (2H, bs), 7.02 (1H, d, J=4 Hz), 7.27–7.37 (6H, m), 9.53 (1H, s); MS m/e (DCI/NH$_3$) 298 (M+NH$_4$)$^+$, 281 (M+H)$^+$.

EXAMPLE 136

Preparation of N-hydroxy-N-[4-(phenylthio)thien-2-yl]methyl urea

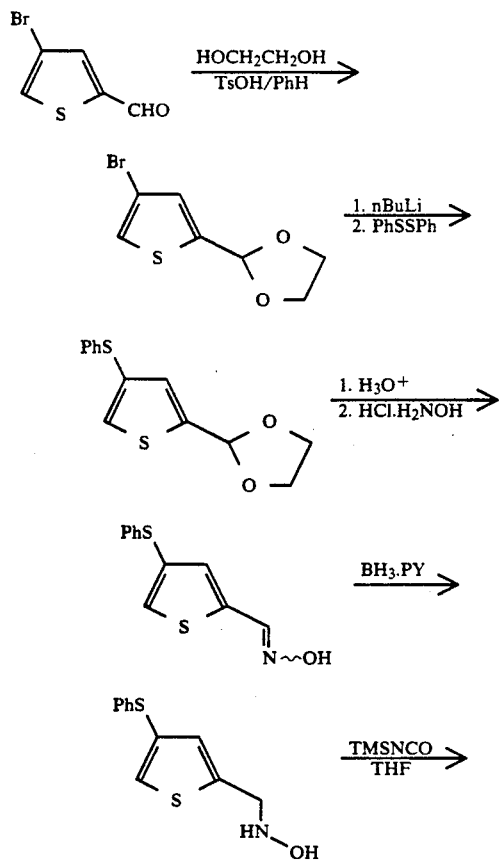

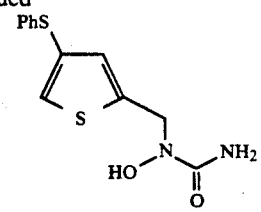

Preparation of 4-(phenylthio)thiophene-2-carboxaldehyde a) 2-(4-bromo-2-thienyl)-1,3-dioxolane In a 100 mL roundbottom flask equipped with a dean stark trap and a reflux condenser, 4-bromothiophene-2-carboxaldehyde (25 g, 131 mMol) and a catalytic amount of p-toluenesulfonic acid were dissolved in benzene (50 mL). The mixture was heated to reflux overnight. The reaction was cooled, washed with sat'd sodium bicarbonate, water, dried (MgSO$_4$) and concentrated. Purification by fractional distillation (80°–90° C., 0.5 mm Hg) afforded 24.23 g (72%) of the desired dioxolane as a clear liquid.

b) 2-[(4-phenylthio)thien-2-yl]-1,3-dioxolane

To a cold (−78° C., dry ice/acetone) stirred solution of the bromothienyl dioxolane (8 g, 34 mMol) prepared above in ether (150 mL) was added n-butyl lithium (15 mL, 37.4 mMol, 2.5M in hexanes). The reaction was stirred for 10 min and diphenyldisulfide (8.2 g, 37.4 mMol) added as a solid. The ice bath was removed and the reaction allowed to warm to room temperature. Water was added and the layers separated. The organic layer was dried (MgSO$_4$) and concentrated. Purification by flash column chromatography (SiO2, eluted with 10% ethylacetate/hexanes) afforded 6.05 g (67%) of the desired dioxolane as an oil.

c) 4-(phenylthio)thiophene-2-carboxaldehyde

To a stirred solution of the phenylthiosubstituted thienyl-dioxolane (6.05 g, 23 mMol) prepared above in dioxane (45 mL) was added 10% HCl (45 mL). The reaction was stirred 20 min at room temperature and the dioxane removed removed by rotory evaporator. The resulting residue was extracted thoroughly with ethyl acetate. The combined organic layer washed with sat'd NaHCO$_3$, water, dried (MgSO4). Concentration afforded 5.06 g of the desired aldehyde as a clear oil.

The title compound was prepared according to the method of Example 127 using 4-(phenylthio)thiophene-2-carboxaldehyde (prepared above) instead of 3-bromothiophene-2-carboxaldehyde. mp: 111°–113° C. (dec); NMR (300 MHz, DMSO-d$_6$) δ 4.62 (2H, s), 6.46 (2H, bs), 6.94 (1H, d, J=1 Hz), 7.16–7.25 (3H, m), 7.28–7.36 (2H, m), 7.63 (1H, d, J=1 Hz), 9.50 (1H, s); MS m/e (DCI/NH$_3$) 298 (M+NH$_4$)$^+$, 281 (M+H)$^+$.

EXAMPLE 137

Preparation of N-hydroxy-N-[5-(phenylthio)thien-3-yl]methyl urea

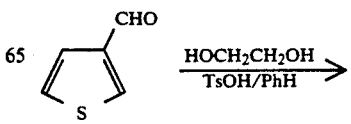

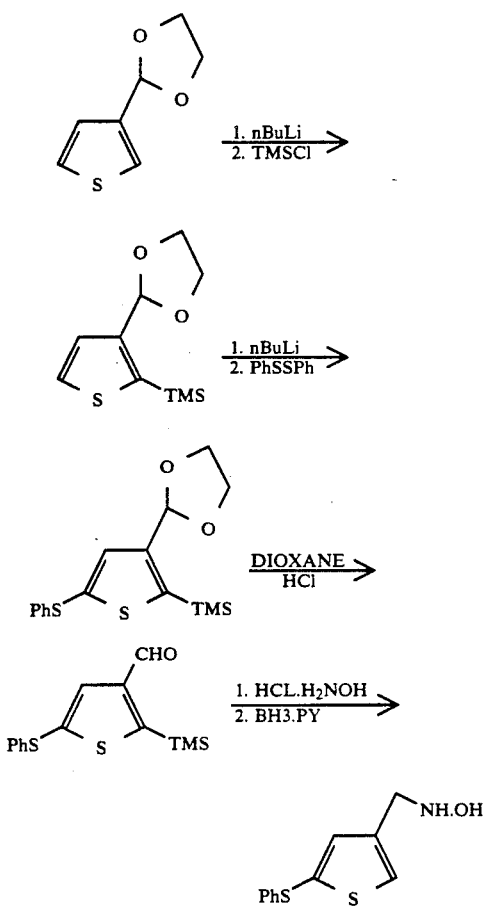

a) 2-(3-thienyl)-1,3-dioxolane

In a 100 mL roundbottom flask equipped with a dean stark trap and a reflux condenser, thiophene-3-carboxaldehyde and p-toluenesulfonic acid were dissolved in benzene (50 mL). The mixture was heated to reflux overnight. The reaction was cooled, washed with sat'd sodium bicarbonate, water, dried (MgSO4) and concentrated. Purification by fractional distillation (93°-95° C., 7.5 mm Hg) afforded 45.3 g (72%) of the desired dioxolane as a clear liquid.

b) 2-[(2-trimethylsilyl)thien-3-yl]-1,3-dioxolane

To a 0° C. stirred solution of the 3-thienyl dioxolane (5 g, 32.1 mMol) prepared above in ether (100 mL) was added n-butyl lithium (14.1 mL, 35.2 mMol, 2.5M in hexanes). The reaction was stirred for 10 min and trimethylsilyl chloride (3.83 g, 35.3 mMol) added via syringe. The ice bath was removed and the reaction allowed to warm to room temperature. Sat'd ammonium chloride was added and the layers separated. The organic layer was dried (MgSO4) and concentrated. Purification by flash column chromotography (SiO2, eluted with 5% ethylacetate/hexanes) afforded 4.0 g (55%) of the desired dioxolane as an oil.

c) 2-[(5-phenylthio-2-trimethylsilyl)thien-3-yl]-1,3-dioxolane

To a 0° C. stirred solution of the 2-trimethylsilylthien-3-yl dioxolane (4 g, 17.5 mMol) prepared above in ether (100 mL) was added n-butyl lithium (7.7 mL, 19.3 mMol, 2.5M in hexanes). The reaction was stirred for 15 min and diphenyl disulfide (4.2 g, 19.3 mMol) added as a solid. The ice bath was removed and the reaction allowed to warm to room temperature. Water was added and the layers separated. The organic layer was dried (MgSO4) and concentrated. This crude dioxolane was used without further purification.

d) 5-phenylthio-2-trimethylsilylthiophene-3-carboxaldehyde

To a stirred solution of the crude phenythiosubstituted thienyl-dioxolane (3.8 g, prepared above in dioxane (20 mL) was added 10% HCl (20 mL). The reaction was stirred 20 min at room temperature and the dioxane removed by rotory evaporator. The resulting residue was extracted thoroughly with ethyl acetate. The combined organic layer washed with sat'd NaHCO3, water, dried (MgSO4).and concentrated. Purification by flash column chromotography (SiO2, eluted with 5% ethylacetate/hexanes) afforded 1.16 g of the pure aldehyde as an oil.

e) [(5-phenylthio)thien-3-yl]methyl hydroxylamine

The aldehyde (1.0 g, 3.7 mMol) obtained above was dissolved in 1:1 pyridine, ethanol (10 mL). To this stirred solution was added hydroxylamine hydrochloride (1 g, 14 mMol). The reaction was allowed to stir overnight at room temperature and then concentrated. The residue was partitioned between ether (100 mL) and cold 10% HCl (50 mL). The organic layer was washed with brine and dried (MgSO4). Concentration afforded the oxime intermediate (1.1 g) as a yellow liquid that was used without further purification.

The oxime obtained above was dissolved in ethanol (25 mL) and borane pyridine (1.26 g, 13.5 mMol) was added via syringe. The reaction flask was equipped with a dropping funnel and charged with 6N HCl (14 mL). The HCl solution was added at a rate to maintain a gentle reflux. The solution was allowed to stir 1 h at room temperature and concentrated. The resulting reside was neutralized with 3N NaOH, and extracted with ethylacetate (3×50 mL). The combined organics were washed with water (50 mL) and dried (MgSO4). Concentration afforded the desilylated hydroxylamine intermediate.

The title compound was prepared from the hydroxylamine described above by standard treatment with trimethylsilyl isocyanate. mp: 113°-114° C.; NMR (300 MHz, DMSO-d6) δ 4.47 (2H, s), 6.44 (2H, bs), 7.17-7.26 (3H, m), 7.28-7.38 (3H, m), 7.56 (1H, d, J=1 Hz), 9.45 (1H, s); MS m/e (DCI/NH3) 298 (M+NH4)+, 281 (M+H)+;

Anal. Calcd for C12H12N2O2S2: C, 51.41; H, 4.31; N, 9.99. Found: C, 51.16; H, 4.27; N, 9.91.

EXAMPLE 138

Preparation of N-hydroxy-N-[2-(phenylthio)thien-3-yl]methyl urea

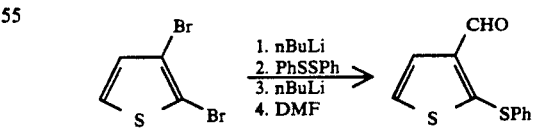

Preparation of (2-phenylthio)thiophene-3-carboxaldehyde

To a 0° C. solution of 2,3-dibromothiophene (5 g, 20 mMol) in ether (25 mL) was added n-butyllithium (8 mL, 20 mMol, 2.5M in hexanes). The reaction was stirred for 20 min and diphenyl disulfide (4.36 g, 20 mMol) was added as a solid. The reaction was stirred 0.5 h and then cooled to −78° C. n-Butyl lithium (8 mL, 20 mMol, 2.5M in hexanes) was added and the reaction stirred an additional 15 min. To the cold reaction mixture was added DMF (5 mL) and the reaction allowed to warm to room temperature. Water (5 mL) was added cautiously while stirring. The reaction mixture was diluted with ether and washed with water (100 mL). The aqueous layer was washed with ether and the organic layers combined, washed with brine, dried (MgSO$_4$), and concentrated. Purification by flash chromatography (SiO2, eluted with 10% ethylacetate/hexanes) afforded (2-phenylthio)thiophene-3-carboxaldehyde (2.8 g, 63%) as a slightly yellow oil.

The title compound was prepared according to the method of Example 127 using (2-phenylthio)thiophene-3-carboxaldehyde (prepared above) instead of 3-bromothiophene-2-carboxaldehyde. mp: 120°-122° C.; NMR (300 MHz, DMSO-d$_6$) δ 4.56 (2H, s), 6.43(2H, bs), 7.12-7.23 (4H, m), 7.26-7.34 (2H, m), 7.76 (1H, d, J=4 Hz), 9.43 (1H, s); MS m/e (DCI/NH$_3$) 298 (M+NH$_4$)$^+$, 281 (M+H)$^+$.

EXAMPLE 139

Preparation of
N-hydroxy-N-[1-(5-(phenylthio)-thien-2-yl)ethyl]urea 5-(Phenylthio)-2-acetylthiophene was prepared as described in Example 136 using 5-bromo-2-acetylthiophenethiophene (prepared in Example 131) instead of 3-bromothiophene-2-carboxaldehyde The title compound was prepared according to the method of Example 127 using 5-(phenylthio)-2-acetylthiophene instead of 3-bromothiophene-2-carboxaldehyde. mp: 151° C. (dec); NMR (300 MHz, DMSO-d$_6$) δ 1.43 (3H, d, J=7 Hz), 5.48 (1H, q, J=7 Hz), 6.46 (2H, bs), 6.98 (1H, m), 7.16-7.26 (4H, m), 7.34 (2H, m), 9.26 (1H, s); MS m/e (DCI-NH3) 312 (M+NH$_4$)$^+$, 219.

EXAMPLE 140

Preparation of
N-hydroxy-N-[3-(4-hydroxyphenylthio)thien-2-yl]methyl urea

The title compound was prepared according to the method of Example 134 using 4-hydroxythiophenol instead of thiophenol. mp: 145° C. (dec); NMR (300 MHz, DMSO-d$_6$) δ 4.78 (2H, s), 6.45 (2H, bs), 6.71 (2H, m), 6.81 (1H, d, J=6 Hz), 7.25 (2H, m), 7.46 (1H, d, J=6 Hz), 9.50 (1H, s), 9.61 (1H, s); MS m/e (DCI/NH$_3$) 314 (M+NH$_4$)$^+$, 297 (M+H)$^+$.

EXAMPLE 141

Preparation of
N-hydroxy-N-[3-(4-bromophenylthio)thien-2-yl]methyl urea

The title compound was prepared according to the method of Example 134 using 4-bromothiophenol instead of thiophenol. mp: 124°-126° C. NMR (300 MHz, DMSO-d$_6$) δ 4.76 (2H, s), 6.48 (2H, bs), 6.98(1H, d, J=6 Hz), 7.05 (2H, m), 7.47 (2H, m), 7.62 (1H, d, J=6 Hz), 9.52 (1H, s); MS m/e (DCI/NH$_3$) 376 (M+NH$_4$)$^+$, 359 (M+H)$^+$.

EXAMPLE 142

Preparation of
N-hydroxy-N-[3-(4-chlorophenylthio)thien-2-yl]methyl urea

The title compound was prepared according to the method of Example 134 using 4-chlorothiophenol instead of thiophenol. mp: 111°-113° C. NMR (300 MHz, DMSO-d$_6$) δ 4.75 (2H, s), 6.48 (2H, bs), 6.97(1H, d, J=6 Hz), 7.12 (2H, m), 7.34 (2H, m), 7.62 (1H, d, J=6 Hz), 9.52 (1H, s); MS m/e (DCI/NH$_3$) 332 (M+NH$_4$)$^+$, 315 (M+H)$^+$.

EXAMPLE 143

Preparation of
N-hydroxy-N-[3-(4-fluorophenylthio)thien-2-yl]methyl urea

The title compound was prepared according to the method of Example 134 using 4-fluorothiophenol instead of thiophenol. mp: 101°-103° C. NMR (300 MHz, DMOS-d$_6$) δ 4.78 (2H, s), 6.48 (2H, bs), 6.94 (1H, d, J=6 Hz), 7.10-7.26(4H, m), 7.58 (1H, d, J=6 Hz), 9.53 (1H, s); MS m/e (DCI/NH$_3$) 316 (M+NH$_4$)$^+$, 299 (M+H)$^+$.

EXAMPLE 144

Preparation of
N-hydroxy-N-[3-(4-tertbutylphenylthio)thien-2-yl]methyl urea

The title compound was prepared according to the method of Example 134 using 4-tertbutylthiophenol instead of thiophenol. mp: 144°-146° C.; NMR (300 MHz, DMSO-d$_6$) δ 1.24 (9H, s), 4.78 (2H, s), 6.48 (2H, bs), 6.93 (1H, d, J=6 Hz), 7.08 (2H, m), 7.31 (2H, m), 7.56 (1H, d, J=6 Hz), 9.52 (1H, s); MS m/e (FAB) 337 (M+H)$^+$.

EXAMPLE 145

Preparation of
N-hydroxy-N-[3-(2-pyridylthio)thien-2-yl]methyl urea

The title compound was prepared according to the method of Example 134 using 2-mercaptopyridine instead of thiophenol. mp: 80° C. (dec); NMR (300 MHz, DMSO-d$_6$) δ 4.75 (2H, s), 6.46 (2h, bs), 6.81 (1H, d, J=8 Hz), 7.08 (1H, d, J=6 Hz) 7.13 (1H, m), 7.60 (1H, m), 7.65 (1H, d, J=6 Hz), 8.38 (1H, m), 9.49 (1H, s); MS m/e (DCl/NH$_3$) 282 (M+H)$^+$, 266.

EXAMPLE 146

Preparation of
N-hydroxy-N-[3-(2-furfurylmethylthio)thien-2-yl]methyl urea

The title compound was prepared according to the method of Example 134 using furfurylmercaptan instead of thiophenol. mp: 93°-92° C.; NMR (300MHz, DMSO-d$_6$) δ 4.20 (2H,s), 4.62 (2H,s), 6.05 (1H,m), 6.34 (1H, m), 6.43 (2H,bs), 6.94(1H,d,J=6 Hz), 7.46 (1H ,d ,J=6Hz), 7.57 (1H,m), 9.45 (1H,s); MS m/e (DCI/NH$_3$) 302 (M+NH$_4$)$^+$, 285 (M+H)$^+$, 209.

EXAMPLE 147

Preparation of
N-hydroxy-N-[3-(tertbutylthio)thien-2-yl]methyl urea

The title compound was prepared according to the method of Example 134 using 4-tertbutythiophenol instead of thiophenol mp: 145°-146° C.; NMR (500 MHz, DMSO-d$_6$) δ 1.23(9H, s), 4.83 (2H, s), 6.39 (2H, bs), 6.99 (1H,d, J=5 Hz), 7.48 (1H,d, J=5 Hz), 9.42 (1H, s); MS m/e (DCI/NH$_3$) 278 (M +NH$_4$)$^+$, 261 (M+H)$^+$.

EXAMPLE 148

Preparation of
N-hydroxy-N-[5-(tertbutylthio)thien-2-yl]methyl urea

The title compound was prepared according to the method of Example 135 using tertbutylmercaptan instead of thiophenol. mp: 101°-103° C. NMR (500 MHz, DMSO-d6) δ 1.26 (9H, s), 4.61 (2H, s), 6.45 (2H, bs), 6.96 (1H,d, J=3 HZ), 7.03 (1H,d, J=3Hz), 9.49 (1H, s); MS m/e (DCI/NH3) 278 (M+NH4)+, 261 (M+H)+, 185.

EXAMPLE 149

Preparation of
N-hydroxy-N-[1-(5-{terbutylthio}thien-2-yl)ethyl]urea

The title compound was prepared according to the method of Example 148 using 5-bromo-2-acetylthiophene instead of 5-bromothiophene-2-carboxaldehyde. mp: 135°-136° C.; NMR (300 MHz, DMSO-d6) δ 1.25 (9H, s), 1.42 (3H, d, J=7 Hz), 5.46 (1H, q, J=7 Hz)), 6.44 (2H, bs), 6.92 (1H, m), 7.01 (1H, d, J=3 Hz), 9.22 (1H, s); MS m/e (DCI-NH3) 292 (M+NH4)+, 274 (M+H)+, 199.

EXAMPLE 150

Preparation of
N-hydroxy-N-[5-(isopropylthio)thien-2-yl]methyl urea

The title compound was prepared according to the method of Example 135 using isopropylmercaptan instead of thiophenol as an off white powder. This material contained approximately 10% of the 5-bromocompound (Example 131): NMR (500 MHz, DMSO-d6) δ 1.21 (6H, d, J=7 Hz), 3.13 (1H, hept, J=7 Hz), 4.59 (2H, s), 6.44 (2H, bs), 6.92 (1H, d, J=4 Hz), 7.02 (1H, d, J=4 Hz), 9.48 (1H, s); MS m/e (DCI/NH3) 264 (M+NH4)+, 247 (M+H)+.

EXAMPLE 151

Preparation of
N-hydroxy-N-[1-(5-{methylthio}thien-2-yl)ethyl]urea

The title compound was prepared according to the method of Example 127 using 5-methylthio-2-acetylthiophene instead of 3-bromothiophene-2-carboxaldehyde. mp: 125.5°-126.5° C. (dec); NMR (300 MHz, DMSO-d6) δ 1.40 (3H, d, J=7 Hz), 2.45 (3H, S), 5.42 (1H, q, J=7 Hz), 6.40 (2H, bs), 6.83 (1H, d, J=3 Hz), 6.94 (1H, d, J=3 Hz), 9.28 (1H, s); MS m/e (DCI-NH3) 250 (M+NH4)+, 233 (M+H)+.

EXAMPLE 152

Preparation of
N-hydroxy-N-3-[5-(phenylthio)thien-2-yl]propenyl urea

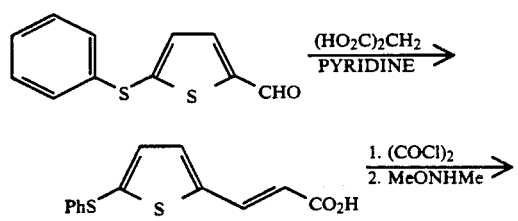

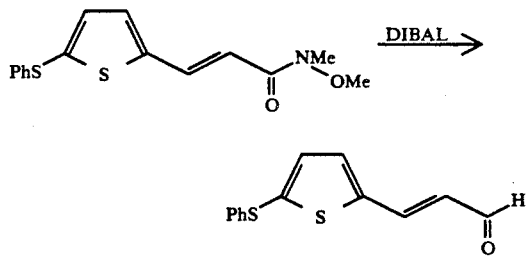

Preparation of 3-[5-(phenylthio)thien-2-yl] acrolein a) 3-[5-(phenylthio)thien-2-yl] acrylic acid. To a stirred solution of (5-thiophenyl)thiophene-2-carboxaldehyde (11.6 g, 60.4 mMol) (from Example 135) in pyridine (75 mL) was added malonic acid (12.6 g, 120 mMol) and morpholine (0.5 mL). The mixture was heated to reflux and stirred overnight. The mixture was cooled and poured into 10% HCl/ice. The tan solid was collected, washed and dried to give 11.36 g of the desired acid that was used without further purification.

b) N,O,dimethyl-3-[5-(phenythio)thien-2-yl] acrylamide. The acid (11.36 g, 43.36 mMol) obtained above was dissolved in dry methylene chloride (100 mL). To this stirred solution was added oxalyl chloride (7.96 g, 65 mMol) and DMF (~1 mL). The mixture was stirred for 3 h and concentrated to dryness. The residue was dissolved in fresh dry methylene chloride (100 mL) and to this stirred solution was added pyridine (11 g, 131 mMol) and N,O-dimethylhydroxylamine hydrochloride (6.3 g, 65 mMol). The reaction was stirred for 2 h and concentrated. The resulting reside was partitioned between water and ethylacetate. The aqueous layer was washed with ethylacetate and the organic layers combined, dried (MgSO4) and concentrated. The residue was purified by flash column chromotography (SiO2, eluted with 2:1 hexanes/ethylacetate) to afford 10.5 g (79%) of the unsaturated amide as an off white solid.

c) 3-[(5-phenylthio)thien-2-yl] acrolein

The unsaturated amide obtained above was treated with 1.5 equivalents of DIBAL in methylene chloride at −78° C. The reaction was poured into 10% HCl and extractive work up gave crude aldehyde that was used without further purification The crude aldehyde obtained in this manner was converted to the title compound by the method described for Example 1 to afford a white crystaline solid. mp: 152°-154° C.; NMR (300 MHz, DMSO-d6) δ 4.05 (2H, m), 6.02 (1H, m), 6.48 (2H, bs), 6.71 (1H, d, J=16 Hz), 7.09 (1H, d, J=4 Hz), 7.19-7.26 (3H, m), 7.28-7.38 (3H, m), 9.36 (1H, s); MS m/e (DCI/NH3) 324 (M+NH4)+, 307 (M+H)+.

Anal. Calcd for C14H14N2O2S2: C, 54.88; H, 4.61; N, 9.14. Found: C, 54.04; H, 4.65; N, 9.04.

EXAMPLE 153

Preparation of
N-hydroxy-N-(3-[5-(phenylthio)thien-2-yl]butenyl urea

Methylmagnesium bromide was added to an ether solution of the N,O,dimethyl-3-[5-(phenylthio)thien-2-yl] acrylamide intermediate from Example 152. The crude ketone obtained after aqueous work up was converted to the title compound by the method described for Example 1, to afford an off white powder that contains approximately 10% of the saturated N-hydroxy-N-3-[5-(phenylthio)thien-2-yl]butyl urea.

NMR (300 MHz, DMSO-d$_6$) δ 1.19 (3H, d, J=7 Hz), 4.78 (1H, m), 6.06 (1H, dd, J=16 Hz, J=7 Hz), 6.48 (2H, bs), 6.65 (1H, m), 7.08 (1H, d, J=16 Hz), 7.15-7.48 (6H, m), 9.07 (1H, s); MS m/e (DCI/NH$_3$) 338 (M+NH$_4$)+, 321 (M+H)+, 245; Anal. Calcd for C$_{15}$H$_{16}$N$_2$O$_2$S$_2$: C, 56.23; H, 5.03; N, 8.74. Found: C, 55.65; H, 5.15; N, 8.64.

EXAMPLE 154

Preparation of N-hydroxy-N-3-[5-(tertbutylthio)thien-2-yl]propenyl urea

The desired product was prepared according to the method of Example 152 using 5-tertbutylthiophene-2-carboxaldehyde instead of 5-(thiophenyl)thiophene-2-carboxaldehyde. mp: 111°-113° C. NMR (300 MHz, DMSO-d$_6$) δ 1.27 (9H, s), 4.05 (2H, m), 6.03 (1H, m), 6.38 (2H, bs), 6.67 (1H, d, J=15 Hz), 7.04 (1H, d, J=4 Hz), 7.08 (1H, d, J=4 Hz), 9.35 (1H, s); MS m/e (DCI/NH$_3$) 304 (M+NH$_4$)+, 287 (M+H)+.

EXAMPLE 155

Preparation of N-hydroxy-N-[5-(phenoxy)thien-2-yl]methyl urea

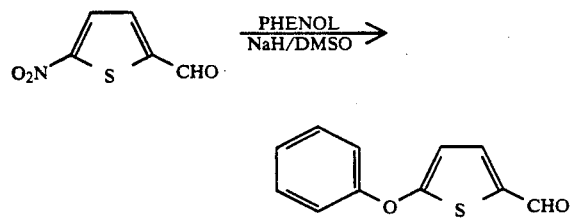

a) 5-phenoxythiophene-2-carboxaldehyde.

To a stirred suspension of sodium hydride (1.05 g, 35 mMol, 80% oil dispersion) in DMSO (100 mL) is added phenol (3.3 g, 35 mMol). The mixture was stirred 0.5 h at room temperature and a DMSO (30 mL) solution of 5-nitrothiophene-2-carboxaldehyde (5 g, 32 mMol) was added dropwise. The reaction was stirred 0.5 h and poured into water. The mixture was thoroughly extracted with ether and the combined organics rewashed with brine. The organics were then dried (MgSO$_4$) and concentrated to give crude aldehyde.

The crude aldehyde prepared in this manner was converted to the title compound according to the method of Example 127. mp: 114°-116° C.; NMR (300 MHz, DMSO d$_6$) δ 4.53 (2H, s), 6.42 (2H, bs), 6.50 (1H, d, J=4 Hz), 6.74 (1H, d, J=4 Hz), 7.13 (3H, m), 7.40 (2H, m), 9.45 (1H, s); MS m/e (DCI/NH$_3$) 282 (M+NH$_4$)+, 265 (M+H)+, 189.

EXAMPLE 156

Preparation of N-hydroxy-N-[3-(phenoxy)thien-2-yl]methyl urea

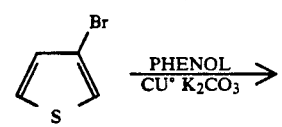

-continued

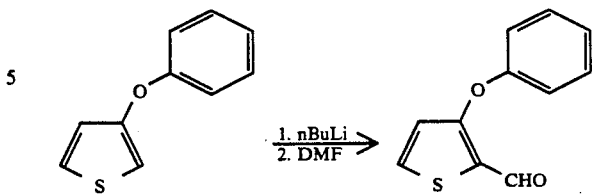

Preparation of 3-phenoxythiophene-2-carboxaldehyde a) 3-phenoxythiophene.

A mixture of 3-bromothiophene (100 g, 610 mMol), phenol (61.2 g, 650 mMol), copper bronze (5 g) and potassium carbonate (30 g, 220 mMol) was heated to 150° C. After heating for 7 days the mixture was cooled, diluted with 300 mL of chloroform and filtered. The solids were thoroughly washed with chloroform and the filtrates combined. The combined organics were washed with 10% NaOH (2×300 mL), water (300 mL), dried (MgSO4) and concentrated. The residue was factionally distilled to afford 31 g (29%) (80° C., 3 mm) of the desired ether as a clear liquid.

b) 3-phenoxythiophene-2-carboxaldehyde.

To a 0° C. solution of 3-phenoxythiophene (2 g, 11.4 mMol) in ether (50 mL) was added n-butyllithium (5 mL, 12.5 mMol, 2.5M in hexanes). The reaction was stirred for 15 min and N,N-dimethylformamide (3 mL) was added. The reaction was allowed to warm to room temperature. Water (5 mL) was added cautiously while stirring. The reaction mixture was diluted with ether and washed with water (100 mL). The aqueous layer was washed with ether and the organic layer combined, washed with brine, dried (MgSO$_4$), and concentrated. The residue was purified by flash column chromotography (SiO$_2$, eluted with 10% ethylacetate/hexanes) to afford 1.74 g (75%) of the desired aldehyde as a clear oil.

The title compound was prepared according to the method of Example 127 using 3-phenoxythiophene-2-carboxaldehyde (prepared above) instead of 3-bromothiophene-2-carboxaldehyde. mp: 132°-133.5° C.; NMR (300 MHz, DMSO-d$_6$) δ 4.55 (2H, s), 6.43 (2H, bs), 6.72 (1H, d, J=6 Hz), 6.95 (2H, m), 7.06 (1H, m), 7.33 (2H, m), 7.46 (1H, d, J=6 Hz), 9.44 (1H, s); MS m/e (DCI/NH$_3$) 282 (M+NH$_4$)+, 265 (M+H)+.

Anal. Calcd for C$_{12}$H$_{12}$N$_2$O$_3$S: C, 54.53; H, 4.58; N, 10.60 Found: C, 53.73; H, 4.39; N, 10.43.

EXAMPLE 157

Preparation of N-hydroxy-N-[4-(phenoxy)thien-2-yl]methyl urea

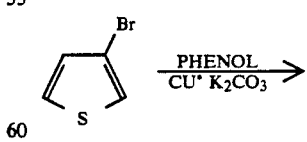

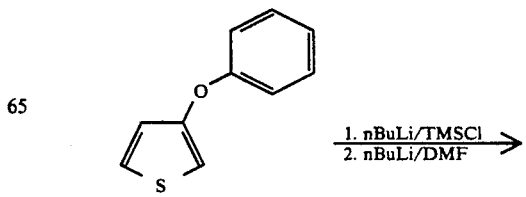

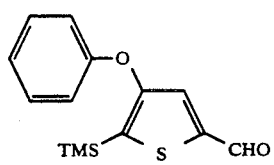

a) 4-phenoxy-5-trimethylsilylthiophene-2-carboxaldehyde

To a 0° C. solution of 3-phenoxythiophene (9.5 g, 53.9 mMol) in ether (200 mL) was added n-butyllithium (24 mL, 60 mMol, 2.5M in hexanes). The reaction was stirred for 15 min and trimethylsilyl chloride (6.45 g, 59.4 mMol) was added via syringe. The reaction was stirred 15 min and additional n-butyllithium (24 mL, 60 mMol, 2.5M in hexanes) was added and the reaction stirred 15 min. To the cold reaction mixture is added DMF (14 mL) and the reaction allowed to warm to room temperature over night. Water (5 mL) was added cautiously while stirring. The reaction mixture was diluted with ether and washed with water. The aqueous layer was washed with ether and the organic layer combined, washed with brine, dried (MgSO$_4$), and concentrated. Purification by flash chromatography (SiO2, eluted with 5% ether/hexanes) afforded 4-phenoxy-5-trimethylsilylthiophene-2-carboxaldehyde (12.1 g, 83%) as a slightly yellow oil.

The title compound was prepared as described in Example 137 except using 4-phenoxy-5-trimethylsilylthiophene-2-carboxaldehyde described above instead of 5-phenylthio-2-trimethylsilylthiophene-3-carboxaldehyde. mp: 120°-122° C.; NMR (300 MHz, DMSO d$_6$) δ 4.57 (2H, s), 6.46 (2H, bs), 6.78 (2H, s), 7.03 (2H, m), 7.12 (1H, m), 7.38 (2H, m), 9.49 (1H, s); MS m/e (DCI/NH$_3$) 282 (M+NH$_4$)$^+$, 265 (M+H)$^+$.

EXAMPLE 158

Preparation of N-hydroxy-N-[4-(4-chlorophenoxy)thien-2-yl]methyl urea

The title compound was prepared as described in Example 157 except using 4-chlorophenol instead of phenol. mp: 141°-142° C.; NMR (300 MHz, DMSO d$_6$) δ 4.58 (2H, s), 6.47(2H, bs), 6.79 (1H, d, J=1 Hz), 6.85 (1H, d, J=1 Hz), 7.05 (2H, m), 7.43 (2H, m), 9.48 (1H, s); MS m/e (DCI/NH$_3$) 316 (M+NH$_4$)$^+$, 299 (M+H)$^+$.

Lipoxygenase Inhibition Determination

Assays to determine 5-lipoxygenase inhibitory activity were performed in 200 mL incubations containing the 20,000xg supermatant from 1.5 million homogenized RBL-1 cells and various concentrations of the test compound. Reactions were initiated by addition of radiolabeled arachidonic acid and terminated by acidification and ether extraction. Reaction products were separated from nonconverted substrate by thin layer chromatography and measured by liquid scintillation spectroscopy. All incubations are performed in triplicate. Inhibition of 5-lipoxygenase activity was calculated as the ratio of the amount of product formed in the presence and absence of inhibitor. IC$_{50}$ values (concentration of compound producing 50% enzyme inhibition) were calculated by linear regression analysis of percentage inhibition versus log inhibitor concentration plots. (Dyer, R.D.; Haviv, F.; Hanel, A. M.; Bornemier, D. A.; Carter, G. W. Fed. Proc., Fed. Am. Soc. Exp. Biol. 1984, 43, 1462A). Results for compounds of the foregoing examples are indicated in Table 1.

TABLE 1

In Vitro Inhibitory Potencies of Compounds of this Invention Against 5-Lipoxygenase from RBL-1 20,000 xg Supernatant

| Example | IC$_{50}$ (10$^{-6}$M) | Example | IC$_{50}$ (10$^{-6}$M) |
|---|---|---|---|
| 1 | 0.43 | 108 | 0.4 |
| 2 | 0.37 | 109 | 1.8 |
| 3 | 0.68 | 110 | 2.3 |
| 4 | 0.50 | 113 | 0.3 |
| 5 | 0.61 | 114 | 0.9 |
| 6 | 0.54 | 115 | 0.6 |
| 7 | 1.4 | 116 | 4.4 |
| 8 | 0.33 | 117 | 4.43 |
| 10 | 0.87 | 119 | 0.53 |
| 11 | 1.1 | 120 | 0.57 |
| 12 | 0.53 | 121 | 0.74 |
| 13 | 2.8 | 122 | 0.80 |
| 42 | 1.5 | 123 | 0.50 |
| 43 | 3.5 | 124 | 0.60 |
| 44 | 4.9 | 125 | 0.40 |
| 45 | 6.8 | 126 | 0.80 |
| 46 | 2.1 | 127 | 1.2 |
| 47 | 3.7 | 128 | 2.5 |
| 48 | 1.7 | 129 | 2.0 |
| 49 | 3.1 | 130 | 0.9 |
| 50 | 6.7 | 132 | 0.9 |
| 51 | 0.2 | 133 | 0.9 |
| 52 | 3.9 | 134 | 0.3 |
| 53 | 0.2 | 135 | 0.2 |
| 54 | 0.31 | 137 | 0.4 |
| 55 | 2.1 | 139 | 0.4 |
| 56 | 0.4 | 140 | 0.4 |
| 57 | 0.42 | 141 | 0.2 |
| 58 | 0.15 | 142 | 0.3 |
| 59 | 0.99 | 143 | 0.3 |
| 60 | 3.5 | 144 | 0.2 |
| 61 | 2.1 | 145 | 1.5 |
| 62 | 4.2 | 146 | 0.7 |
| 68 | 1.9 | 147 | 3.7 |
| 69 | 1.5 | 148 | 0.3 |
| 72 | 0.8 | 149 | 0.8 |
| 97 | 0.2 | 154 | 0.2 |
| 98 | 1.1 | 155 | 0.7 |
| 99 | 0.3 | | |
| 100 | 0.8 | 156 | 1.0 |
| 101 | 0.3 | 157 | 0.5 |
| 104 | 3.9 | 158 | 0.4 |
| 107 | 0.6 | | |

In vivo Inhibition of Leukotriene Biosynthesis

Inhibition of the biosynthesis of leukotrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. From the results of this assay, presented in Table 2, it is demonstrated that compounds of this invention are orally effective in preventing the in vivo biosynthesis of leukotrienes.

TABLE 2

In Vivo Inhibition of Leukotriene Biosynthesis
Percent Inhibition at 200 μmol/kg Oral Dose

| Example | % Inhibition | Example | % Inhibition |
|---|---|---|---|
| 1 | 58 | 55 | 71 |
| 4 | 63 | 56 | 89 |
| 5 | 74 | 68 | 93 |
| 7 | 88 | 97 | 94 |
| 9 | 69 | 99 | 84 |
| 12 | 94 | 100 | 95 |
| 42 | 64 | 101 | 93 |
| 43 | 66 | 102 | 85 |
| 44 | 87 | 103 | 88 |
| 45 | 97 | 107 | 99 |
| 47 | 94 | 109 | 98 |
| 49 | 94 | 111 | 97 |
| 50 | 90 | 113 | 94 |
| 51 | 94 | 120 | 77 |

We claim:
1. A compound of the formula

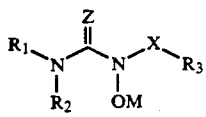

or a pharmaceutically acceptable salt thereof, wherein
Z is oxygen or sulfur,
X is selected from the group consisting of
  alkylene of from one to six carbon atoms;
  alkenylene of from two to six carbon atoms;
  alkylene of from one to six carbon atoms substituted by a group selected from
    hydroxy,
    halo,
    cyano,
    alkoxy,
    aminocarbonyl,
    alkylaminocarbonyl,
    dialkylaminocarbonyl,
    carboxyl, and
    alkoxycarbonyl;
  alkenylene of from two to six carbon atoms substituted by a group selected from
    hydroxy,
    halo,
    cyano,
    alkoxy,
    aminocarbonyl,
    alkylaminocarbonyl,
    dialkylaminocarbonyl,
    carboxyl, and
    alkoxycarbonyl;
$R^1$ and $R^2$ are independently selected from the group consisting of
  hydrogen;
  hydroxy;
  alkyl of from one to six carbon atoms;
  alkyl of from one to six carbon atoms substituted with a group selected from
    hydroxy;
    halo;
    cyano;
    alkoxy;
    alkylthio;
    aminocarbonyl;
    alkylaminocarbonyl;
    dialkylaminocarbonyl;
    carboxy;
    alkoxycarbonyl;
    aryl; and
  aryl substituted with a substituent selected from the group consisting of
    hydroxy,
    halo,
    cyano,
    alkoxy,
    alkylthio,
    amino,
    alkylamino,
    dialkylamino,
    aminocarbonyl,
    alkylaminocarbonyl,
    dialkylaminocarbonyl,
    carboxyl, and
    alkoxycarbonyl;
$R^3$ is selected from the group consisting of
  thienyl; and
  thienyl substituted by
    alkyl of from one to six carbon atoms,
    alkenyl of from two to six carbon atoms,
    cycloalkyl of from three to ten carbon atoms,
    alkoxy of from one to six carbon atoms,
    alkylthio of from one to six carbon atoms,
    halo,
    nitro,
    hydroxy;
  substituted or unsubstituted aryl,
  substituted or unsubstituted aryloxy,
  substituted or unsubstituted aroyl,
  substituted or unsubstituted arylalkyl wherein the alkyl portion contains from one to six carbon atoms,
  substituted or unsubstituted arylalkenyl wherein the alkenyl portion contains from two to six carbon atoms,
  substituted or unsubstituted arylalkynyl wherein the alkynyl portion contains from two to six carbon atoms,
  substituted or unsubstituted arylalkoxy wherein the alkoxy portion contains from one to six carbon atoms,
  substituted or unsubstituted arylalkylthio wherein the alkylthio portion contains from one to six carbon atoms,
  wherein said substituted aryl groups are optionally substituted by one, two, or three groups independently selected from the group consisting of halo, nitro, cyano, alkyl, alkoxy, and halosubstituted alkyl;
M is selected from the group consisting of
  hydrogen,
  a pharmaceutically acceptable cation,
  a metabolically cleavable group,
  aroyl,
  —Si($R^5$)$_3$ wherein $R^5$ is independently selected at each occurrence from alkyl of from one to six carbon atoms,
  —C(O)R$_4$,
  —CH$_2$OR$_4$,
  —C(O)N($R^4$)$_2$ and
  —C(O)OR$^4$
    wherein $R^4$ is alkyl of one to six carbon atoms;
with the proviso that $R^1$ and $R^2$ are not simultaneously hydroxy.

2. A compound as defined by claim 1 having the structure

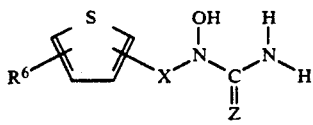

where X and Z are as defined therein;
R⁶ is selected from the group consisting of
hydrogen;
alkyl of from one to six carbon atoms;
halogen;
phenyl;
phenyl substituted by
  alkyl of from one to six carbon atoms,
  alkoxy of from one to six carbon atoms,
  hydroxy, or
  halogen;
phenoxy;
phenoxy substituted by
  alkyl of from one to six carbon atoms,
  alkoxy of from one to six carbon atoms,
  hydroxy, or
  halogen;
phenylthio;
phenylthio substituted by
  alkyl of from one to six carbon atoms,
  alkoxy of from one to six carbon atoms,
  hydroxy,
  halogen; or
a pharmaceutically acceptable salt thereof.

3. A compound as defined by claim 1 selected from the group consisting of
N-hydroxy-N-(thien-2-yl)methyl urea;
N-hydroxy-N-(thien-3-yl)methyl urea;
N-hydroxy-N-(1-(thien-3-yl)ethyl) urea;
N-hydroxy-N-(1-(thien-3-yl)ethyl) thiourea;
N-hydroxy-N-(3-(1-thien-3-yl)propyl)urea;
N-hydroxy-N-(3-(thien-3-yl)propen-1-yl) urea;
N-hydroxy-N-(3-methylthien-2-yl)methyl urea;
N-hydroxy-N-(2-(5-methylthien-2-yl)propyl) urea;
N-hydroxy-N-(5-bromothien-2-yl)methyl urea;
N-hydroxy-N-(1-(5-bromothien-2-yl)ethyl]urea;
N-hydroxy-N-(1-(5-phenylthien-2-yl)methyl) urea;
N-hydroxy-N-(1-(5-phenylthien-2-yl)ethyl) urea;
N-hydroxy-N-(4-(phenoxy)thien-2-yl)methyl urea
N-hydroxy-N-(4-(4-chlorophenoxy)thien-2-yl)methyl urea
N-hydroxy-N-(3-(phenylthio)thien-2-yl)methyl urea
N-hydroxy-N-(3-(4-chlorophenylthio)thien-2-yl)methyl urea
N-hydroxy-N-(4-(phenylthio)thien-2-yl)methyl urea
N-hydroxy-N-(5-(phenylthio)thien-2-yl)methyl urea
N-hydroxy-N-((2-(phenylthio)thien-3-yl)methyl urea
N-hydroxy-N-((5-(phenylthio)thien-3-yl)methyl urea
N-hydroxy-N-(1-(5-(phenylthio)-thien-2-yl)ethyl)urea
N-hydroxy-N-(3-(5-(phenylthio)thien-2-yl)propen-1-yl) urea
N-hydroxy-N-(3-(5-(phenylthio)thien-2-yl)butenyl urea 4. A pharmaceutical composition for inhibiting lipoxygenase enzymes comprising an effective amount of a compound as defined by claim 1 in combination with a pharmaceutically accpetable carrier.

5. A method of inhibiting lipoxygenase enzyme activity in a mammal comprising administering to a mammal in need of such treatment an effective amount of a compound as defined by claim 1.

* * * * *